US 8,105,601 B2

(12) United States Patent
Mills et al.

(10) Patent No.: US 8,105,601 B2
(45) Date of Patent: Jan. 31, 2012

(54) COMPOSITIONS AND METHODS FOR MODULATING AN IMMUNE RESPONSE

(75) Inventors: Kingston Mills, Dublin (IE); Miriam Brady, Dartford (IE)

(73) Assignee: The Provost, Fellows and Scholars of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 150 days.

(21) Appl. No.: 12/096,239

(22) PCT Filed: Dec. 5, 2006

(86) PCT No.: PCT/IE2006/000136
§ 371 (c)(1),
(2), (4) Date: Jun. 5, 2008

(87) PCT Pub. No.: WO2007/066313
PCT Pub. Date: Jun. 14, 2007

(65) Prior Publication Data
US 2008/0260784 A1    Oct. 23, 2008

(30) Foreign Application Priority Data
Dec. 5, 2005    (IE) .................................... 2005/0811

(51) Int. Cl.
*A61K 39/00*    (2006.01)
*A61K 39/002*    (2006.01)
(52) U.S. Cl. .................................... 424/184.1; 424/265.1
(58) Field of Classification Search .................... None
See application file for complete search history.

(56) References Cited

U.S. PATENT DOCUMENTS

| 3,773,919 | A | 11/1973 | Boswell et al. | |
| 6,551,594 | B1 * | 4/2003 | van Milligen et al. | 424/191.1 |
| 2003/0022249 | A1 * | 1/2003 | Schmitz et al. | 435/7.21 |
| 2003/0135875 | A1 * | 7/2003 | Ehrhardt et al. | 800/18 |
| 2004/0202647 | A1 * | 10/2004 | Birnboim et al. | 424/130.1 |

FOREIGN PATENT DOCUMENTS

EP    0 058 481    8/1982

OTHER PUBLICATIONS

Brady et al., "*Fasciola hepatica* Induces Regulatory T Cells and Suppresses Th17-Mediated Autoimmunity," *Immunology*, 120(Supp.1):8 (2007).
Brady et al., "*Fasciola hepatica* Suppresses a Protective Th1 Response Against *Bordetella pertussis*," *Infection and Immunity*, 67(10):5372-5378 (1999).
Brady et al., "Helminth Infection Suppresses Effector T Cell Responses Through Dendritic Cell Modulation and Regulatory T-Cell Induction," *Immunology*, 116(Supp.1):23 (2005).
Cervi et al., "Immunization of Rats Against *Fasciola hepatica* using Crude Antigens Conjugated with Freund's Adjuvant or Oligodeoxynucleotides," *Veterinary Immunology and Immunopathology*, 97(1-2):97-104 (2004).
Cervi et al., "Involvement of Excretion-Secretion Products from *Fasciola hepatica* Inducing Suppression of the Cellular Immune Response," *Veterinary Parasitology*, 61(1-2):97-111 (1996).
Donnelly et al., "Thioredoxin Peroxidase Secreted by *Fasciola hepatica* Induces the Alternative Activation of Macrophages," *Infection and Immunity*, 73(1):166-173 (2005).
Furuzawa-Carballeda et al., "Autoimmunity Inflammation from the Th17 Perspective," *Autoimmunity Reviews*, 6(3):169-175 (2007).
Irving et al., "Characterization of Excretory Secretory Antigens of *Fasciola hepatica*," *Parasitology*, 85(1):179-188 (1982).
Komiyana et al,, "IL-17 Plays an Important Role in the Development of Experimental Autoimmune Encephalomyelitis," *Journal of Immunology*, 177(1):566-573 (2006).
Langer et al., *J. Biomed. Mater. Res.*, 15:167-277 (1981).
Langer, *Chem. Tech.*, 12:98-105 (1982).
O'Neill et al., "*Fasciola hepatica* Cathepsin L Cysteine Proteinase Suppresses *Bordetella pertussis*-specific Interferon-gamma Production in Vivo," *Parasite Immunology*, 23(10):541-547(2001).
O'Neill et al., "*Fasciola hepatica* Infection Downregulates Th1 Responses in Mice," *Parasite Immunology*, 22(3):147-155 (2000).
Sidman et al., *Biopolymers*, 22(1):547-556 (1985).
International Search Report for International Application No. PCT/IE2006/00136, dated May 23, 2007.

* cited by examiner

*Primary Examiner* — Albert Navarro
(74) *Attorney, Agent, or Firm* — Marshall, Gerstein & Borun LLP

(57) ABSTRACT

The present invention provides a composition for suppressing an inflammatory immune response comprising the excretory/secretory (ES) component of *Fasciola hepatica* or a fraction thereof. The composition has particular utility in the treatment or prophylaxis of T cell mediated inflammatory immune responses, and in particular autoimmune disease. The invention further extends to methods for modulating a T cell mediated immune response wherein a therapeutically effective amount of the excretory/secretory (ES) component from *Fasciola hepatica* is administered to a subject in need of such treatment in order to suppress the development of the response.

10 Claims, 50 Drawing Sheets

A

B

COMPOSITIONS AND METHODS FOR MODULATING AN IMMUNE RESPONSE

FIELD OF THE INVENTION

The present invention relates to novel compositions and methods for modulating an immune response in order to prevent or treat disease and/or conditions where T lymphocyte cells have a pathogenic role, such as Th1 or ThIL-17 mediated inflammatory conditions, chronic inflammatory conditions and autoimmune diseases.

BACKGROUND OF THE INVENTION

Cells of the innate immune system, especially dendritic cells (DCs), direct the differentiation of naïve $CD4^+$ T cells into functionally distinct Th1, Th2, ThIL-17 (also known as Th17) or regulatory T (Tregs) cell subtypes. Activation of immature DCs through binding of conserved microbial molecules to pathogen recognition receptors (PRRs), such as Toll-like receptors (TLRs) and integrins, is accompanied by DC maturation and homing to the lymph nodes, where the mature DCs present antigen (Ag) to naïve T cells. Activation of dendritic cells by pathogen derived molecules plays a critical role in regulating the differentiation of naïve $CD4^+$ T cells into distinct T cell subtypes. Th1 cells confer protection against intracellular infection but are also associated with inflammatory responses and autoimmune disease, whereas Th2 cells are involved in allergic responses. IL-17 producing T cells (ThIL-17 or Th17) are a pathogenic subset of T cells which are characterised by the production of IL-6, TNF-alpha and, in particular, IL-17 and IL-17F, important pro-inflammatory cytokines which contribute to autoimmune disease. Treg cells are capable of suppressing Th1, Th2 and Th17 responses.

Immune Mediated Conditions

Multiple sclerosis (MS) is an autoimmune disease that affects the central nervous system. Individuals with this disease have autoreactive T cells (T cells that recognize self antigens), which together with interleukin (IL)-1beta and tumour necrosis factor (TNF) alpha, participate in the formation of inflammatory lesions along the myelin sheath of nerve fibres. The cerebrospinal fluid (CSF) of patients with MS contains activated T cells, which infiltrate the brain tissue and cause the characteristic inflammatory lesions, destroying the myelin. Experimental autoimmune encephalomyelitis (EAE) is an animal model for MS. It is induced in mice or rats by injection of mylein basic protein (MBP) or myelin oligodendrocyte glycoprotein (MOG) or peptides thereof with complete Freund's adjuvant. The disease can also be induced by transfer of MBP or MOG-specific T cells that secrete IL-17 (called ThIL-17 cells or Th17 cells). The animals develop cellular infiltration of the myelin sheaths of the central nervous system, resulting in demyelination and eventually paralysis. The clinical signs and pathological changes resemble MS.

Crohn's disease and ulcerative colitis are inflammatory bowel diseases in humans. These autoimmune diseases are inflammatory conditions of the intestine mediated by $CD4^+$ T cells.

Many autoimmune and chronic inflammatory diseases have no satisfactory treatment and in most cases steroids and non-steroidal anti-inflammatory drugs are employed. However, these are non-specific and have side effects. More recently, drugs that inhibit key inflammatory cytokines, in particular tumour necrosis factor-alpha (TNF-alpha), have been developed. These include antibodies or soluble TNF receptors that are effective against certain autoimmune diseases, but are associated with side effects (including recurrent tuberculosis and cancers) and are limited to diseases where TNF-alpha is the key mediator of pathology. Another therapeutic approach is the direct administration of anti-inflammatory cytokines (e.g. IL-10), but this is compromised by the short half-life of cytokines in vivo. Alternative strategies employ agents that induce anti-inflammatory cytokines, such as IL-10, which will have a direct immunosuppressive effect in vivo. Molecules that promote the induction of suppressor or regulatory T cells have the potential to limit inflammatory Th1-mediated immune responses and also the T cells which secrete IL-17 (ThIL-17) which also mediate inflammatory responses in T cell mediated autoimmune responses.

Helminth Infection

Infection with Helminth parasites has been associated with immunosuppression and compromised T-cell responses. Infection with the liver fluke *Fasciola hepatica* induces highly polarized Th2 responses in mice, with high levels of the cytokines IL-4, IL-5 and IL-10 and also IgG1 antibodies. Infection with *F. hepatica* suppressed IFN-gamma secreting T cell (Th1 cell) responses and protection against the bacterial pathogen, *Bordetella pertussis*. Infection with *F. hepatica* also inhibited Th1 responses and protection against *B. pertussis* induced with a whole cell pertussis vaccine.

*F. hepatica* excretory/secretory (ES) components have also been shown to suppress Th1 responses induced by a whole cell *B. pertussis* vaccine. This suppression was shown to be reversed by an inhibitor of cathepsin L proteinase, this suggesting that cathepsin L proteinase was responsible for mediating the suppressive effect.

Further, cathepsin L proteinase purified from *F. hepatica* ES component suppressed Th1 response induced with Pw vaccine. These studies also demonstrated that the suppression induced by *F. hepatica* or the cathepsin L proteinase were mediated by IL-4 as suppression of the immune response was seen to be reversed in IL-4 defective mice.

The conclusion of the above studies was therefore that cathepsin L proteinase was responsible for, and mediated the suppressive effect of, *F. hepatica* and *F. hepatica* ES component and that the suppression was mediated through IL-4 induction.

A method of preventing the onset and progression of autoimmune diseases, inflammatory conditions or immune mediated disorders through the modulation of the T cell responses which are causative of these conditions would be highly advantageous in the prevention and treatment of these conditions.

The inventors of the present invention have surprisingly identified that the excretory/secretory (ES) component of *Fasciola hepatica* comprises compounds other than cathepsin L proteinase which mediate suppression of the immune response. While it was considered that suppression of the immune response by cathepsin L proteinase was mediated by IL-4 cytokine production, the present inventors have identified that the ES component mediates immune suppression through a number of alternative mechanisms which serve to modulate the immune response. In particular, the inventors have identified that the excretory/secretory (ES) component of *Fasciola hepatica* interacts with the cells of the innate immune system to modulate the immune response through the modulation of cytokine expression, in particular the upregulation of IL-10 cytokine levels, through the activation of dendritic cells into a phenotype which promotes a T regulatory phenotype (which produces IL-10) and which skews the immune response away from the production of T cells having a Th1 and/or ThIL-17 phenotype.

In particular, the inventors have identified that the ES component of *F. hepatica* stimulates the production of anti-inflammatory cytokines, such as IL-10, which can serve as potent modulators of the immune response.

Further, the inventors have also surprisingly shown that the ES fraction from *F. hepatica* can activate dendritic cells into a phenotype that promotes the production of regulatory T cells (Tregs), these Tregs in turn modulating the immune response, through the suppression of Th1 and ThIL-17 type responses. In particular, such dendritic cells have been shown to exhibit low expression levels of cell surface markers CD80, CD86, CD40 and MHC class II, while higher expression levels of CCR5 are observed over the expression levels of these cell surface markers on naïve dendritic cells. The IL-17 producing T cell subset secretes a cytokine profile including IL-17, IL-17F, IL-17H, IL-17F, IL-17A, IL-6 and TNF. IL-17 producing T (Th17 (ThIL-17)) cells, driven by IL-1 and IL-23 or IL-6 and TGF-beta, are a distinct subtype of inflammatory T cells from Th1 cells and are pathogenic in many autoimmune diseases and chronic inflammatory conditions.

These effects are independent to the immune modulatory effects which have been hitherto observed in relation to cathepsin L proteinase. Importantly, the immunomodulatory effects observed by the present inventors are not suppressed by cathepsin L proteinase inhibitors and are not IL-4 dependent. Without wishing to be bound by theory, the inventors therefore predict that the immunomodulatory effects mediated by the ES component are mediated, at least in part, by components or products derived from the ES component other than a cathepsin L proteinase.

Modulation of the response and cytokine profile expressed by a specific cell type of the immune system can lead, in turn, to a wider modulation of the overall immune response. The inventors have further surprisingly shown that the ES fraction from *F. hepatica* inhibits the induction of IFN-gamma, IL-17 producing Th1 cells (Th17 (ThIL-17) cells) and Th1 cells, through either the inhibition of IL-12 and IL-23, which promotes expansion of the Th1 and ThIL-17 cells, or by inhibiting the activation of Th1 and ThIL-17 cells, or by suppressing the function of Th1 and ThIL-17 cells.

SUMMARY OF THE INVENTION

According to a first aspect of the present invention there is provided a composition for the treatment or prophylaxis of a T cell mediated inflammatory immune response, said composition comprising the excretory/secretory (ES) component of *Fasciola hepatica* or a fraction thereof, or a derivative product, or a mutant, fragment or variant of a protein or peptide isolated therefrom.

Where the composition comprises a fraction, derivative product, mutant, fragment or variant of a protein or peptide isolated from the ES component of *Fasciola hepatica*, then said fraction or molecule exhibits the same immune modulatory activity as identified by the inventors herein in relation to the ES component, namely, the suppression of the production and/or activity of IFN-gamma, IL-17 producing Th1 cells (Th17 (ThIL-17) cells) and Th1 cells, through either the inhibition of IL-12 and IL-23, which promotes expansion of the Th1 and ThIL-17 cells, or by inhibiting the activation of Th1 and ThIL-17 cells, or by suppressing the function of Th1 and ThIL-17 cells.

Suitably the protein isolated from the ES component is not Cathepsin L. Suitably the T cell mediated inflammatory immune response treated by the composition is a pro-inflammatory immune response. Typically the pro-inflammatory immune response is a Th1 mediated immune response, the development of which is suppressed following the administration of the composition of this aspect of the invention. In particular, the composition suppresses or inhibits the induction and function of Th1 cells. Suitably, said suppression or inhibition of the production of Th1 cells is caused by the production of anti-inflammatory cytokines, in particular IL-10. Suitably, IL-10 production is induced following dendritic cell maturation which is induced by administration of the ES component or a fraction or product thereof. Said suppression may further be mediated by the enhancement of the production or function of the cytokine TGF-beta. Further, said suppression of the pro-inflammatory immune response may result from the ES component or components thereof stimulating Tregs (regulatory T cells) to mediate suppression of a pro-inflammatory immune response by cell to cell contact.

Suitably the ES component comprises the excretory/secretory product released by the *Fasciola hepatica* parasites. In one embodiment the ES component may be provided in an isolated or purified form. The ES component may be obtained by collection of the ES component from live tissues.

In an alternative embodiment the ES component may be fractionated into a plurality of fractions, with at least one of said resulting fractions being used in the composition of this aspect of the invention. In a further embodiment, specific molecules may be isolated or purified from the ES component. In a further embodiment, the specific molecule may be produced by recombinant means.

In one embodiment, the ES component lacks at least one cathepsin L proteinase (FhCatL) protein.

In further embodiments, fractions or peptides isolated or identified as being present within the ES component are produced by recombinant means. Such a product may contain more than one peptide component as identified from the ES component.

A second aspect of the present invention provides a pharmaceutical composition for the prevention and/or treatment of a T cell mediated pro-inflammatory condition, wherein the composition comprises the excretory/secretory (ES) component of *Fasciola hepatica* or a fraction or a derivative, mutant, fragment or variant of a protein or peptide isolated therefrom along with a pharmaceutically acceptable excipient or carrier.

By T cell mediated pro-inflammatory condition, we mean an immune response which is pro-inflammatory in nature, which is mediate by Th1 cells and CTLs (cytotoxic T lymphocytes). The pro-inflammatory response may be driven by pro-inflammatory cytokines such as IL-12 and IFN-gamma.

According to a further aspect of the present invention there is provided a method for modulating a T cell mediated immune response in a subject in need of such treatment, the method comprising the steps of;

administering to a subject in need of such treatment an effective amount of an agent comprising the excretory/secretory (ES) component from *Fasciola hepatica* or a fraction or derivative product, a mutant, fragment or variant of a protein or peptide isolated therefrom.

Suitably the ES component of *Fasciola hepatica*, or the fraction or derivative product, mutant, fragment or protein derived therefrom, serves to mediate at least one of:
an increase in IL-10 cytokine levels in the subject;
an increase in TGF-beta cytokine levels in the subject;
an increase in regulatory T cells;
a decrease in at least one pro-inflammatory cytokine such as IL-12, IL-2 and/or IFN-gamma;
a decrease in cytotoxic T lymphocytes;
a decrease in Th1 cells; or
a decrease in a mixed lymphocyte response.

Suitably the T cell mediated immune response is a T cell mediated pro-inflammatory immune response.

Suitably the subject is in need of treatment of, or protection against, an autoimmune disease.

In one embodiment of this aspect of the invention the T cell mediated pro-inflammatory immune response is suppressed. Without wishing to be bound by theory, this suppression may result from the step of contacting an immune cell with an agent comprising the excretory/secretory (ES) component from *Fasciola hepatica*, in accordance with the method of this aspect of the invention.

As herein defined, the term "upregulation" when used in relation to the increase in the production of a cytokine means that the activity or expression of that cytokine is greater than that observed in resting cells.

As herein defined, the term "suppression" when used in relation to the decrease in the production of a cytokine means that the activity or expression of the cytokine is lower than that observed in resting cells.

As herein defined, the term "inhibition" when used in relation to the inhibition in the production of a cytokine means that the activity or expression of the cytokine is inhibited or substantially inhibited when compared to the activity or expression level observed in resting cells.

Suitably the administration of the ES component results in the suppression of a pro-inflammatory cytokine such as IL-12 and/or IFN-gamma and the upregulation of an anti-inflammatory cytokine such as IL-10 and/or TGF-beta.

A further embodiment of the invention provides for the effective amount of the agent comprising the excretory/secretory (ES) component from *Fasciola hepatica* or a derivative product, or a mutant, fragment or variant of a protein or peptide isolated therefrom to couple, bind or otherwise associate with at least one cell surface activation molecule of at least one type of immune cell, this resulting in the suppression, inhibition or down-regulation of one or more functional activities of that cell.

In one embodiment of the invention the immune cell whose function is modulated is at least one cell of the innate immune system. Suitably, the cell is a cell type with antigen processing and presenting function, such as an antigen presenting cell (APC), for example a dendritic cell, or a macrophage, or a B cell.

Where the APC is a dendritic cell, it may be an immature dendritic cell, a semi-mature dendritic cell, or it may be a mature dendritic cell.

In a further embodiment the cell of the innate immune system is a cell which does not function as an antigen presenting cell, for example a mast cell. Mast cells secrete cytokines such as IL-4 and are accordingly known to have a role in facilitating the immune response. However, they do not have an associated antigen processing function.

In one embodiment, the subject is a mammal. In a further embodiment, the mammal is a human.

Without wishing to be bound by theory, the inventors of the present invention believe that the down-regulation of the T cell response which results following the administration of the excretory/secretory (ES) component from *Fasciola hepatica* is caused by modulating the activity of antigen presenting cells (APC), and in particular dendritic cells (DC), in inducing the production of regulatory T cells (Tregs) which express a profile of cytokines, such as IL-10 and/or TGF-beta, which suppress an immune response.

Without wishing to be bound by theory, the inventors believe that at least one specific protein molecule is present within the excretory/secretory (ES) component which is responsible for the modulation of immune function, said at least one protein being responsible for the observed immune modulation. In addition or in the alternative to the presence of a protein, a lipid, lipopeptide or peptide molecule may be present in the ES component and responsible for downregulation.

In addition to the promotion of the expression of IL-10, the ES component fraction may also induce expression of other anti-inflammatory cytokines from the cells of the innate immune system.

Further, although the inventors have identified that the dendritic cell function is modulated following exposure to the ES component, other cells of the innate immune system, such as macrophages, may also have their function modulated, with this modulation promoting an anti-inflammatory response.

Further, the ES component may further comprise at least one Toll-like receptor (TLR) ligand. However, in an alternative embodiment of this aspect of the invention, a TLR ligand (agonist) may be administered exogenously along with the composition of the invention.

Accordingly, in one embodiment the method may further include the step of administering at least one TLR agonist along with said composition.

The TLR agonist may have binding specificity for at least one of TLR-2, TLR-3, TLR-4, TLR-5, TLR-7, TLR-8 and TLR-9. Specific examples of suitable TLR agonists include, but are not limited to, Pam3CSK4, Zymosan, PolyIC, dsRNA, LPS (lipopolysaccharide), monophosphoryl lipid A (MPL), Flagellin, CpG-ODN (CPG-oligodeoxynucledtides), Imiquimod, R838 and R837. Further, whole bacteria such as *Bordetella pertussis* and *Mycobacterium tuberculosis* may also act as TLR agonists (Toll agonists). Further, suitable analogues to the TLR agonists listed above may also be used, wherein said analogues function to activate at least one Toll-like receptor.

A further aspect of the present invention provides a method for treating an autoimmune disease, comprising the steps of:
 (i) obtaining the ES component from *Fasciola hepatica* or a fraction thereof or a protein isolated therefrom; and
 (ii) administering a therapeutically effective amount of said ES component or fraction or peptide to an individual suffering from an autoimmune disease.

Suitably the autoimmune disease is selected from the group consisting of: rheumatoid arthritis or Multiple Sclerosis. Further autoimmune diseases are detailed hereinafter.

Suitably the ES component or fraction thereof or protein isolated therefrom is capable of suppressing an immune response selected from the group consisting of at least one of:
 inhibiting a mixed lymphocyte reaction;
 inhibiting a cytotoxic T lymphocyte response;
 induction of Th1 lymphocytes;
 induction of a Th1 cytokine profile;
 inhibiting IL-2 production;
 inhibiting IL-12 production; and
 inhibiting interferon gamma production.

Further, the ES component or fraction thereof or protein isolated therefrom may further suppress the development of the immune response by:
 enhancing IL-10 production;
 enhancing TGF-beta production;
 enhancing the function of regulatory T cells; and/or
 enhancing a Th2 cytokine profile.

As herein defined, the term "inhibition" when used in relation to the inhibition of the production of a cytokine means that the activity or expression of the cytokine is inhibited or substantially inhibited when compared to the activity or expression level observed in resting cells.

The term "administering an ES component protein" includes both the administration of the ES component protein as well as the administration of a nucleic acid sequence encoding an ES component protein. In the later case, the ES component protein is produced in vivo in the animal.

In order to obtain fractions or peptide derived from the ES component, the ES component may be separated by gel filtration chromatography, such as Sepharyl S-3000, and then analysed by polyacrylamide gel electrophoresis (SDS-PAGE) followed by Western.

By "effective amount" it is meant a concentration of ES component or the fraction thereof or protein isolated therefrom which, when administered to a patient suffering from an autoimmune disease, produces a therapeutically beneficial effect. The effective amount of ES component or the fraction thereof or protein isolated therefrom of the invention may vary according to factors such as the disease state, age, sex, and weight of the animal. Dosage regimes may be adjusted to provide the optimum therapeutic response. For example, several divided doses may be administered daily or the dose may be proportionally reduced as indicated by the exigencies of the therapeutic situation.

In another embodiment, the present invention provides a method of inducing immune tolerance to a transplanted organ or tissue in a recipient animal comprising administering an effective amount of the ES component from *Fasciola hepatica* or a fraction thereof or a protein isolated therefrom to the recipient animal prior to the transplantation of the organ or tissue.

The invention includes a use of an effective amount of the ES component from *Fasciola hepatica* or a fraction thereof or a protein isolated therefrom to induce immune tolerance to a transplanted organ or tissue.

The term "inducing immune tolerance" means rendering the immune system unresponsive to a particular antigen without inducing a prolonged generalized immune deficiency. The term "antigen" means a substance that is capable of inducing an immune response. In the case of autoimmune disease, immune tolerance means rendering the immune system unresponsive to an auto-antigen that the host is recognizing as foreign, thus causing an autoimmune response. In the case of allergy, immune tolerance means rendering the immune system unresponsive to an allergen that generally causes an immune response in the host. In the case of transplantation, immune tolerance means rendering the immune system unresponsive to the antigens on the transplant. An alloantigen refers to an antigen found only in some members of a species, such as blood group antigens. A xenoantigen refers to an antigen that is present in members of one species but not members of another. Correspondingly, an allograft is a graft between members of the same species and a xenograft is a graft between members of a different species.

The recipient can be any member of the animal kingdom including rodents, pigs, cats, dogs, ruminants, non-human primates and preferably humans. The organ or tissue to be transplanted can be from the same species as the recipient (allograft) or can be from another species (xenograft). The tissues or organs can be any tissue or organ including heart, liver, kidney, lung, pancreas, pancreatic islets, brain tissue, cornea, bone, intestine, skin and heamatopoietic cells.

The method of the invention may be used to prevent graft versus host disease wherein the immune cells in the transplant mount an immune attack on the recipient's immune system. This can occur when the tissue to be transplanted contains immune cells, such as when bone marrow or lymphoid tissue is transplanted when treating leukaemias, aplastic anemias and enzyme or immune deficiencies, for example.

Accordingly, in another embodiment, the present invention provides a method of preventing or inhibiting graft versus host disease in a recipient animal receiving an organ or tissue transplant comprising administering an effective amount of the ES component from *Fasciola hepatica* or a fraction thereof or a protein isolated therefrom to the organ or tissue prior to the transplantation in the recipient animal.

The invention includes a use of an effective amount of the ES component from *Fasciola hepatica* or a fraction thereof or a protein isolated therefrom to prevent or inhibit graft versus host disease.

The methods of the present invention may also be used to treat or prevent an allergic reaction. In an allergic reaction, the immune system mounts an attack against a generally harmless, innocuous antigen or allergen. Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

Accordingly, in a further embodiment, the present invention provides a method of preventing or treating an allergy comprising administering an effective amount of the ES component from *Fasciola hepatica* or a fraction thereof or a protein isolated therefrom to an animal having, or suspected of having, an allergy. The invention includes a use of an effective amount of the ES component from *Fasciola hepatica* or a fraction thereof or a protein isolated therefrom to prevent or treat an allergy.

In another aspect, the present invention provides a method of preventing immune suppression mediated in a host suffering from infection with *Fasciola hepatica* comprising administering an effective amount of the ES component from *Fasciola hepatica* or a fraction thereof to an animal in need thereof.

A further aspect of the present invention relates to a method for the treatment and/or prophylaxis of a disease or a condition that would benefit from the down-regulation of an immune response, the method comprising the step of:

administering to a subject in need of such treatment, a therapeutically effective amount of an agent comprising the excretory/secretory (ES) component from *Fasciola hepatica* or a fraction, or a derivative, mutant, fraction, fragment or variant of a protein or peptide isolated therefrom.

Suitably the immune response is an inflammatory immune response, such as the immune response mediated by Th1 cells or ThIL-17 cells.

The subject may be a mammal, in particular a human. Suitably, the subject has a condition which is an immune mediated condition, such as an allergy or an autoimmune disorder. In one embodiment the condition is an autoimmune disease, in particular a Th1-mediated and/or ThIL-17-mediated autoimmune disease.

In specific embodiments, the immune mediated disease may include, but not be limited to autoimmune conditions and diseases such as, but not limited to; multiple sclerosis, Crohn's disease, inflammatory bowel disease, type 1 diabetes, type 2 diabetes, stroke, atherosclerosis, arthritis (including rheumatoid arthritis, juvenile rheumatoid arthritis, osteoarthritis, psoriatic arthritis), psoriasis, lupus erythematosus, systemic lupus erythematosus, Hashimotos thyroiditis, myasthenia gravis, autoimmune anemia, thrombocytopenia, asthma or an atopic disease.

The definition of "immune-mediated disease" also includes other immune-mediated disorders such as one or more of dermatitis (including atopic dermatitis and eczematous dermatitis), Sjogren's Syndrome, including keratoconjunctivitis sicca secondary to Sjogren's Syndrome, alopecia aerate, allergic responses due to arthropod bite reactions, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, colitis, primary biliary cirrhosis, uveitis posterior, interstitial lung fibrosis, and coeliac disease.

In further embodiments, the disease or condition may include neurodegenerative conditions where the expression of specific cytokine profiles has been shown to contribute to the onset or progression of disease. Such conditions and diseases may include Alzheimer's disease (AD), mild cognitive impairment (MCI), multiple sclerosis (MS), Parkinson's disease, Amyotrophic lateral sclerosis (ALS), Huntington's disease, prion diseases such as CJD, AIDS-related dementia, encephalitis, stroke and head trauma.

The neurodegenerative condition may also include acute inflammation conditions of the brain which result following bacterial and viral infections.

In addition to the above indicated autoimmune conditions, the present invention may be extended to any immune mediated disorder where an undesirable or unwanted immune response is triggered by the presentation of antigen.

Accordingly, a yet further aspect of the present invention provides a method for the prophylaxis and/or therapeutic treatment of a condition characterised by an aberrant, unwanted or otherwise inappropriate immune-mediated response in a subject, the method comprising administering to the subject an effective amount of an agent comprising the excretory/secretory (ES) component from *Fasciola hepatica* or a fraction, derivative product, or a mutant, fragment or variant of a protein or peptide isolated therefrom, which agent couples, binds or otherwise associates with at least one cell type belonging to the innate immune system, for a time and under conditions sufficient to suppress, inhibit or otherwise down-regulate the immune activity of said cell type.

Typically the at least one cell type which belongs to the innate immune system comprises an antigen presenting cell (APC) such as a dendritic cell (DC), or a follicular DC, a macrophage or a B cell. Alternatively the at least one cells type which belongs to the innate immune system may be at least one cell which does not exhibit specific antigen presenting cell function such as mast cells.

Where the APC is a dendritic cell, it may be an immature, semi-mature, or a mature dendritic cell.

A further aspect of the present invention provides for the use of the excretory/secretory (ES) component from *Fasciola hepatica* or a fragment thereof or a derivative product, or a mutant, fragment or variant of a protein or peptide isolated therefrom for the treatment of an immune mediated disease.

A further aspect of the present invention provides for the use of the excretory/secretory (ES) component from *Fasciola hepatica* or a fragment, derivative product, or a mutant, fragment or variant of a protein or peptide isolated therefrom in the preparation of a medicament for the treatment of an immune mediated disease.

A yet further aspect of the present invention provides for the use of the excretory/secretory (ES) component from *Fasciola hepatica* or a derivative product, or a mutant, fragment or variant of a protein or peptide isolated therefrom in the preparation of a medicament for the treatment of an autoimmune disease.

In one embodiment, the ES component lacks the cathepsin L proteinases.

In a further embodiment, the composition further comprises a cathepsin L proteinase inhibitor.

A still further aspect of the present invention provides for the use of the excretory/secretory (ES) component from *Fasciola hepatica* or a fraction, derivative product, or a mutant, fragment or variant of a protein or peptide isolated therefrom in the preparation of a medicament for the treatment of an inflammatory condition.

A still further aspect of the present invention provides for the use of the excretory/secretory (ES) component from *Fasciola hepatica* or a derivative product, or a mutant, fragment or variant of a protein or peptide isolated therefrom in the preparation of a medicament for the treatment of a neurodegenerative disease.

A still further aspect of the present invention provides for the use of the excretory/secretory (ES) component from *Fasciola hepatica* or a derivative product, or a mutant, fragment or variant of a protein or peptide isolated therefrom in the preparation of a medicament for the treatment of a cardiac disease or condition.

Dendritic Cell Modulation

The inventors have further identified that the excretory/secretory (ES) component from *Fasciola hepatica* can be used to modulate the cytokine expression profile and maturation state of dendritic cells.

Dendritic cells are key modulators of the immune response. The cytokine profiles which they express have an important influence on the development of the immune response. In particular, cytokines expressed by dendritic cells can be important in skewing an immune response down the Th1 or Th2 pathway, or in inducing the production of ThIL-17 or T cells with suppressor activity.

Dendritic cells isolated from the peritoneal cavity of *F. hepatica* infected mice secreted high concentrations of IL-10 and had significantly lower cell surface expression of CD80, CD86, CD40 and MHC Class II, but higher levels of CCR5 than dendritic cells from naive mice. *F. hepatica* is seen to suppress T cell responses by inducing dendritic cell production of cytokines, such as IL-10 or TGF-$\beta$, which induce suppressor T cell activity.

Accordingly, a further aspect of the present invention provides a method for suppressing an immune response suitable for the treatment of an immune-mediated disease in a subject in need of such treatment, the method comprising the steps of:
exposing isolated dendritic cells to an agent comprising the excretory/secretory (ES) component from *Fasciola hepatica* or a fraction, derivative product, or a mutant, fragment or variant of a protein or peptide isolated therefrom ex-vivo in order to modulate the function of the dendritic cells; and
administering the dendritic cells to the subject;
whereby the immune response subsequently induced by the dendritic cells in the subject is sufficient to prevent the onset or progression of the immune-mediated disease.

In one embodiment, the dendritic cells are activated to express high levels of the cytokine IL-10, or other anti-inflammatory cytokines such as TGF-beta, or other cytokines which promote the induction of Tregs.

In one embodiment of this aspect of the invention the dendritic cells are autologous to the subject.

In one embodiment the dendritic cells are immature dendritic cells. Alternatively the dendritic cells are mature dendritic cells.

In a further embodiment the dendritic cells may be administered along with a Toll-Like Receptor (TLR) ligand, an example of which is Pam3Cys.

Further, a self-antigen may be optionally co-administered along with the dendritic cells. An example of a self antigen is MOG or myelin basic protein.

A yet further aspect of the present invention provides for the use of the excretory/secretory (ES) component of *Fasciola hepatica* for the treatment of dendritic cells in the preparation of a medicament for the treatment of an autoimmune disease.

Inhibition of IL-17 Activity

The present inventors have further surprisingly shown that the excretory/secretory (ES) component from *Fasciola hepatica* suppresses the induction of T cells which express IL-17 (so called ThIL-17 cells). IL-17 has been identified as a key modulator of the onset and progression of autoimmune diseases and chronic inflammatory conditions, in particular multiple sclerosis, colitis and rheumatoid arthritis. Accordingly the modulation of IL-17 levels by an agent comprising the excretory/secretory (ES) component from *Fasciola hepatica* or a derivative product, or a mutant, fragment or variant of a protein or peptide isolated therefrom provides a novel therapy applicable to the prophylaxis and/or treatment of autoimmune diseases and chronic inflammatory conditions.

According to a yet further aspect of the present invention there is provided a method of prophylaxis and/or treatment of an immune-mediated condition, the method comprising the step of:
  administering an agent comprising the excretory/secretory (ES) component from *Fasciola hepatica* or a derivative product, or a mutant, fragment or variant of a protein or peptide isolated therefrom,
wherein the administration of the agent serves to suppress or inhibit the production of T cells which secrete IL-17.

According to a still further aspect of the present invention there is provided a method of prophylaxis and/or treatment of an immune-mediated condition, the method comprising the step of:
  administering an agent comprising the excretory/secretory (ES) component from *Fasciola hepatica* or a derivative product, or a mutant, fragment or variant of a protein or peptide isolated therefrom,
wherein the administration of the agent serves to suppress or inhibit the production of IL-23.

Typically, the inhibition of IL-23 will further result in the inhibition of the production of IL-17.

A still further aspect of the present invention provides the use of the excretory/secretory (ES) component from *Fasciola hepatica* or a derivative, mutant, fragment or variant of a protein isolated therefrom in the preparation of a medicament to inhibit the production of IL-17 for the treatment of an immune-mediated disease.

IL-12 Suppression

The inventors have further identified that the production of IL-12 is suppressed as a result of ES administration. IL-12 has a role in effecting the promotion of immune responses, and in particular those mediated by Th1 and ThIL-17 cells. This suppression may further be extended to members of the IL-12 cytokine family, such as IL-23 and IL-27.

Accordingly, a further aspect of the invention provides a composition for the suppression of IL-12 production or the production of an IL-12 family member, said composition comprising the excretory/secretory (ES) component of *Fasciola hepatica* or a derivative product, or a mutant, fragment or variant of a protein or peptide isolated therefrom.

A further still aspect provides a pharmaceutical composition for use in the suppression of IL-12 production or the production of an IL-12 family member, wherein the composition comprises the excretory/secretory (ES) component of *Fasciola hepatica* or a derivative product, or a mutant, fragment or variant of a protein or peptide isolated therefrom. A yet further aspect of the present invention provides a method for suppressing the production of IL-12 or an IL-12 family member, the method comprising the step of;
  administering an effective amount of an agent comprising the excretory/secretory (ES) component from *Fasciola hepatica* or a product derivative, or a mutant, fragment or variant of a protein or peptide isolated therefrom.

In one embodiment, the IL-12 family member is IL-23 and/or IL-27.

Liver Fluke Homogenate (LFH)

In addition to the administration of the ES (excretory/secretory) component of *Fasciola hepatica* or a derivative product, or a mutant, fragment or variant of a protein or peptide isolated therefrom, the compositions, uses of said compositions and methods of the present invention can also be achieved through the use of liver fluke homogenate (LFH) instead of the ES component.

The inventors have surprisingly identified that the administration of LFH may modulate the expression of certain cytokines which have importance in immune mediated inflammatory conditions. For example, liver fluke homogenate (LFH) or a fraction, derivative product, or a mutant, fragment or variant of a protein or peptide isolated therefrom may modulate the expression levels of the cytokines IL-4 and IL-10.

Accordingly a further aspect of the invention provides a composition for the prevention and/or treatment of an inflammatory condition, said composition comprising liver fluke homogenate (LFH) or a derivative product, or a mutant, fragment or variant of a protein or peptide isolated therefrom.

In one embodiment the inflammatory condition is a T cell mediated inflammatory immune response.

A yet further aspect of the present invention provides a pharmaceutical composition for the prevention and/or treatment of an inflammatory condition, wherein the composition comprises liver fluke homogenate (LFH) or a derivative product, or a mutant, fragment or variant of a protein or peptide isolated therefrom.

In one embodiment the inflammatory condition is a T cell mediated inflammatory immune response.

A yet further aspect of the present invention provides a method for modulating an inflammatory condition, the method comprising the steps of;
  administering to a subject an effective amount of an agent comprising liver fluke homogenate (LFH) or a product derivative, or a mutant, fragment or variant of a protein or peptide isolated therefrom to a subject in need of such treatment.

In one embodiment the inflammatory condition is a T cell mediated inflammatory immune response.

In one embodiment, the inflammatory condition is an immune mediated condition, such as an allergy or an autoimmune disorder. In further embodiments, the condition is an autoimmune disease, in particular a Th1-mediated and/or ThIL-17-mediated autoimmune disease. In specific embodiments, the immune mediated disease may include, but not be limited to multiple sclerosis, Crohn's disease, inflammatory bowel disease, type 1 diabetes, type 2 diabetes, stroke, atherosclerosis, arthritis (including rheumatoid arthritis, juvenile rheumatoid arthritis, osteoarthritis, psoriatic arthritis), psoriasis, lupus erythematosus, systemic lupus erythematosus, Hashimotos thyroiditis, myasthenia gravis, autoimmune anemia, thrombocytopenia, asthma or an atopic disease.

In addition to identifying a novel and unexpected use for LFH in the modulation of immune-mediated conditions, such as those listed above, the present inventors have also surprisingly identified that LFH is particularly effective in modulating IL-4 levels.

According to a further still aspect of the present invention there is provided a method for the prophylaxis and/or treatment of cognitive dysfunction, the method comprising the step of administering an agent comprising liver fluke homogenate (LFH) or a derivative product, or a mutant, fragment or variant of a protein or peptide isolated therefrom to an individual in need of such therapy.

A further aspect of the invention extends to the use of an agent comprising liver fluke homogenate (LFH) or a derivative product, or a mutant, fragment or variant of a protein or peptide isolated therefrom in the treatment of cognitive dysfunction.

A further still aspect relates to the use of liver fluke homogenate (LFH) or a derivative product, or a mutant, fragment or variant of a protein or peptide isolated therefrom in the preparation of a medicament for the treatment of cognitive dysfunction.

In a preferred embodiment, the administration of the LFH results in the up-regulation of anti-inflammatory cytokines, for example IL-4 and the down-regulation of pro-inflammatory cytokines such as IL-1. Preferably the upregulation will be in the hippocampus, most preferably this upregulation of the anti-inflammatory cytokine profile will be present in the microglia cells. It is preferred that LFH or ES be administered to the brain or directly to another area of the central nervous system (CNS).

Typically, the anti-inflammatory cytokines which are upregulated are IL-4, IL-10 and TGF-beta. The pro-inflammatory cytokines which are down-regulated are typically IL-1 beta and TNF-alpha. Preferably the modulation of pro-inflammatory and anti-inflammatory cytokine levels is in the hippocampus, most preferably this modulation of the cytokine profile is in the microglia cells.

A yet further aspect of the present invention provides a method of treating cognitive dysfunction through direct administration of liver fluke homogenate (LFH) or a derivative product, or a mutant, fragment or variant of a protein or peptide isolated therefrom to the brain or CNS.

A further still aspect relates to the use of liver fluke homogenate (LFH) or a derivative product, or a mutant, fragment or variant of a protein or peptide isolated therefrom in the preparation of a medicament for the treatment of cognitive dysfunction wherein the medicament is administered directly to the brain or CNS.

A further still aspect relates to the use of liver fluke homogenate (LFH) or a derivative product, or a mutant, fragment or variant of a protein or peptide isolated therefrom in the preparation of a medicament for the treatment of an immune mediated condition.

Toll-Like Receptor (TLR) Agonist

The present inventors have surprisingly identified that a TLR agonist is present in the ES (excretory/secretory) component of *Fasciola hepatica*. This TLR agonist may have important utility as an adjuvant in the induction of an immune response.

The TLR agonist could, for example, be administered along with a therapeutic, such as a vaccine for the treatment of a cancer or a malignant condition, or along with a vaccine directed to an infectious disease.

In further aspects, the present invention extends to the use of the TLR agonist identified within the ES (excretory/secretory) component of *Fasciola hepatica* in a method for inducing the maturation of dendritic cells.

Accordingly a yet further aspect of the present invention provides a method for inducing a Th1 response in a subject suitable for the treatment of cancer or an infectious disease, the method comprising the steps of:

exposing isolated dendritic cells to a disease specific antigen in the presence of a vaccine and a TLR agonist isolated from the ES (excretory/secretory) component of *Fasciola hepatica* ex-vivo in order to cause maturation of the dendritic cells to a phenotype that promotes effector cell function, and administering the dendritic cells to the subject;

whereby the immune response generated in the subject is sufficient to prevent the onset or progression of cancer or to prevent infection with a pathogenic micro-organism and thereby prevent an infectious disease.

DEFINITIONS

As used herein, the term "immune cell" includes cells that are of haematopoietic origin and play a role in the immune response. Immune cells include lymphocytes, such as B cells and T cells, natural killer cells, myeloid cells, such as monocytes, macrophages, eosinophils, mast cells, basophils, and granulocytes.

As used herein, the term "T cell" includes $CD4^+$ T cells and $CD8^+$ T cells. The term "T cell" also includes both T helper 1 type T cells and T helper 2 type T cells and also Th-IL17 cells.

As used herein, the term "antigen-presenting cell" or "antigen-presenting cells" or its abbreviation "APC" or "APCs" refers to a cell or cells capable of endocytotic adsorption, processing and presenting of an antigen. The term includes professional antigen presenting cells, for example, B lymphocytes, monocytes, dendritic cells (DCs) and Langerhans cells, as well as other antigen presenting cells such as keratinocytes, endothelial cells, glial cells, fibroblasts and oligodendrocytes. The term "antigen presenting" means the display of antigens as peptide fragments bound to MHC molecules on the cell surface. Many different kinds of cells may function as APCs including, for example, macrophages, B cells, follicular dendritic cells and dendritic cells.

As used herein, the term "immune response" includes T cell mediated and/or B cell mediated immune responses that are influenced by modulation of T cell co-stimulation. The term immune response further includes immune responses that are indirectly effected by T cell activation such as antibody production (humoral responses) and the activation of cytokine responsive cells such as macrophages.

As used herein, the term "dendritic cell" or "dendritic cells" (DC) refers to a dendritic cell or cells in its broadest context and includes any DC that is capable of antigen presentation. The term includes all DC that initiate an immune response and/or present an antigen to T lymphocytes and/or provide T-cells with any other activation signal required for stimulation of an immune response. Reference herein to "DC" should be read as including reference to cells exhibiting dendritic cell morphology, phenotype or functional activity and to mutants or variants thereof. The morphological features of dendritic cells may include, but are not limited to, long cytoplasmic processes or large cells with multiple fine dendrites. Phenotypic characteristics may include, but are not limited to, expression of one or more of MHC class I molecules, MHC class II molecules, CD1 or CD4.

As used herein, the term "antigen" is any organic or inorganic molecule capable of stimulating an immune response. The term "antigen" as used herein extends to any molecule such as, but not limited to, a peptide, polypeptide, protein, nucleic acid molecule, carbohydrate molecule, organic or inorganic molecule capable of stimulating an immune response.

A "subject" in the context of the present invention includes and encompasses mammals such as humans, primates and livestock animals (e.g. sheep, pigs, cattle, horses and donkeys), laboratory test animals such as mice, rabbits, rats and guinea pigs, and companion animals such as dogs and cats. It is preferred for the purposes of the present invention that the mammal is a human.

Treatment

The term 'treatment' is used herein to refer to any regimen that can benefit a human or non-human mammal. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

Administration

The excretory/secretory (ES) component from *Fasciola hepatica* or a derivative product, or a mutant, fragment or variant of a protein or peptide isolated therefrom for use in the present invention may be administered alone but will preferably be administered as a pharmaceutical composition, which will generally comprise a suitable pharmaceutical excipient, diluent or carrier selected depending on the intended route of administration.

The excretory/secretory (ES) component from *Fasciola hepatica* or a derivative product, or a mutant, fragment or variant of a protein or peptide isolated therefrom for use in the present invention may be administered to a patient in need of treatment via any suitable route. The precise dose will depend upon a number of factors, including the precise nature of the form of the excretory/secretory (ES) component from *Fasciola hepatica* or a derivative product, or a mutant, fragment or variant of a protein or peptide isolated therefrom to be administered.

Although the preferred route of administration is parenterally (including subcutaneous, intramuscular, intravenous), some further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example, a nebuliser or inhaler, or by an implant.

For intravenous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or Lactated Ringer's injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982).

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. $7^{th}$ Edition ISBN 0-683305-72-7, the entire disclosures of which are herein incorporated by reference.

Pharmaceutical Compositions

As described above, the present invention extends to a pharmaceutical composition for the modulation of an immune response and in particular the down regulation of a T cell response wherein the composition comprises at least the excretory/secretory (ES) component from *Fasciola hepatica* or a derivative product, or a mutant, fragment or variant of a protein or peptide isolated therefrom, or a derivative, fragment, variant, mutant or recombinant version thereof.

Pharmaceutical compositions according to the present invention, and for use in accordance with the present invention, may comprise, in addition to active ingredient (i.e. the excretory/secretory (ES) component from *Fasciola hepatica* or a derivative product, or a mutant, fragment or variant of a protein or peptide isolated therefrom), a pharmaceutically acceptable excipient, carrier, buffer stabiliser or other materials well known to those skilled in the art.

Such materials should be non-toxic and should not interfere with the efficacy of the active ingredient. The precise nature of the carrier or other material will depend on the route of administration, which may be, for example, oral, intravenous, intranasal or via oral or nasal inhalation.

The formulation may be a liquid, for example, a physiologic salt solution containing non-phosphate buffer at pH 6.8-7.6, or a lyophilised or freeze dried powder.

Dose

The composition is preferably administered to an individual in a therapeutically "effective amount" or a "desired amount", this being sufficient to show benefit to the individual.

As defined herein, the term an "effective amount" means an amount necessary to at least partly obtain the desired response, or to delay the onset or inhibit progression or halt altogether the onset or progression of a particular condition being treated.

The amount varies depending upon the health and physical condition of the subject being treated, the taxonomic group of the subject being treated, the degree of protection desired, the formulation of the composition, the assessment of the medical situation and other relevant factors. It is expected that the amount will fall in a relatively broad range, which may be determined through routine trials.

Prescription of treatment, e.g. decisions on dosage etc, is ultimately within the responsibility and at the discretion of general practitioners, physicians or other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration.

A broad range of doses may be applicable. Considering a patient, for example, from about 0.1 mg to about 1 mg of agent may be administered per kilogram of body weight per day. Dosage regimes may be adjusted to provide the optimum therapeutic response. For example, several divided doses may be administered daily, weekly, monthly or at other suitable time intervals or the dose may be proportionally reduced as indicated by the exigencies of the situation.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, the term "inhibits" when used in relation to the modulation of the T cell response means the partial or complete down-regulation of proliferation and/or activity of the T cells.

Preferred features and embodiments of each aspect of the invention are as for each of the other aspects mutatis mutandis unless the context demands otherwise.

The present invention will now be described with reference to the following examples which are provided for the purpose of illustration and are not intended to be construed as being limiting on the present invention, and further, with reference to the figures.

BRIEF DESCRIPTION OF THE DRAWINGS

FIG. 1 represents cells that were gated on the CD11c$^+$ DC population, FIG. 2 shows IL-10 and IFN-gamma production by CD11c$^+$ DC. Numbers represent percentages of gated CD11c$^+$ cells, FIG. 4 shows a representative example of FOXP3 and CD25 expression on CD4$^+$ T cells in MLN and PEC from naïve and $F.$ hepatica infected mice on day 21 post challenge. Numbers represent percentages of gated cells, FIG. 5 shows cell surface marker expression on T-cells.

FIG. 10 expresses the means (±SE) cytokine concentrations for triplicate cultures.

FIG. 11 expresses the mean (±SE) cytokine concentrations for triplicate cultures.

FIG. 12 shows mean (±SE) cytokine concentrations for triplicate cultures.

FIG. 13 shows mean (±SE) cytokine concentrations for triplicate cultures.

FIG. 14 shows cytokine production in PEC DC from PBS- and ES-injected mice. Numbers represent percentages of gated CD11c$^+$ cells.

FIG. 15 shows mean (±SE) cytokine concentrations for triplicate cultures.

FIG. 16 shows mean (±SE) IL-12 p70 and IL-10 concentrations for triplicate cultures.

FIG. 17 shows mean (±SE) cytokine concentrations for triplicate cultures.

FIG. 18 shows mean (±SE) cytokine concentrations for triplicate cultures.

FIG. 19 shows mean (±SE) cytokine concentrations for triplicate cultures.

FIG. 23 shows the mean (±SE) of four mice per group.

FIG. 24 shows the mean (±SE) of four mice per group.

FIG. 25 shows mean (±SE) cytokine concentrations and proliferation counts for triplicate cultures.

FIG. 26 shows average clinical EAE scores and disease index.

FIG. 27 shows mean values for groups of 4-5 mice tested in triplicate.

FIG. 28 shows average clinical EAE scores.

FIG. 29 shows mean values for groups of 6 mice tested in triplicate.

FIG. 30 shows mean scores for 6-8 mice per group.

FIG. 32 shows mean scores for 6-8 mice per group.

FIG. 33 shows that the induction of IL-1β, IL-17 and IL-10 in the colon during DSS-induced colitis is reduced by administration of *Fasciola hepatica* ES products.

FIG. 34 shows the mean (±SE) of four mice per group.

EXAMPLES

Material and Methods

Animals and Immunisation

Figure 1A:
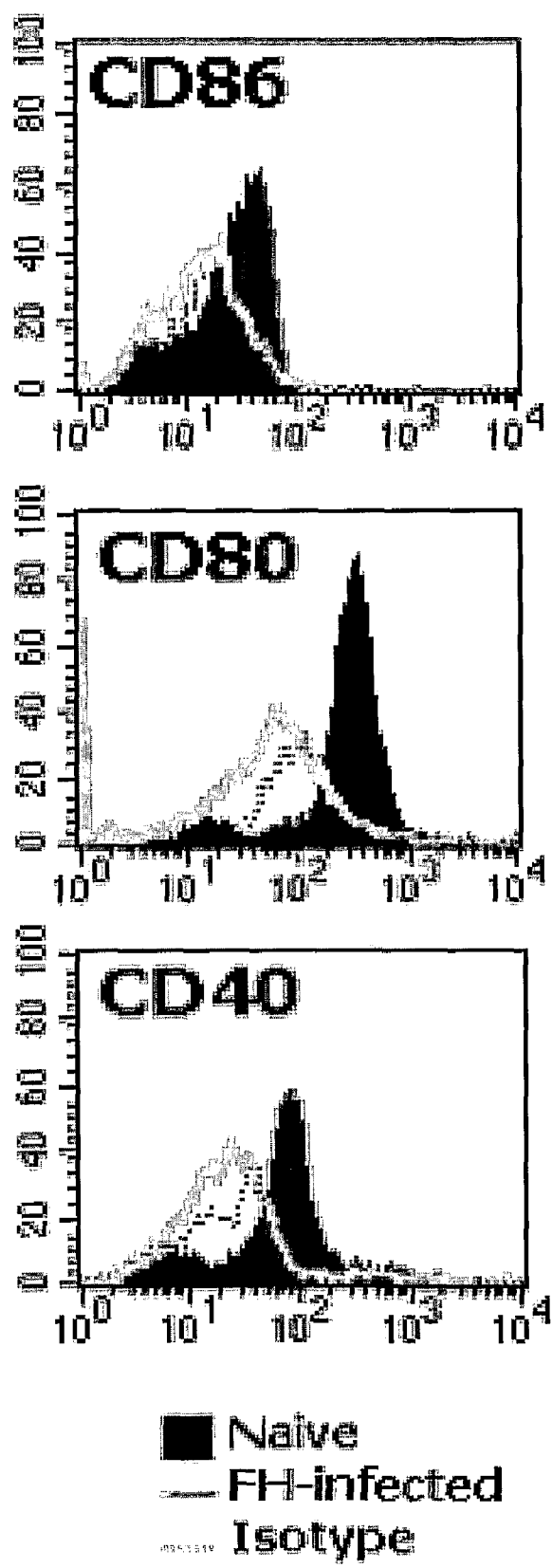
FIG. 1 shows that $F.$ hepatica infection modulates dendritic cell (DC) maturation. BALB/c Mice were infected orally with Fasciola hepatica. Three weeks post-infection peritoneal exudate cells were isolated from naïve and $F.$ hepatica-infected mice by lavage, and stained for cytofluorometric analysis with antibodies (Abs) specific for CD11c, CD80, CD86, CD40, CCR5 and MHC Class II or species- and isotype-matched control Abs.

Female BALB/c mice were purchased from Harlan Olac (Bicester, United Kingdom) and used at 6 to 8 weeks old, with four mice per group. Mice were housed in individually ventilated cages and all experiments were performed according to regulations of the Irish Department of Health, the European Union and the Ethics Committee of Trinity College Dublin. Mice were immunized subcutaneously (s.c.) in the flank with depyrogenated keyhole limpet hemocyanin (KLH) (5 μg; Calbiochem, La Jolla, Calif.); KLH (5 μg) with ES (20 or 50 μg; or with Dulbecco's PBS (Sigma, Poole, United Kingdom) in a final volume of 200 μl. Seven days after immunization, mice were sacrificed by cervical dislocation, and serum and inguinal lymph nodes were collected Preparation of Excretory-Secretory Products from *F. hepatica*

Live, adult flukes were collected from bovine livers at a local abattoir. Flukes were washed in several changes of $Ca^{2+}$- and $Mg^{2+}$-free Dulbeccos PBS, and then incubated overnight in PBS, at 37° C. in 5% $CO_2$ in air. Supernatant fluid containing excretory-secretory (ES) products was harvested, clarified by centrifugation at 13,000 g for 15 mins at 4° C. and passed through a 0.22 μm filter. The protein concentration of the ES preparation was determined using a bicinchoninic acid protein kit (Pierce). Antigen preparations were stored at −80° C. until required.

Infection of Mice with *F. hepatica*

Metacercariae were obtained from Compton Paddock Laboratories (Berkshire, UK). Viability was examined using a stereomicroscope before orally infecting mice with 10 metacercariae of *F. hepatica*. This resulted in infection in 100% of animals. Mice were sacrificed by cervical dislocation 3 weeks after infection, unless otherwise stated.

Isolation and Culture of Bone Marrow-Derived DC (BMDC)

Bone marrow-derived immature DC were prepared by culturing bone marrow cells obtained from the femurs of mice in RPMI 1640 medium with 10% FCS supplemented with supernatant (10%) from a GM-CSF-expressing cell line (J558-GM-CSF). On day 3, fresh medium with 10% GM-CSF cell supernatant was added to adherent cells. On day 7, cells were collected, washed, and used for assays. BMDC were cultured at $1 \times 10^6$ cells/ml.

Purification of Peritoneal Macrophages, $CD11c^+$ DC and $CD4^+$ T-Cells

For isolation of peritoneal macrophages, peritoneal exudate cells (PEC) were harvested from mice by lavage. PEC were incubated in 6-well tissue culture plates for 2 hrs to allow plastic adherence of macrophages. Non-adherent cells were removed by washing and adherent macrophages were harvested from the plates for stimulation. $CD4^+$ T-cells or $CD11c^+$ dendritic cells were isolated from spleen and PEC using positive selection with MACS microbeads (Miltenyi Biotec, Bergisch Gladbach, Germany) and an autoMACS cell sorting instrument. Following lysis of red blood cells, single cell suspensions of either PEC or spleen cells were incubated with either MACS CD4 or CD11c immunomagnetic beads (Miltenyi Biotec), and allowed to pass through the autoMACS using positive selection. The purity of $CD4^+$ T-cells and $CD11c^+$ dendritic cells after autoMACS separation were routinely 90-95% as estimated by FACScan analysis using FITC-conjugated CD4 or CD11c respectively.

J774 Cell Culture

J774.A1 cells (ATCC number TIB 67), were grown in tissue culture flasks at 37° C. in 5% $CO_2$ in air with RPMI 1640 medium containing 10% foetal calf serum (FCS). When cells reached confluence, they were removed from culture, centrifuged at 1200 rpm for 5 mins to pellet cells, and reseeded in fresh flasks at a concentration of $1 \times 10^6$/ml. When cells reached sufficient numbers for experiments, cells were then collected by vigorous pipetting and were centrifuged at 1200 rpm for 5 mins. The cells were washed once with 10% RPMI and then seeded into 24-well culture plates at $1 \times 10^6$/ml at a volume of 1 ml/well for stimulations.

Induction or Inhibition of Cytokine Production

J774 and peritoneal macrophages, bone marrow-derived DC, MACS-isolated $CD11c^+$ DC and peritoneal exudate cells were cultured 24-well tissue culture plates at a cell density of $1 \times 10^6$/ml. In some experiments, peritoneal exudate cells and J774 macrophages were also stimulated with ES in the presence of the cathepsin inhibitor E-64 (Sigma) at a concentration of 10 mM, or with heat-inactivated ES, which was heated to 100° C. for 20 mins. Following incubation for 24 hrs at 37° C. in 5% $CO_2$ in air, supernatants were removed and stored until analysis of IL-10, IL-12p40 concentrations using commercially available immunoassay kits (R&D systems), or pairs of monoclonal antibodies (Pharmingen) for IL-4 and IL-5, IL-12p70 and TGF-β. The effect of ES on IL-12 production was determined by pre-stimulating BMDC or J774 macrophages ($1 \times 10^6$/ml) for 2 hrs with ES (4 and 20 μg/ml), followed by addition of LPS (10 ng/ml) and IFN-γ (20 ng/ml), or LPS only, and incubation for a further 22 hrs. Supernatants were removed and concentrations of IL-10, IL-12 p40 and/or IL-12 p70 determined by immunoassay. The effect of ES on Con A-induced cytokine production and proliferation was determined by stimulating spleen cells ($2 \times 10^6$/ml) from naïve mice with ES (4 and 20 μg/ml) in the presence or absence of Con A (5 μg/ml). Supernatants were removed following incubation for 72 hrs, at 37° C. in 5% $CO_2$ in air, and T-cell cytokine concentrations determined by ELISA. Proliferation of T-cells was measured by [$^3$H] thymidine incorporation over the last 4 hrs of a 48 hr culture. To assess cytokine induction by ES in vivo, BALB/c mice were injected s.c. in the flank with 50 μg ES in a total volume of 200 μl/mouse. Six hours later, inguinal nodes were removed and homogenized in 1 ml ice cold PBS. After removal of cells by centrifugation at 1200 rpm for 5 mins at 4° C., supernatants were removed and analyzed for the presence of IL-4 and IL-10 using commercially available cytokine DuoSets (R&D). In a separate experiment, groups of 4 BALB/c mice were injected with 300 µl of either PBS or ES (50 µg). After 2 hours, peritoneal exudate cells (PEC) from PBS- and ES-injected mice were harvested by peritoneal lavage in ice-cold PBS. Cells were blocked with 50% PBS/FCS (v/v) and surface labelled with anti-CD11c, before fixing and permeabilising for intracellular cytokine labelling by adding PE-labelled anti-IL-10, and FITC-labelled anti-IL-4 and anti-IFN-γ monoclonal antibodies, or rat control Ig. After 30 mins on ice, cells were then washed with PBS/BSA/azide and acquired immediately. A total of 20,000 cells were acquired per sample. Cells were gated on the CD11c$^+$ population, and the expression of intracellular proteins was analyzed on a FACSCalibur flow cytometer using CellQuest software.

Suppression Assay

CD4$^+$ T cells were purified from OVA-specific TCR transgenic (TCR-Tg) mice using MACS microbeads and the AutoMacs system (described above). OVA-specific T-cells ($1\times10^5$/ml) were cultured with OVA$_{323-339}$ peptide (2 µg/ml), and irradiated spleen cells ($2\times10^6$/ml) as antigen presenting cells (APC). This OVA-specific response served as the control. *F. hepatica*-specific T-cells (FH T-cells) were isolated from peritoneal lavage fluid of infected mice 3 weeks after infection using CD4$^+$ MACS microbeads (as above). FH T-cells were then cultured either without any antigen or APC, or with liver fluke homogenate (LFH) at 20 µg/ml, or ES (20 µg/ml), together with irradiated spleen cells from naïve BALB/c mice as APC. OVA-specific and FH T-cells were then cultured together in a 1:1 ratio, either in the same well or separated by a semi-permeable membrane (transwell). After 72 hrs incubation at 37° C. in 5% CO$_2$ in air, supernatants were removed from above and below the transwell, and from the co-cultured cells for determination of IL-4, IL-5, IL-10 and IFN-γ levels by ELISA. Proliferation was determined by $^3$H-thymidine incorporation after 96 hrs culture.

Analysis of Innate Cell Activation by FACS

BMDC or J774 macrophages ($1\times10^6$/ml) were cultured in medium only, ES (20 µg/ml) or *E. coli* LPS (10 ng/ml). Cells were recovered, and surface marker expression was assessed by flow cytometry using fluorescently labeled antibodies (BD Pharmingen). After blocking with 50% FCS/PBS (w/v), cells were incubated for 30 mins on ice in the dark with antibodies specific for mouse CD80, CD86, CD11c (for BMDC only), MHC Class II, CD40 and CCR5. Cells labeled with appropriate isotype matched antibodies with irrelevant specificity acted as controls. A total of 20,000 cells per sample were analyzed on a FACScalibur flow cytometer. Analysis was performed using CellQuest software (version 3.3; Becton Dickinson Immunocytometry Systems, San Jose, Calif.).

Modulation of J774 Surface Marker Expression

The effect of ES on LPS-induced cell surface marker expression was determined by pre-stimulating J774 macrophages ($1\times10^6$/ml) for 2 hrs with ES (20 µg/ml), followed by addition of LPS (10 ng/ml), and incubation for a further 22 hrs. After 24 h cells were recovered, washed and blocked, and expression of surface markers were assessed using CD86, CD80, CD40, CCR5 and MHC Class II. Cells incubated with an isotype-matched directly conjugated Ab with irrelevant specificity acted as a control. After incubation for 30 mins on ice in the dark, cells were washed and immunofluorescence analysis was performed on a FACScan (Becton Dickinson) and analyzed using CellQuest software; 20,000 cells were analyzed per sample.

Flow Cytometric Analysis of Intracellular Cytokine Synthesis

To analyse cytokine production in DC and T-cells from *F. hepatica*-infected mice, peritoneal exudate cells (PEC) were first incubated with 50% PBS/FCS (v/v) for 20 mins at room temperature. DC and T-cell were then stained with anti-CD11c and anti-CD4 respectively. For detection of intracellular IL-10, IL-4 and IFN-γ, cells were fixed and permeabilised using a commercially available intracellular cytokine staining kit (Caltag). PE-conjugated anti-IL-10, and FITC-conjugated IL-4, IFN-γ mAb or rat control Ig were added at a predetermined saturating concentration for 30 min. Cells were then washed with PBS/BSA/azide and acquired immediately. A total of 50,000 cells were acquired per sample. Cells were gated on CD11c or CD4 for DC and T-cells respectively, and the expression of intracellular proteins was analyzed on a FACSCalibur flow cytometer using CellQuest software.

Antigen-Specific Cytokine Production

Spleen ($2\times10^6$/ml) or lymph node cells ($1\times10^6$/ml) from immunized mice or infected mice were cultured at 37° C. and 5% CO2 in RPMI medium with either MOG peptide (10 and 100 µg/ml) or KLH (2 to 50 µg/ml) or phorbol 12-myristate 13-acetate (PMA) (25 ng/ml; Sigma) and anti-CD3 (0.5 µg/ml; BD Pharmingen, San Diego, Calif.) or medium only. After 72 hrs, supernatants were collected for cytokine detection and the medium was replaced. Proliferation was assessed by [$^3$H]thymidine incorporation. Concentrations of IL-4, IL-5, IL-10 and IFN-γ were determined by immunoassay.

Induction of EAE and ES Treatment

Mice were each injected s.c. with 150 µg of MOG35-55 peptide in CFA containing 5 mg/ml *Mycobacterium tuberculosis* H37Ra (Difco) in the base of the tail. All mice received 500 ng of pertussis toxin (Sigma) by i.p. injection on days 0 and +2 post-immunization. For treatment with ES, 50 µg of ES in PBS was injected i.p. every second day. Mice were assessed daily for clinical signs of EAE, and scored as follows: 1=tail paralysis, 2=wobbly gait, 3=hind limb weakness, 4=hind limb paralysis, 5=complete paralysis of hind and fore limbs, 6=death. The disease index was calculated by adding all daily average disease scores, dividing the average day of onset, and multiplying by 100. Experiments were terminated when control EAE mice displayed clinical scores of 3-4. Mice were sacrificed by cervical dislocation, and serum and spleens were harvested.

EAE was induced in C57BU6 mice by immunization with MOG35-55 peptide in CFA on day 0 and injection of pertussis toxin days 0 and 2. One group of mice was left untreated. A second group was infected with 10 metacercariae of *F. hepatica* one day before induction of EAE. A third was injected i.p. with 50 µg ES, one day before induction of EAE and every second day thereafter. 20 days after induction of EAE, mice were sacrificed and spleen removed. Spleen cells ($2\times10^6$/ml) were stimulated with medium only, MOG35-55 peptide (10 and 100 µg/ml), or anti-CD3 and PMA. Supernatants were removed after 3 days and IL-17, IFN-γ, IL-4 and IL-10 concentrations determined by ELISA. Results are mean values for groups of 4-5 mice tested in triplicate.

Results

Infection with *F. hepatica* Inhibits Dendritic Cell Maturation

Figure 1B:
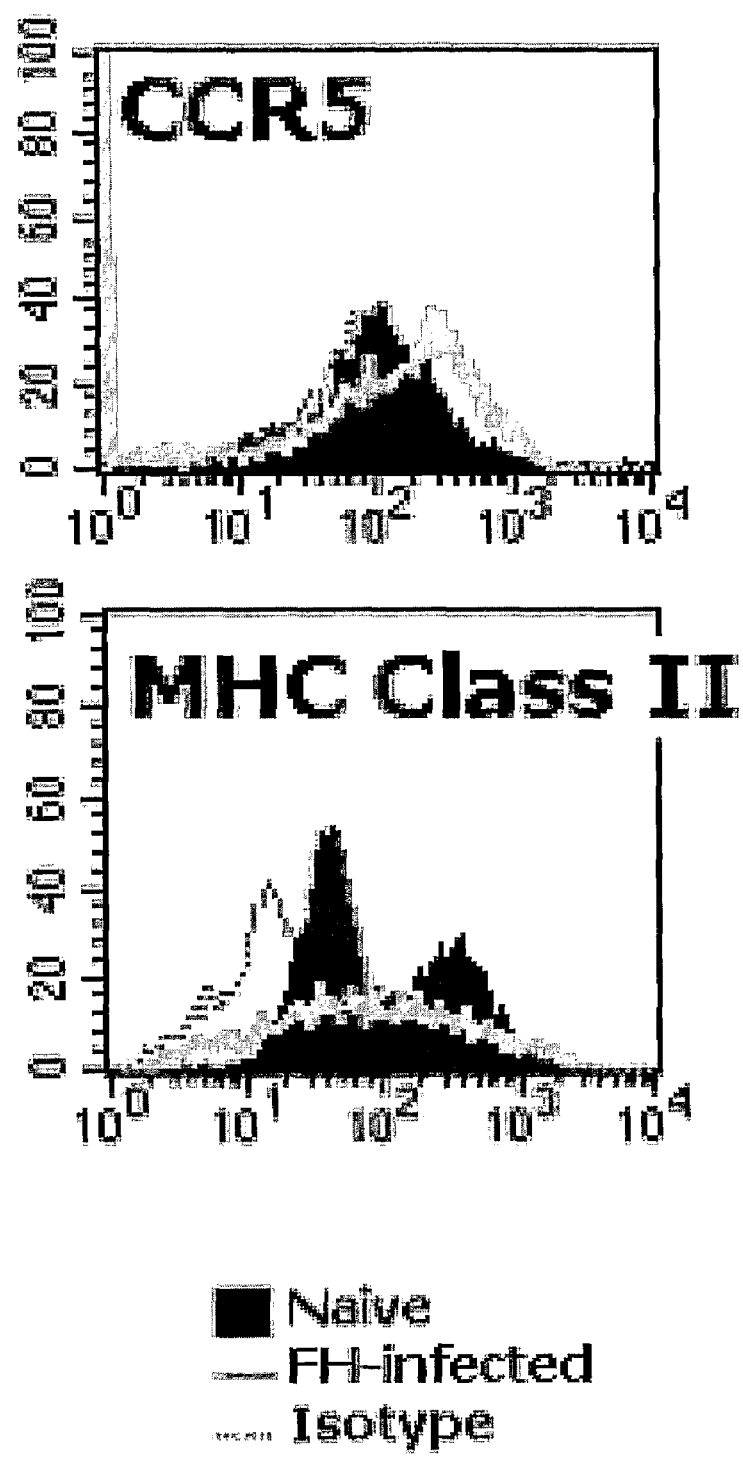

Following oral infection with *F. hepatica* metacercariae, the parasites migrate from the gut through the peritoneal cavity to the liver. Therefore the peritoneal cavity is exposed to products of the liver fluke. Here we examined the influence of a *F. hepatica* infection on cells of the innate immune response in the peritoneal cavity. Mice were infected with *F. hepatica* and 3 weeks after infection, cells were recovered from the peritoneal cavity. Cells from naïve mice served as controls. Dendritic cells (DC) were examined for expression of cells surface markers indicative of maturation. In comparison with cells from control mice, DC from *F. hepatica* had significantly lower expression of MHC class II and the co-stimulatory molecules, CD80, CD86 and CD40 and higher expression of CCR5 (FIG. 1). This suggests that infection inhibits DC maturation or recruits immature DC into the peritoneal cavity.

A High Frequency of Dendritic Cells from the Peritoneal Cavity of *F. hepatica* Infected Mice Secrete IL-10 and a Lower Frequency Secrete IL-4

Figure 2:
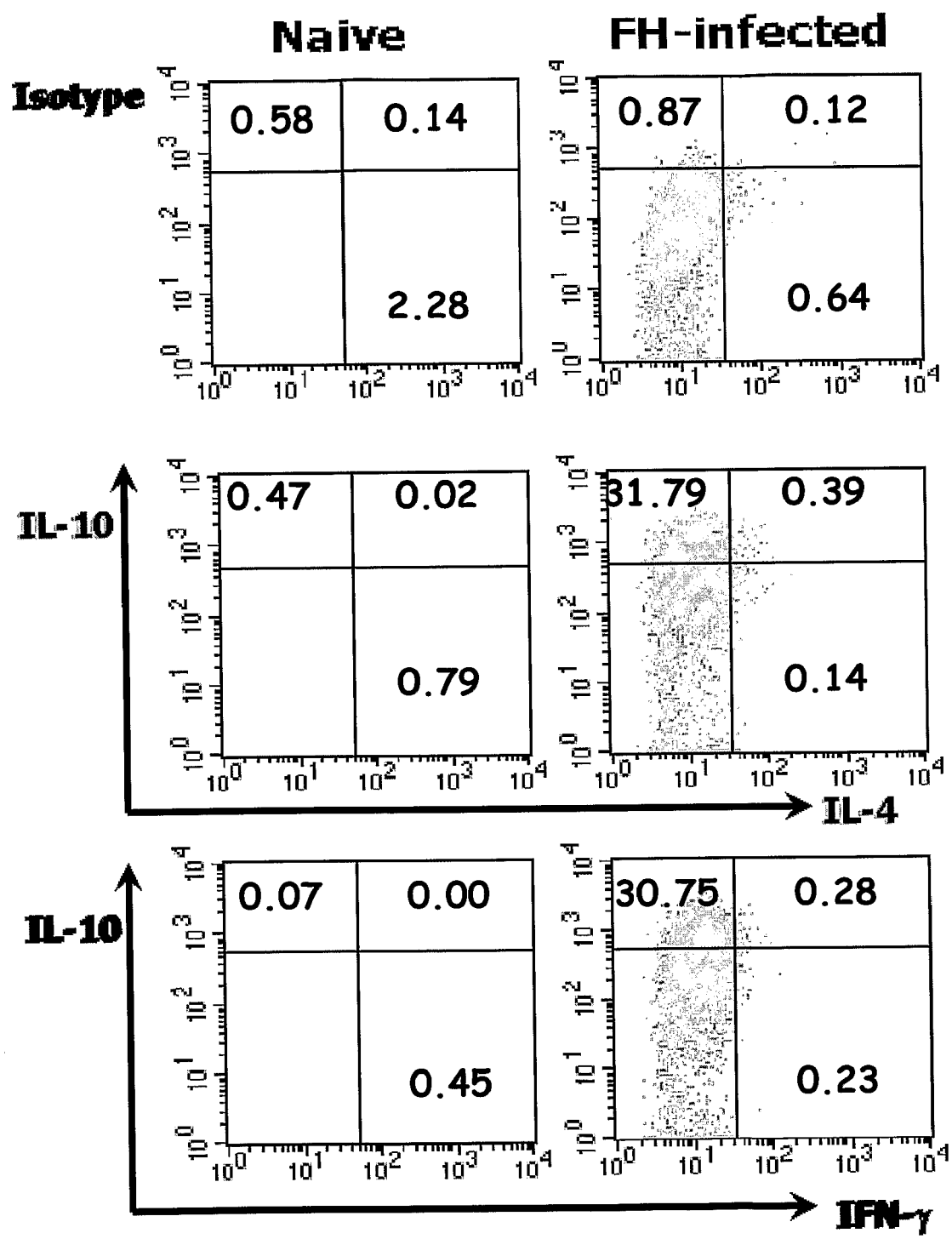
FIG. 2 shows that $F.$ hepatica infection induces IL-10-producing dendritic cells. Peritoneal exudate cells (PEC) were harvested by peritoneal lavage from naïve and $F.$ hepatica-infected BALB/c mice 21 days post challenge. Cells were blocked and surface labelled with anti-CD11c before fixing and permeabilising for intracellular cytokine labelling by fluorescently labelled anti-IL-10, anti-IL-4 and anti-IFN-gamma antibodies. Cells were then analysed using a flow cytometer and gated for the CD11c$^+$ cell population.

Mice were infected with *F. hepatica* and 3 weeks after infection, cells were recovered from the peritoneal cavity. Cells from naïve mice served as controls. CD11c$^+$ DC were examined for intracellular IL-4, IL-10 and IFN-γ by immunofluorescence analysis (FIG. 2). Compared with DC from the peritoneal cavity of naïve mice, a high frequency of DC from *F. hepatica* infected mice secreted IL-10 (34-35% in infected versus 2-3% in naive). There was also a small increase in the frequency of DC secreting IL-4 (2.26% in infected versus 0.37% in naïve) and IFN-γ (1.57% in infected versus 0.48% in naïve).

Figure 3:
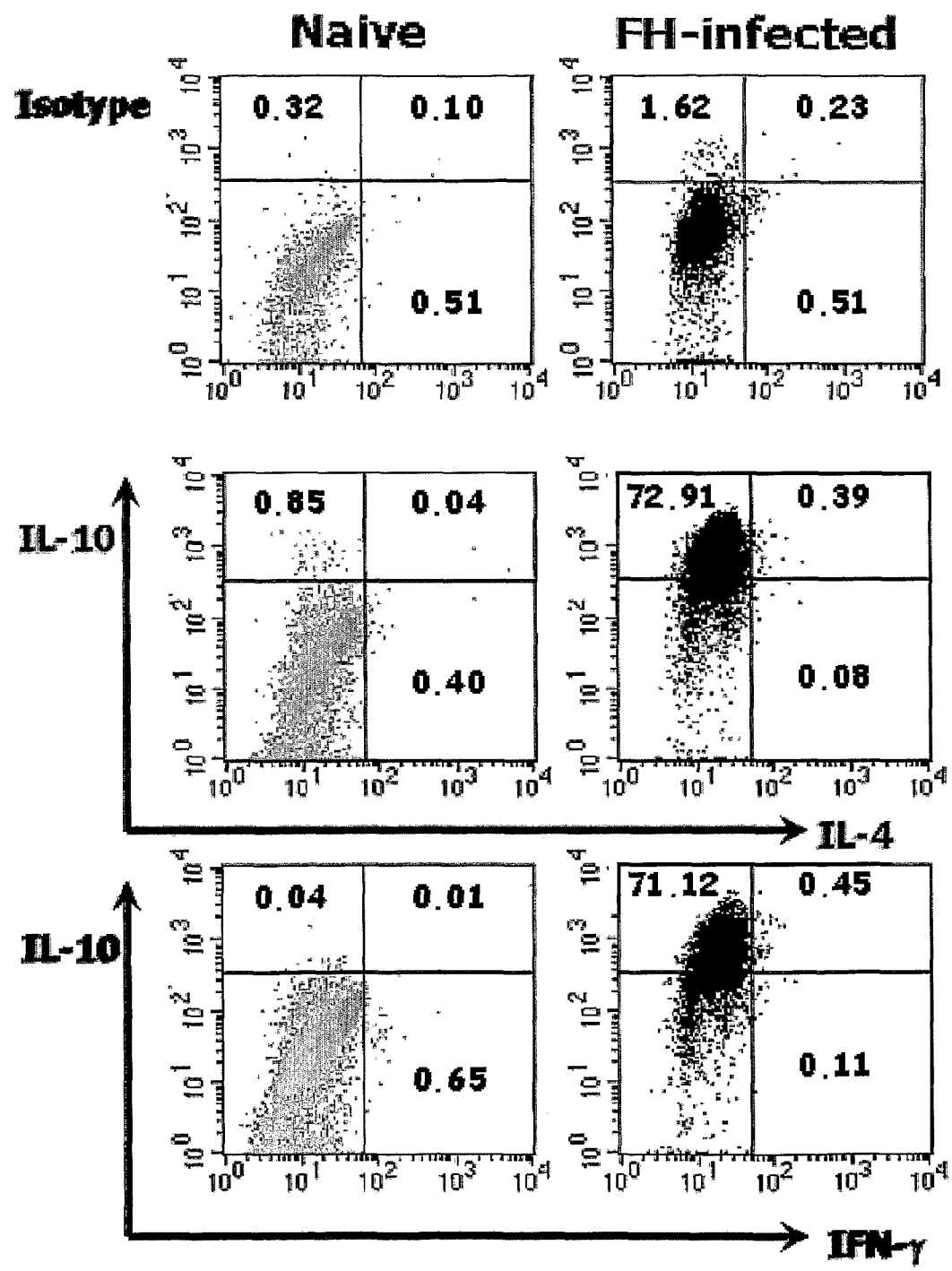
FIG. 3 shows that infection with $F.$ hepatica induces IL-10-secreting T-cells. Peritoneal exudate cells (PEC) from naïve and $F.$ hepatica-infected BALB/c mice were harvested by peritoneal lavage 21 days post challenge. Cells were blocked and surface labelled with anti-CD4 before fixing and permeabilising for intracellular cytokine labelling by fluorescently labelled anti-IL-10, anti-IL-4 and anti-IFN-gamma antibodies. Cells were then analysed using a flow cytometer and gated for the CD4$^+$ cell population. Numbers represent percentages of gated cells.

A High Frequency of IL-10 Secreting T Cells with a Regulatory Phenotype are Detected in the Peritoneal Cavity of *F. hepatica* Infected Mice Since IL-10-producing DC have been shown to promote the induction of IL-10-secreting regulatory T (Treg) cells, we examined the possibility that infection with *F. hepatica* was also associated with the induction of Treg cells. BALB/c mice were infected with *F. hepatica* and 3 weeks after infection, cells were recovered from the peritoneal cavity. Cells from naïve mice served as controls. CD4$^+$ T cells were examined for intracellular IL-4, IL-10 and IFN-γ by immunofluorescence analysis (FIG. 3). The results show that a high frequency of T cells in the peritoneal cavity of *F. hepatica* infected mice secrete IL-10 (66-67% in infected versus 3-5% in naïve). In contrast, the frequency of IL-4 and IFN-γ secreting T cells was not significantly enhanced.

Figure 5A:
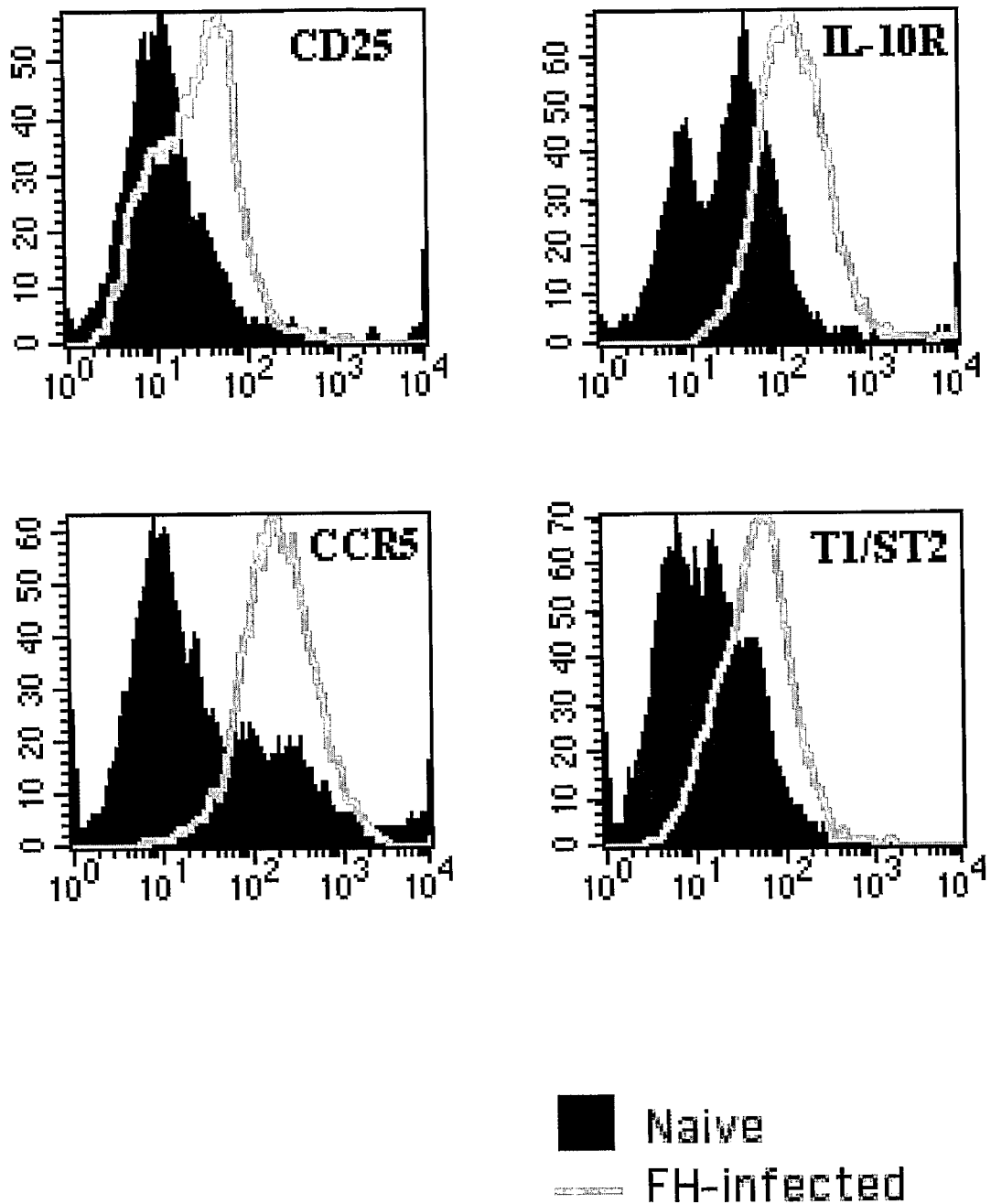
FIG. 5 shows that T-cells induced during $F.$ hepatica infection have a regulatory phenotype. T-cells were isolated from the peritoneal cavity of naïve and $F.$ hepatica-infected mice (21 days post challenge) using positive selection for CD4$^+$ cells by magnetic sorting. Cells were blocked and surface labelled with anti-CD4 and stained for cytofluorometric analysis for CD25, CCR5, CD28, CD45RB, CTLA-4, IL-10R and T1/ST2. Cells were then analysed using a flow cytometer and gated for the CD4$^+$ cell population.
Figure 5B:
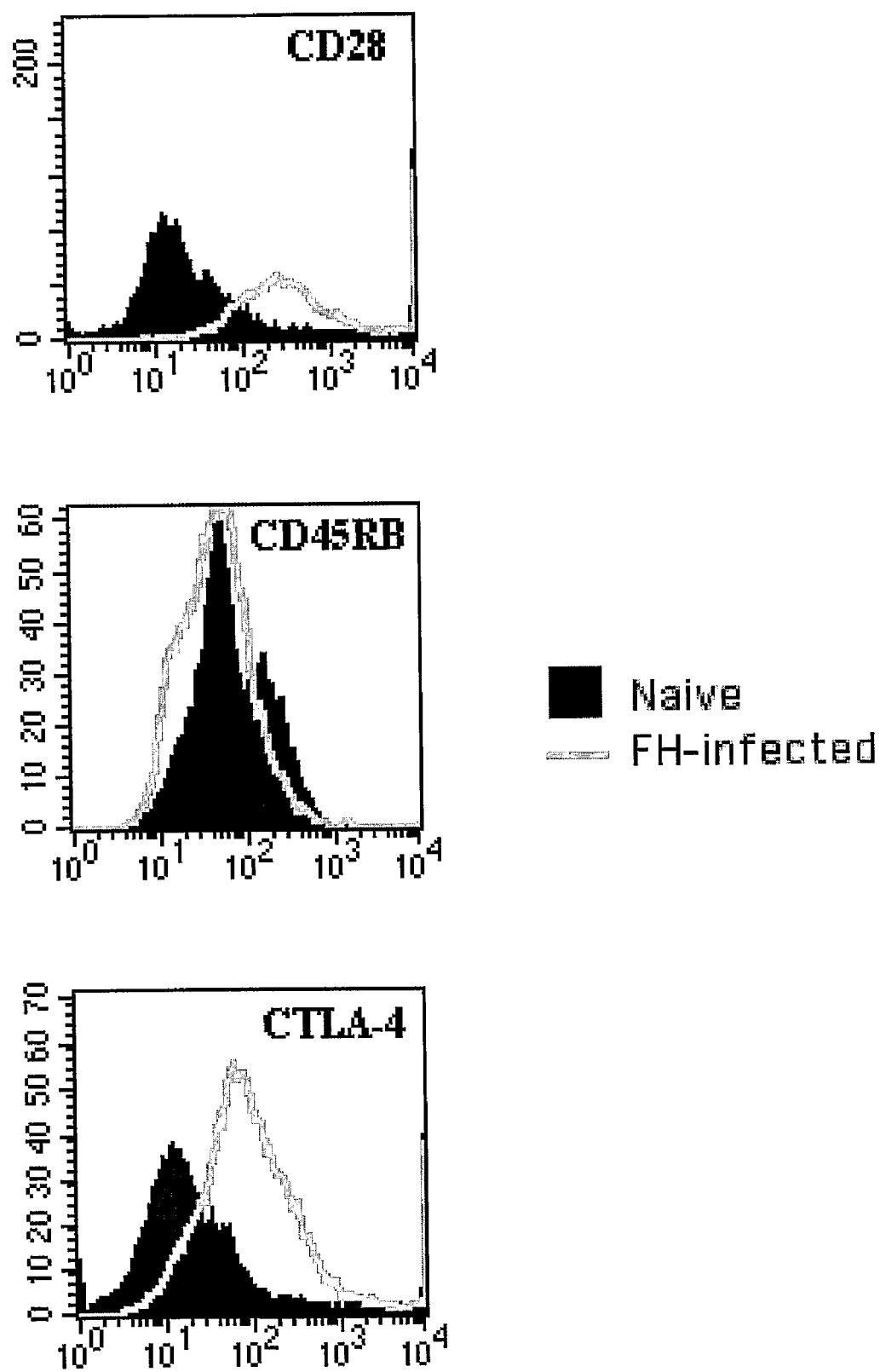

T cells from the peritoneal cavity were also assessed for surface expressions of surface markers know to be associated with Treg cells. Immunofluorescence analysis with specific antibodies revealed that expression of CTLA-4, IL-10R, CD28, T1/ST2, and CCR5 were enhanced on cells from *F. hepatica* infected mice (FIG. 5). In contrast, CD25 expression was lower. These findings suggest that inducible Treg cells are generated, or recruited to the peritoneal cavity during *F. hepatica* infection.

*Fasciola hepatica* Induces FOXP3-Expressing T-Cells

Figure 4:
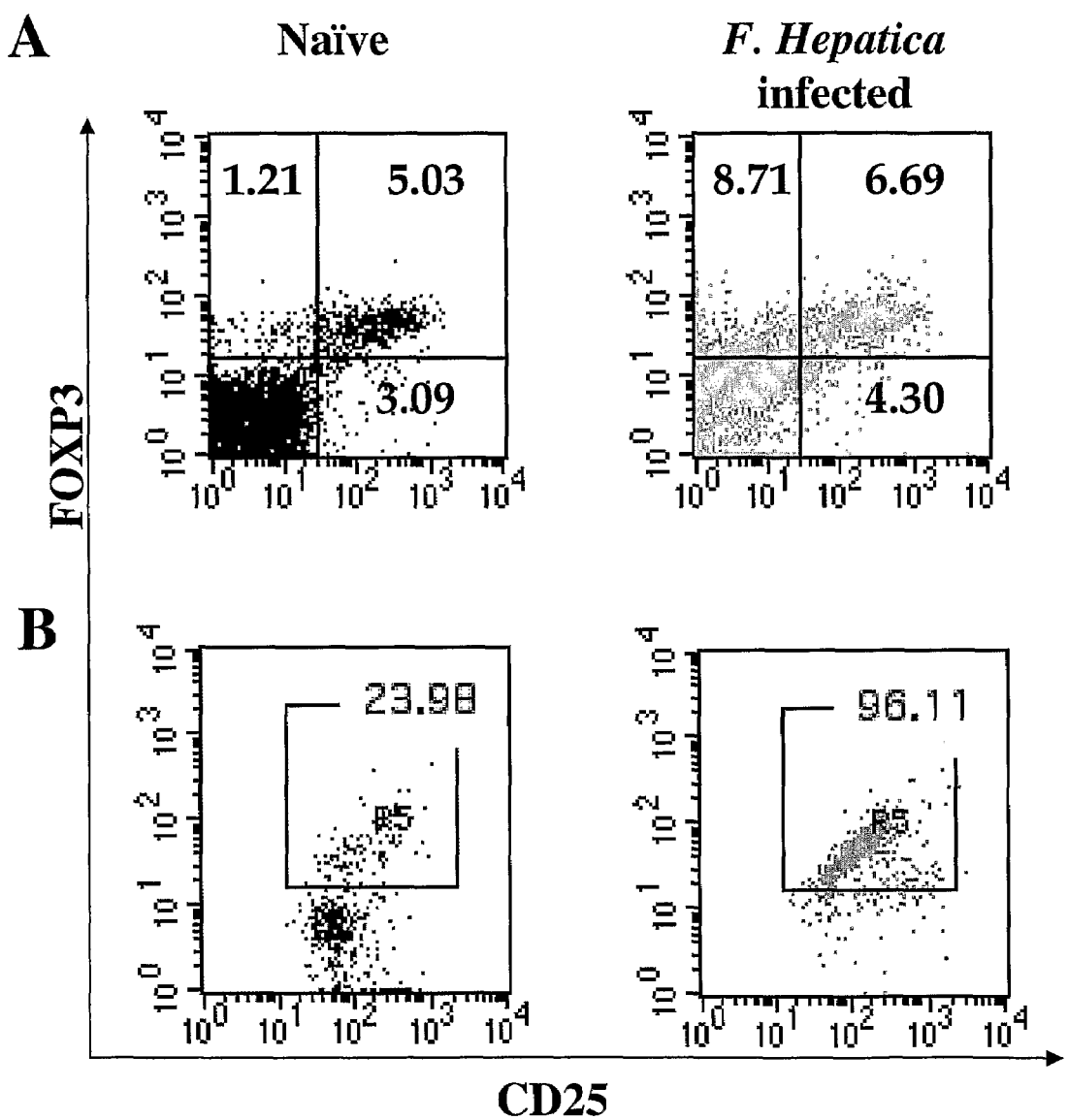
FIG. 4 shows that Fasciola hepatica induces FOXP3-expressing T-cells. Mesenteric lymph node (MLN) cells (A) and peritoneal exudate cells (PEC) (B) from naïve and $F.$ hepatica-infected mice were isolated 21 days after infection. Cells were blocked and surface labelled with anti-CD4 before fixing and permeabilising for intracellular staining for FOXP3. Cells were then analysed using a flow cytometer and gated for the CD4+ cell population.

FIG. 4 shows that infection with *F. hepatica* is associated with very significant recruitment to CD4$^+$ CD25$^+$Foxp3$^+$ regulatory T cells into the peritoneal cavity. There was a small increase in the number of regulatory T cells in the lymph nodes of infected mice (5% to 6.7%), whereas the frequency in the peritoneal cavity increased from 24% to 96% after *F. hepatica* infection.

Figure 6A:
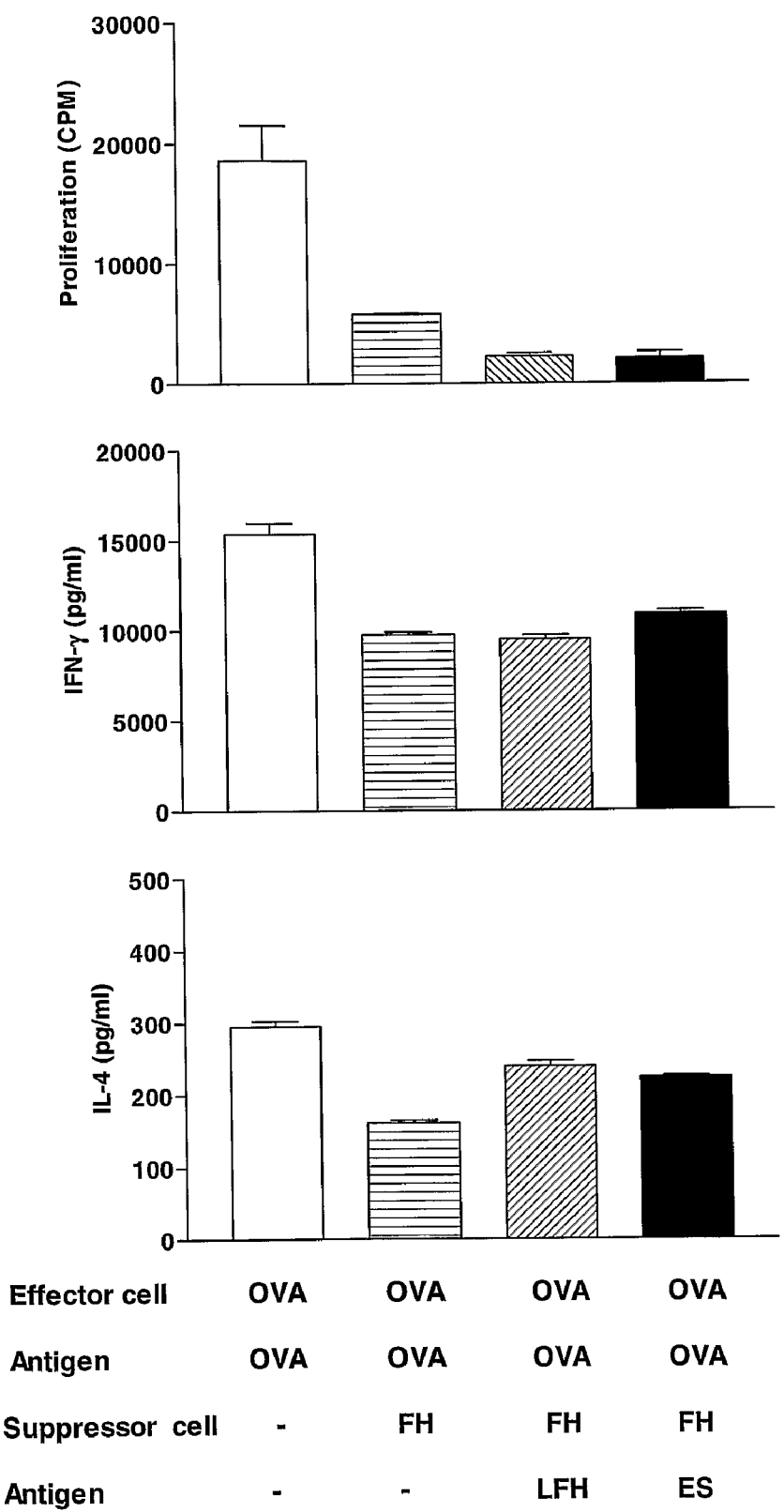
FIG. 6 shows that T-cells induced during $F.$ hepatica infection have suppressive capacity. CD4$^+$ T-cells were purified from the peritoneal cavity of $F.$ hepatica-infected mice 3 weeks post-infection. Purified CD4$^+$ T-cells from $F.$ hepatica-infected mice were cultured with ES (20 µg/ml) or LFH (20 µg/ml), together with irradiated spleen cells as antigen presenting cells (APC; 2×10$^6$/ml), alone or together with purified CD4$^+$ T-cells from DO11.10 Tg mice, with OVA peptide (2 µg/ml). OVA-specific T-cells and $F.$ hepatica-specific T-cells were cultured together as indicated in FIG. 6. OVA-specific T-cells cultured with OVA peptide and APC served as a control. Supernatants were removed after 72 hours and the concentrations of IL-4, IL-5, IL-10 and IFN-gamma determined by specific immunoassay. Proliferation was determined by measuring thymidine incorporation after 96 hours culture.
Figure 6B:
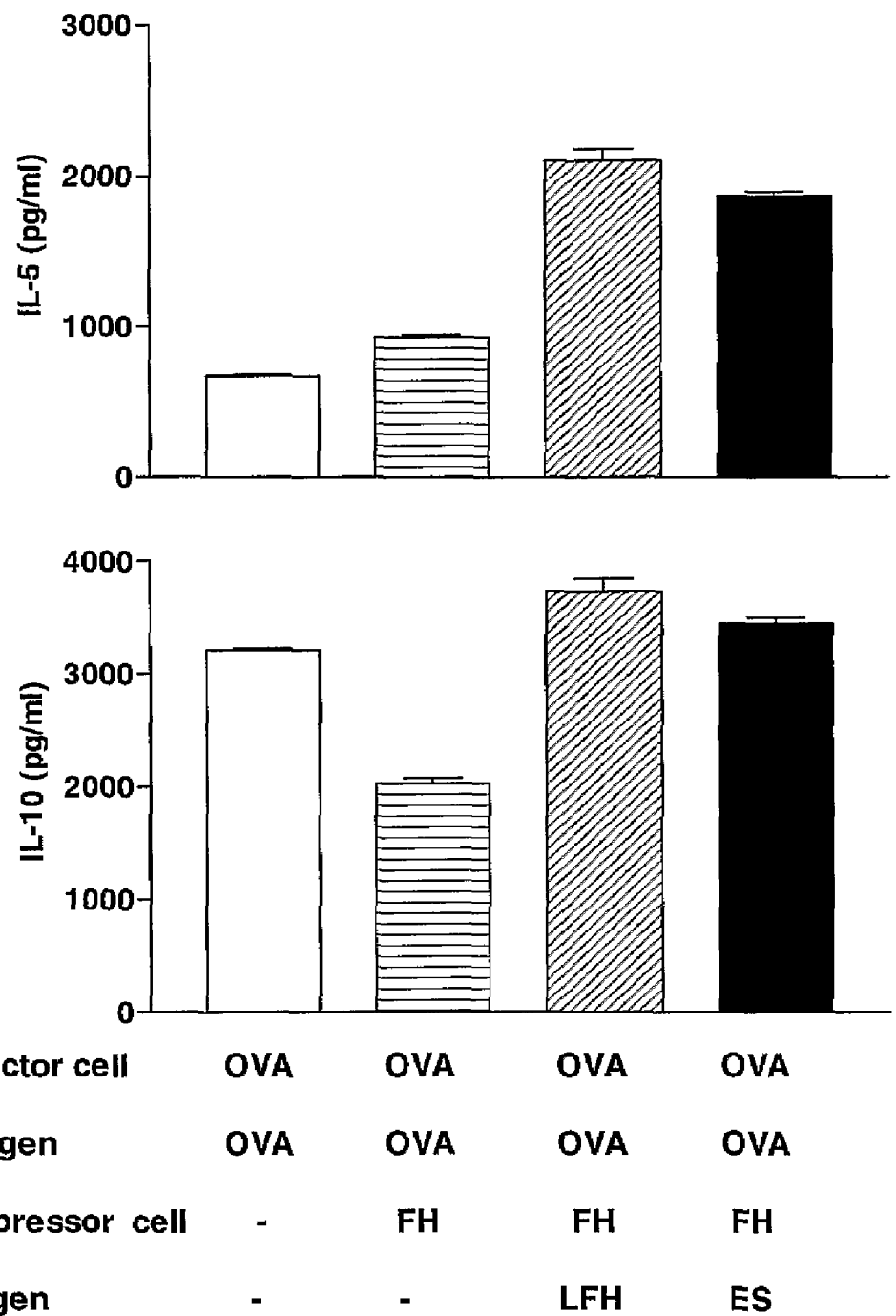

T Cells from the Peritoneal Cavity of *F. hepatica* Infected Mice Have Suppressor Activity Having demonstrated that T cells in the peritoneal cavity of *F. hepatica* infected mice secrete IL-10 and a have a regulatory phenotype, we examined their suppressor activity in co-culture experiments with T cells from ovalbumin (OVA) T cell receptor (TCR) transgenic (Tg) mice. A high frequency of DO11.10 TCR Tg mice are specific for OVA and are a useful readout of antigen-specific responses. T cells from DO11.10 TCR Tg mice proliferate and secrete IFN-γ, IL-4, IL-5 and IL-10 following stimulation with antigen (OVA) and antigen presenting cells (APC) in vitro. Co-cultivation with T cells from the peritoneal cavity of *F. hepatica* infected mice had a marked suppressive effect on proliferation and IFN-γ production. This was observed with and without stimulation with antigen (liver fluke homogenate; LFH or excretory/secretory fraction from *F. hepatica*; ES). IL-4 production was also reduced especially with un-stimulated T cells from *F. hepatica* infected mice. In contrast, IL-5 and IL-10 production was enhanced, especially with antigen-stimulated cells from *F. hepatica* infected mice (FIG. 6).

Figure 7A:
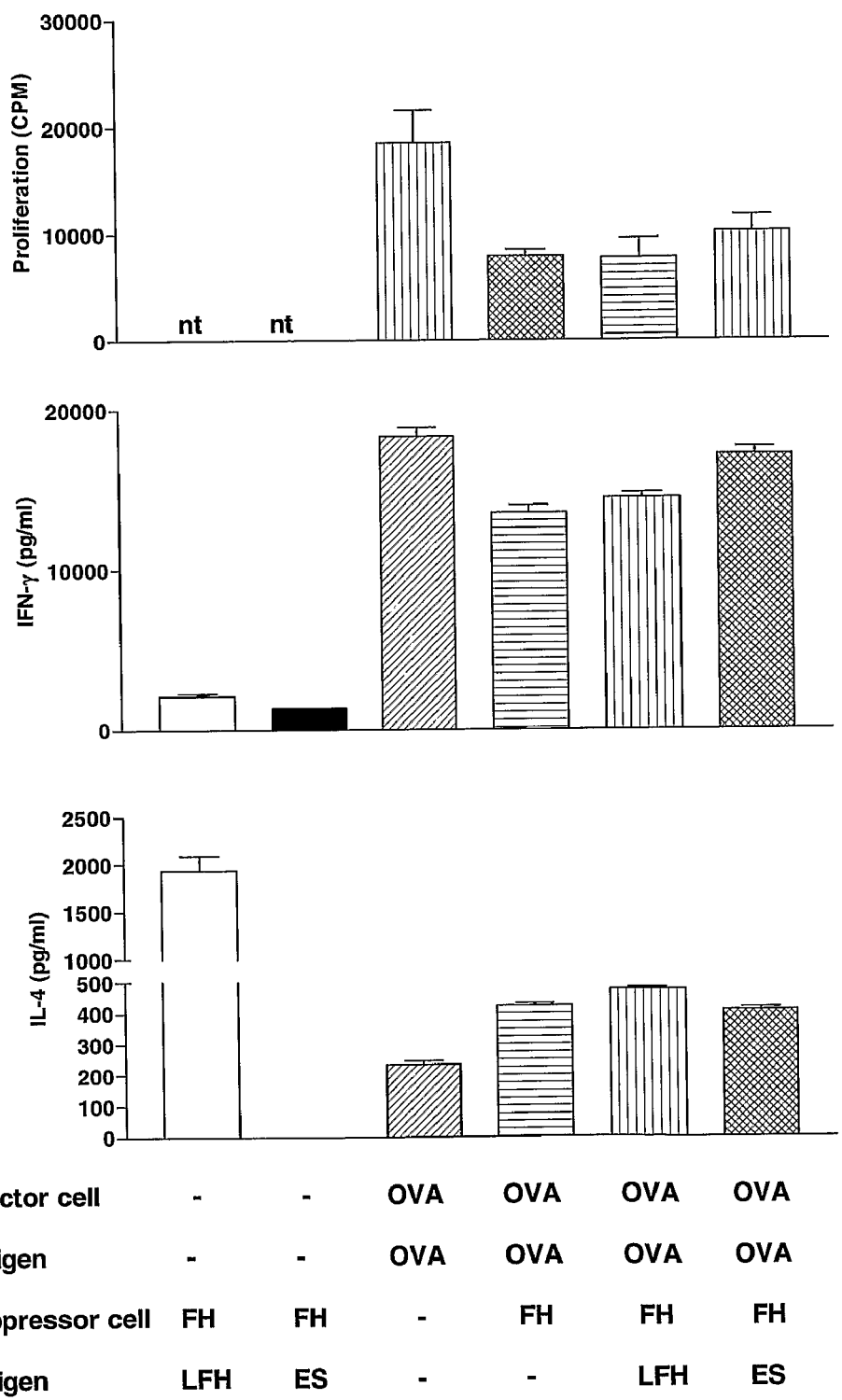
FIG. 7 shows that the suppressive capacity of T-cells induced during $F.$ hepatica infection is mediated in part by soluble factors. CD4$^+$ T-cells were purified from the peritoneal cavity of $F.$ hepatica-infected mice 3 weeks post-infection. Purified CD4$^+$ T-cells from $F.$ hepatica-infected mice were cultured with ES (20 µg/ml) products or LFH (20 µg/ml), together with irradiated spleen cells as antigen presenting cells (APC; 2×10$^6$/ml), alone or together with purified CD4$^+$ T-cells from DO11.10 Tg mice, with OVA peptide (2 µg/ml) and splenic APC. OVA-specific T-cells and $F.$ hepatica-specific T-cells were separated by a semi-permeable membrane. OVA-specific T-cells cultured with OVA peptide and APC served as a control. Supernatants were removed after 72 hours and the concentrations of IL-4, IL-5, IL-10 and IFN-gamma determined by specific immunoassay. Proliferation was determined by measuring thymidine incorporation after 96 hours culture.
Figure 7B:
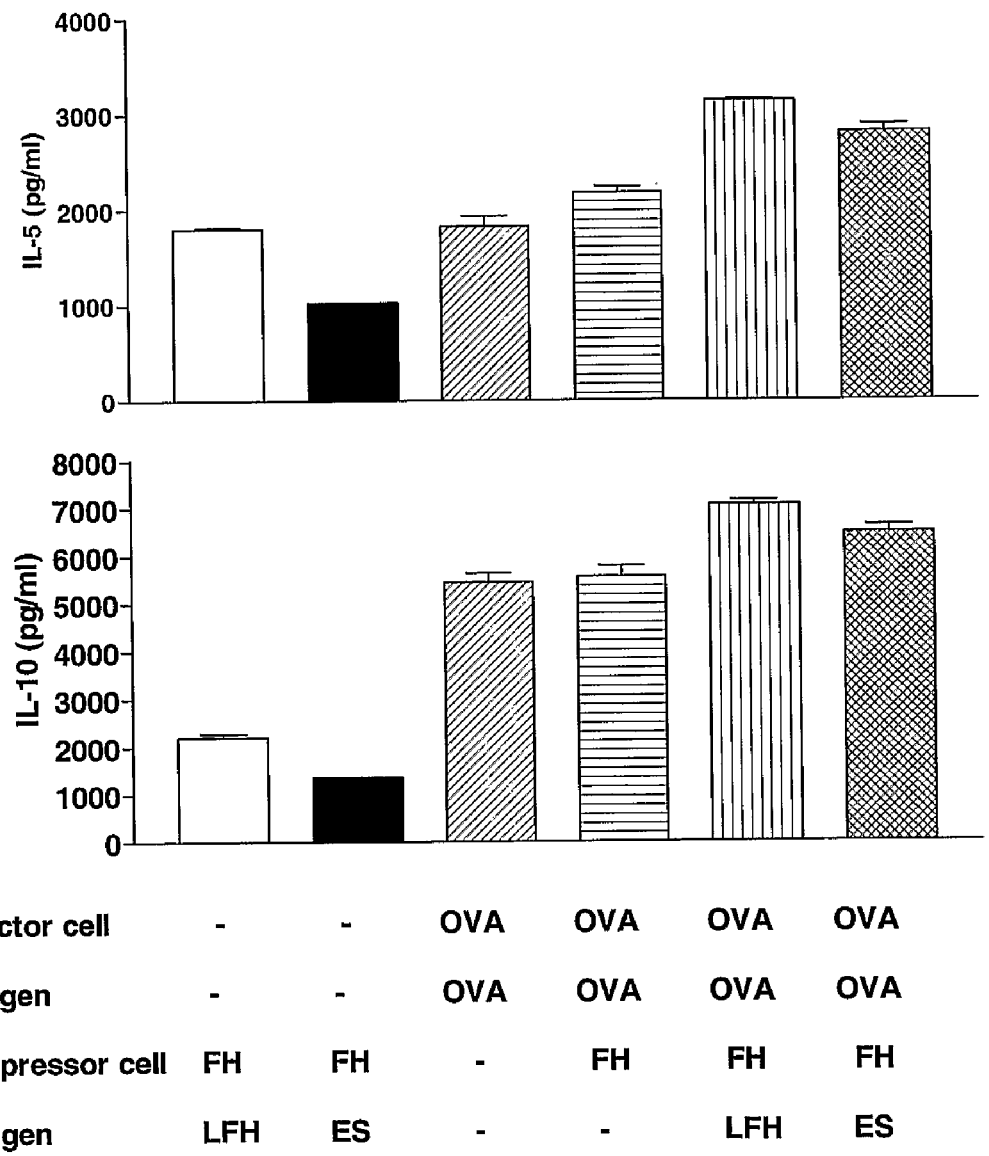

We next assessed the mechanisms of suppression, specifically the role of cell contact versus soluble factors. Here the T cells from DO11.10 TCR Tg mice were separated from the T cells from the *F. hepatica* infected mice by a semi-permeable membrane. Stimulation of the T cells from the peritoneal cavity of *F. hepatica* infected mice with LFH or ES resulted in the production of high concentrations of IL-5 and IL-10 and low concentrations of IFN-γ. IL-4 was also detected following stimulation with LFH, but not with ES (FIG. 7). Simulated of T cells from DO11.10 TCR Tg mice with OVA resulted in strong proliferation and secretion of IFN-γ, IL-4, IL-5 and IL-10. Co-culture with T cells from *F. hepatica* infected mice partially suppressed proliferation and IFN-γ production, but enhanced IL-4, IL-5 and IL-10 production.

These findings demonstrate that T cells from *F. hepatica* infected mice suppress T cell responses to an unrelated antigen in a bystander fashion. Furthermore this suppression is in part mediated by a soluble factor, possibly IL-10, which was secreted in high concentrations by T cells from *F. hepatica* infected mice.

IL-10 Production During *F. hepatica* Infection Regulates IL-5 and IFN-γ Production in Vivo In order to examine the role of IL-10 in the suppression of immune responses in vivo, C57BU6 and IL-10 knockout mice were infected with *F. hepatica* and cytokine production was examined in the peritoneal fluid and from mesenteric lymph node cells re-stimulated with antigen in vitro.

Figure 8A:
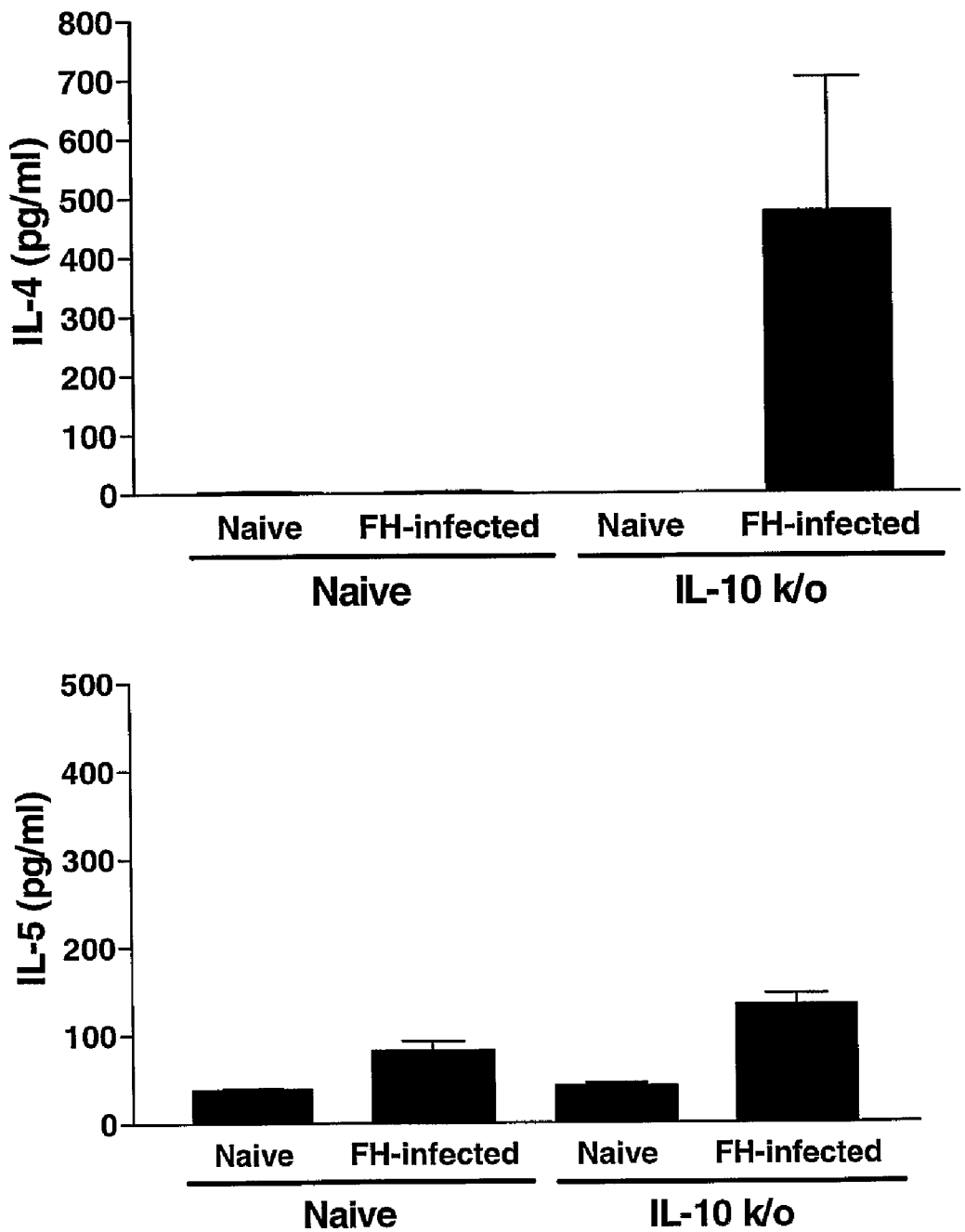
FIG. 8 shows that IL-10 and IL-5 are induced in the peritoneal cavity of *F. hepatica*-infected mice and IL-4 is induced in IL-10-defective mice. C57BU6 and IL-10-knockout (KO) mice were infected with *F. hepatica*. Three weeks post-infection, peritoneal fluid was recovered by lavage. After centrifugation, supernatants were removed and analysed for the presence of IL-4, IL-5, IL-10 and IFN-gamma by immunoassay. Data represents the mean (±SE) cytokine concentrations from individual mice.
Figure 8B:
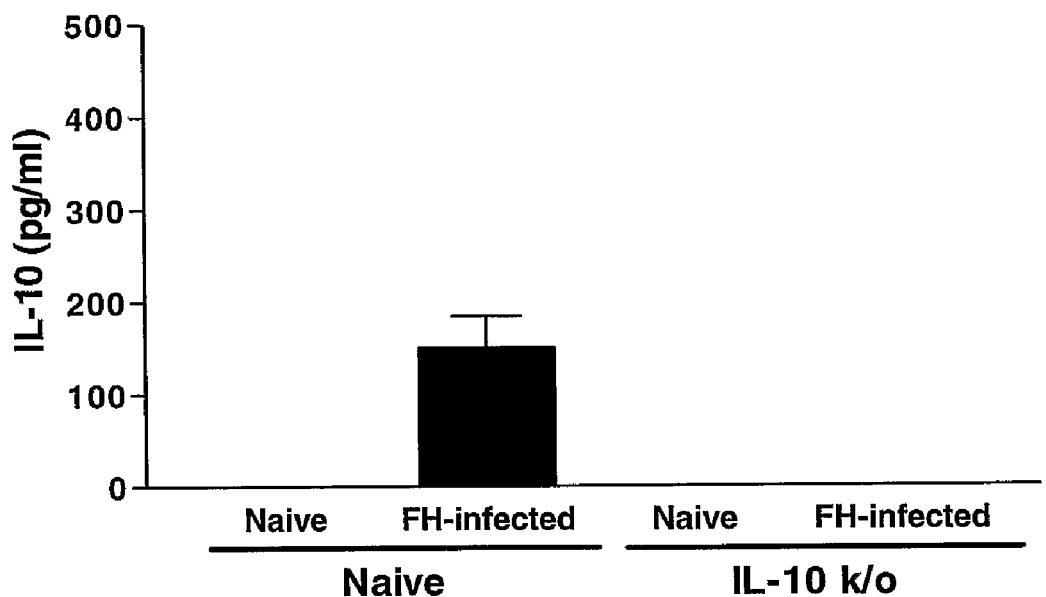
Figure 8B:
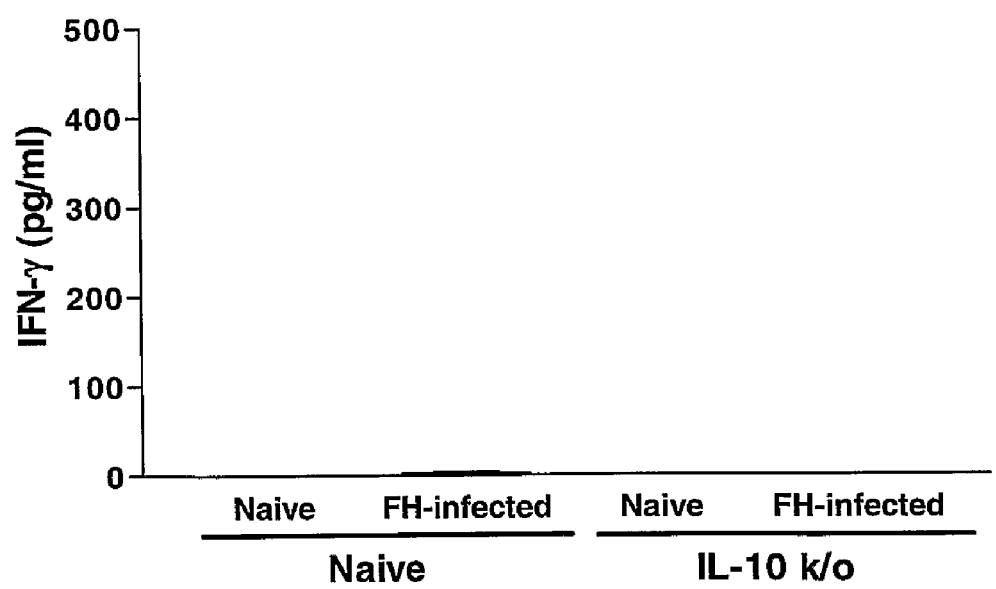
Figure 9A:
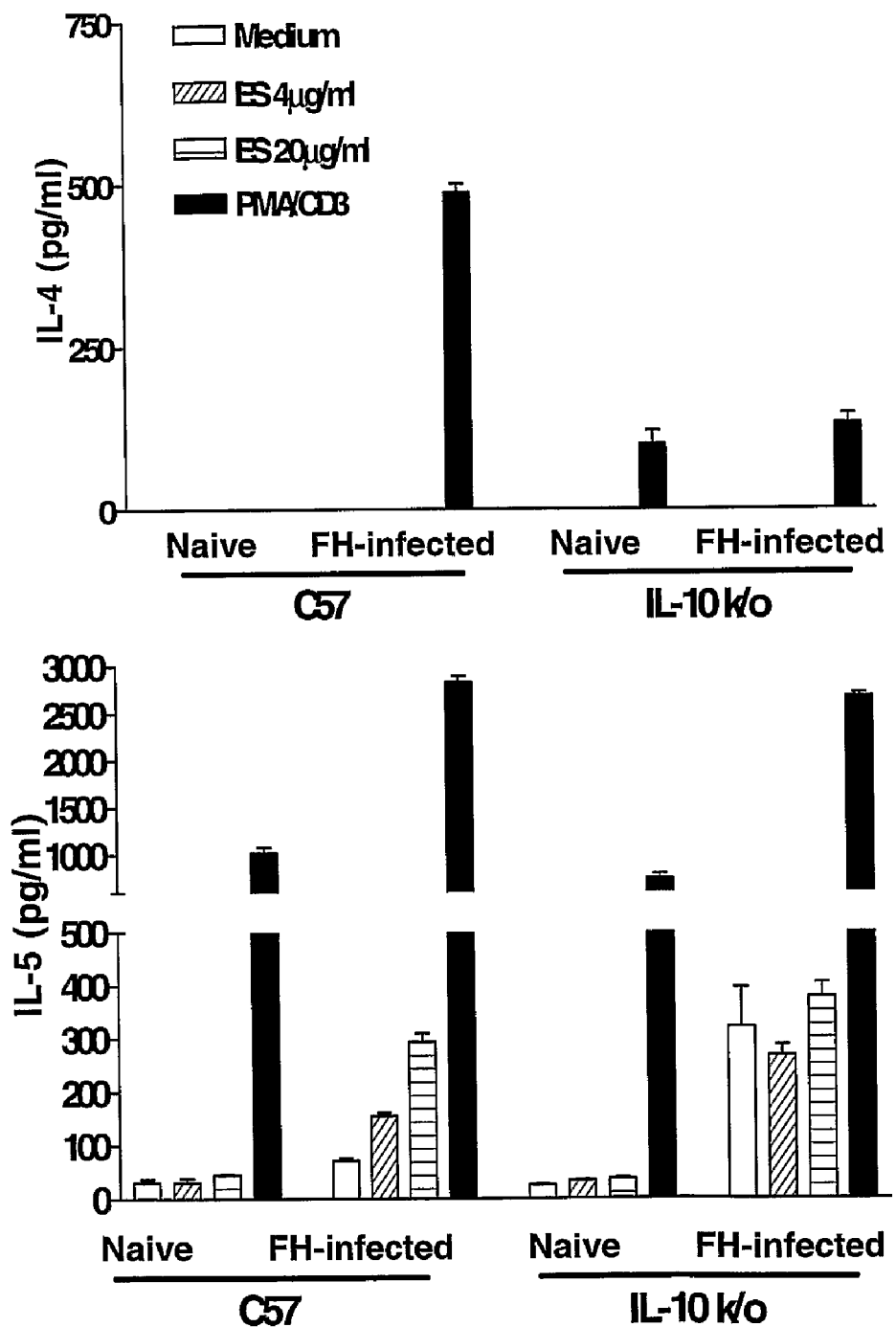
FIG. 9 shows that infection with *F. hepatica* induces IL-5 and IL-10-secreting T cells in the mesenteric lymph nodes and enhances IFN-gamma producing cells in IL-10 defective mice. C57BU6 and IL-10 knockout mice were infected with *F. hepatica*. Three weeks post-infection, ex vivo mesenteric lymph node cells were stimulated in vitro with medium only, ES (4 and 20 µg/ml) or PMA and anti-CD3. Following 72 hours incubation, supernatants were removed and concentrations of IL-4, IL-5, IL-10 and IFN-γ assessed by ELISA. Data represents the mean (±SE) cytokine concentrations from individual mice.
Figure 9B:
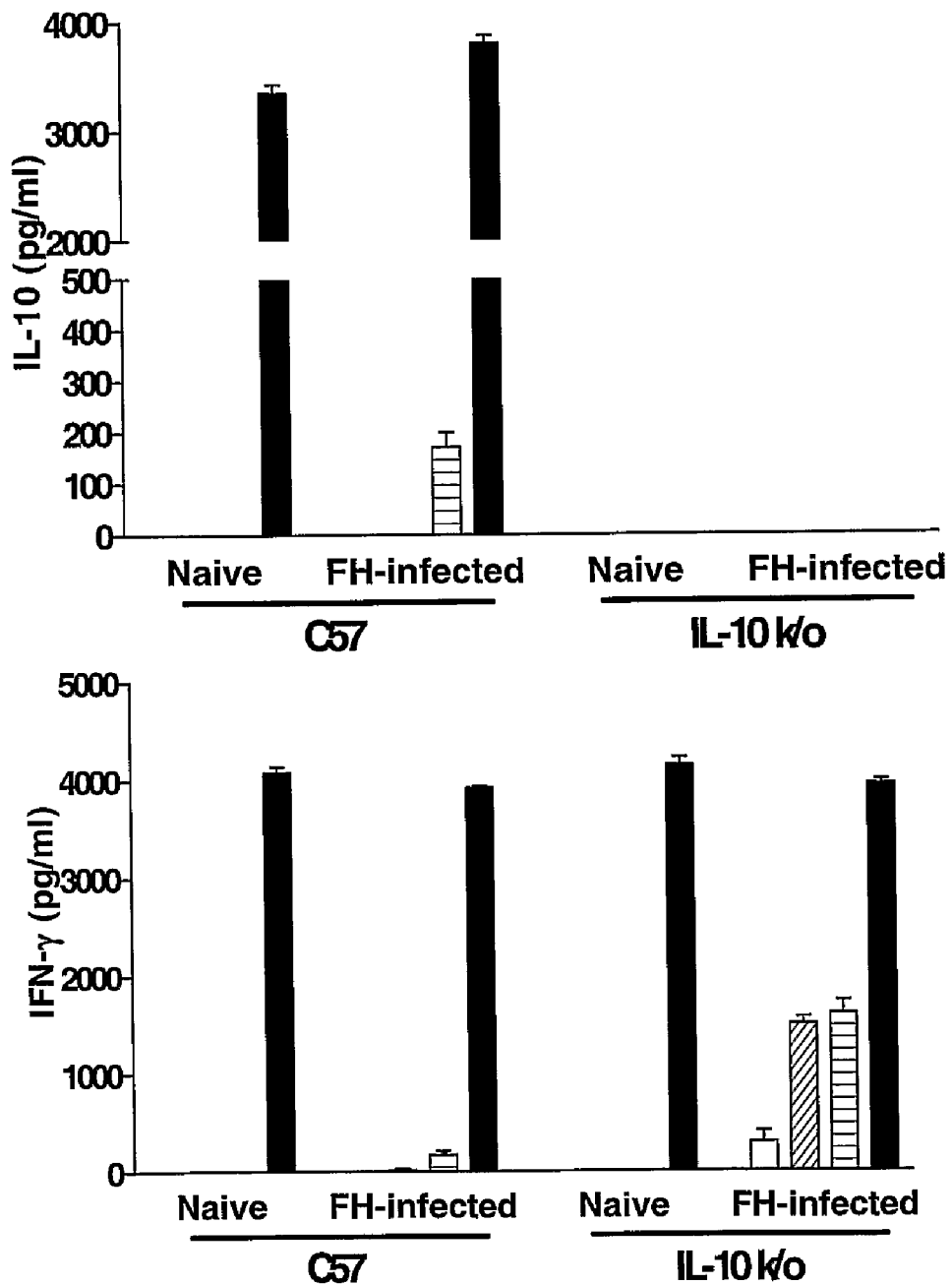

IL-10 and IL-5, but not IL-4 and IFN-γ were detected in the peritoneal fluid of C57BL/6 mice infected with *F. hepatica* (FIG. 8). In contrast, significant concentrations of IL-4 and enhanced IL-5 was detected in the peritoneal fluid of IL-10 knockout mice infected with *F. hepatica*. IL-10 and IL-5, but not IL-4 and IFN-γ were detected in ES-stimulated mesenteric lymph node cells from C57BU6 mice infected with *F. hepatica* (FIG. 9). In contrast, significant concentrations of IFN-γ and enhanced IL-5 was detected in ES-stimulated mesenteric lymph node cells from IL-10 knockout mice. These findings demonstrate that IL-10 producing cells in *F. hepatica* infected mice suppress both Th1 and Th2 cytokine production in vivo.

Figure 10A:
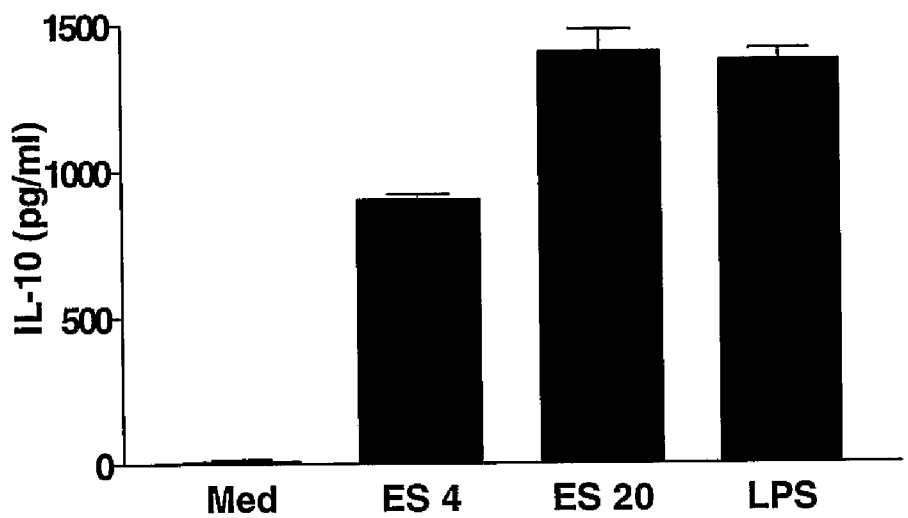
FIG. 10 shows that ES induces IL-10 production from innate cells. Peritoneal exudate cells (A), peritoneal macrophages (B), CD11c$^+$ DC from the peritoneum (C) and CD11c$^+$ DC from spleen (D) were stimulated at $1\times10^6$/ml with ES (4.0, 20.0 µg/ml), or liver fluke homogenate (LFH; 20 µg/ml), medium only or LPS (10 ng/ml). IL-10 concentrations were assessed after 24 hours.
Figure 10A:
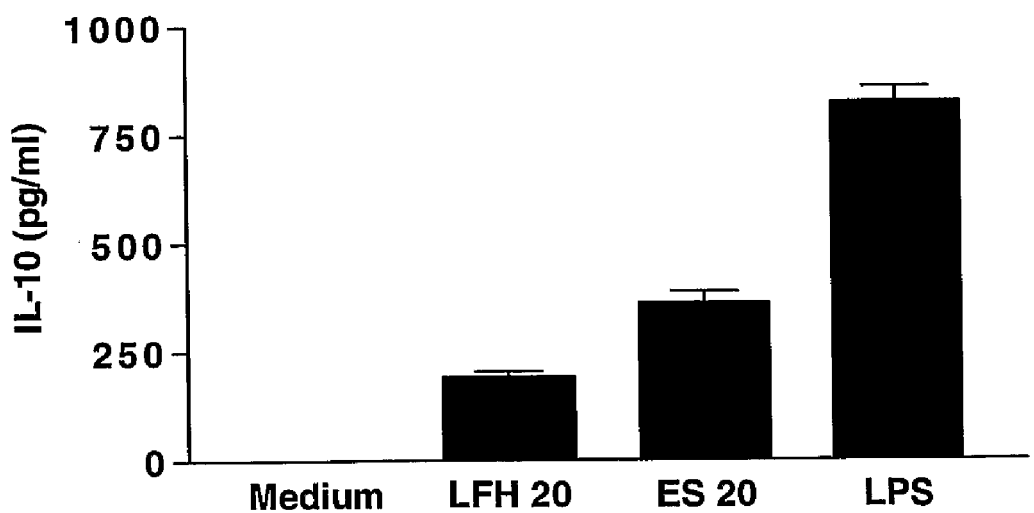
Figure 10B:
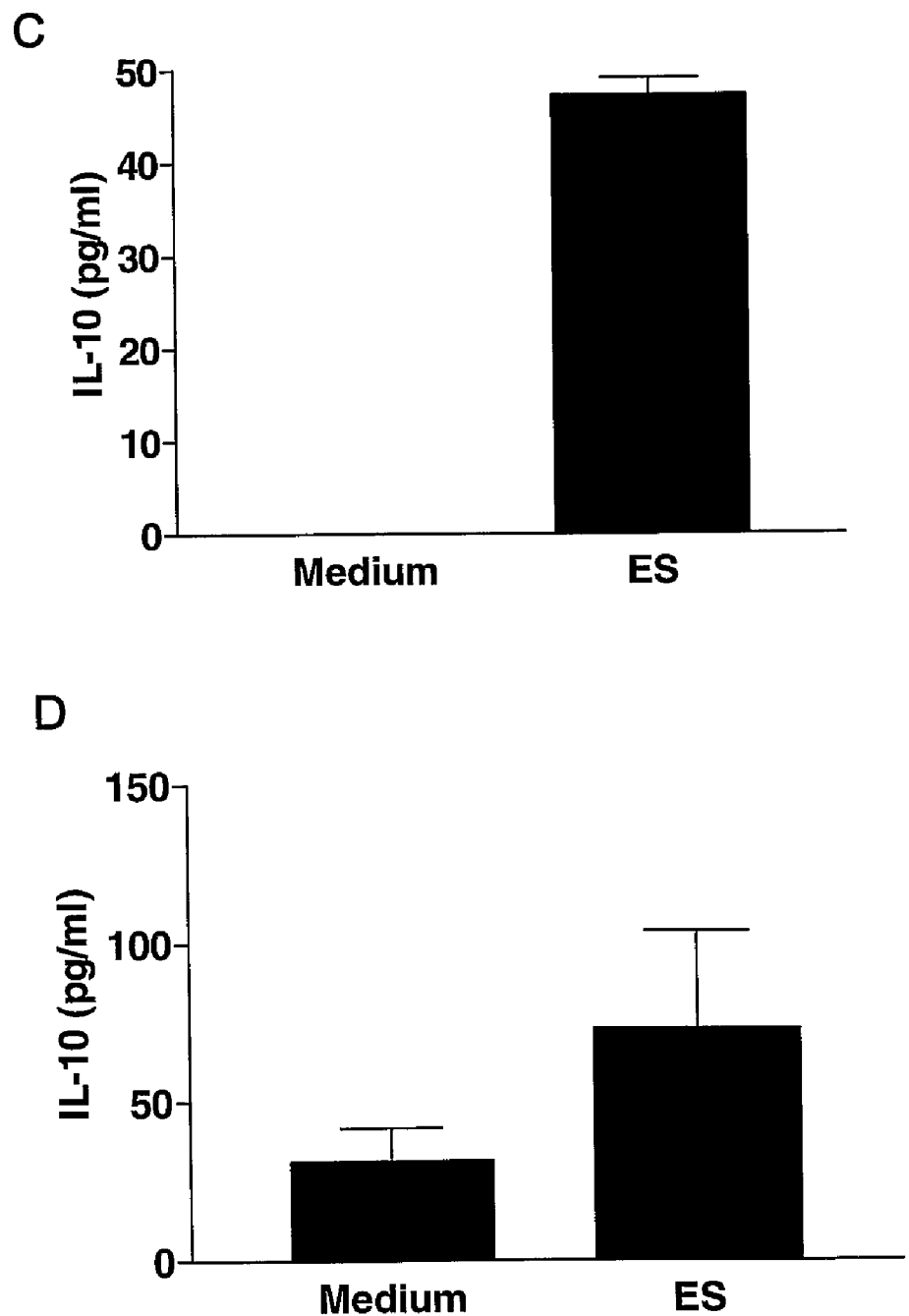
Figure 11:
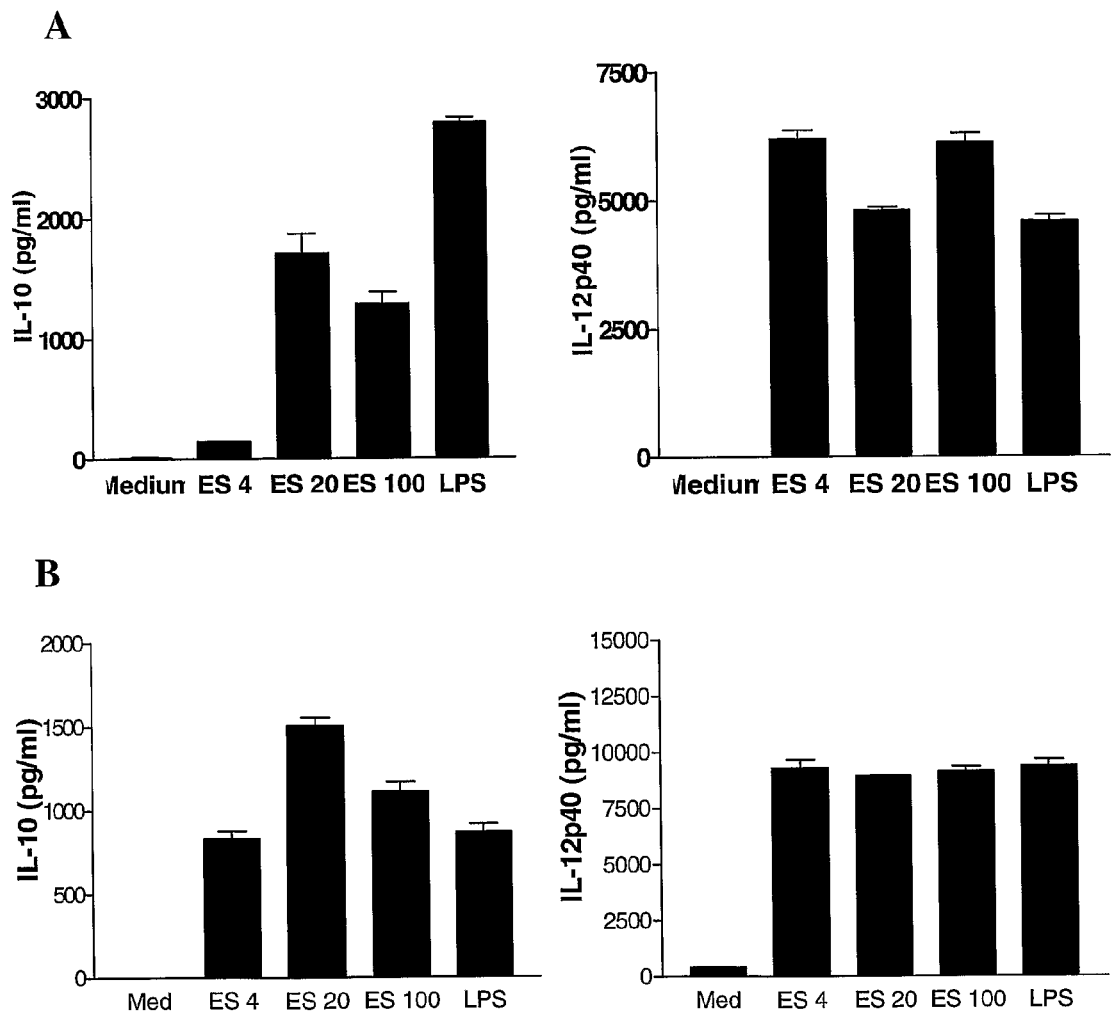
FIG. 11 shows that ES induces IL-10 and IL-12p40 production from macrophages and dendritic cells. J774 macrophages (A) and bone-marrow derived DC (B) ($1\times10^6$/ml) were stimulated with ES (4.0, 20.0 and 100 µg/ml), medium only or LPS (10 ng/ml). IL-10 and IL-12p40 concentrations were assessed after 24 hours.
Figure 12:
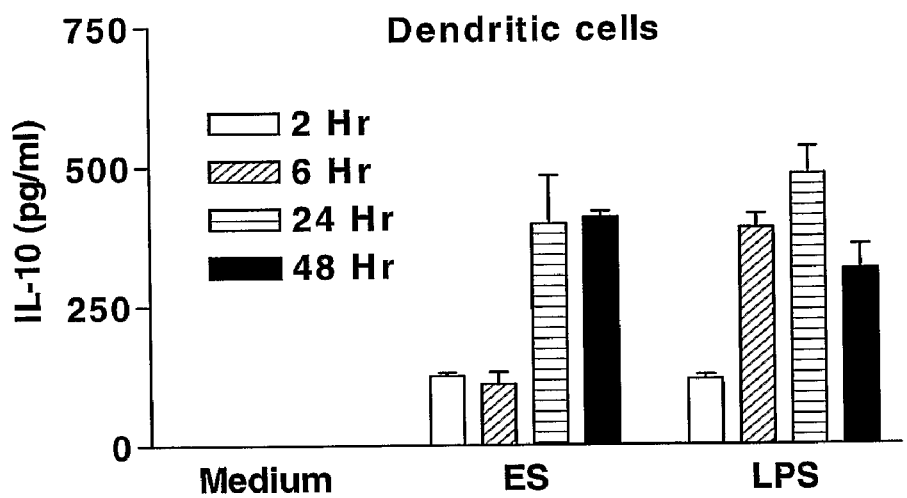
FIG. 12 shows the kinetics of ES-induced IL-10 production from BMDC and PEC. Bone-marrow-derived DC (A), or ex vivo PEC (B) ($1\times10^6$/ml), were stimulated with medium only, ES (20 µg/ml), or LPS (10 ng/ml). Supernatants were removed after 6, 12, 24 or 48 hours and assessed for IL-10 production by ELISA.
Figure 12:
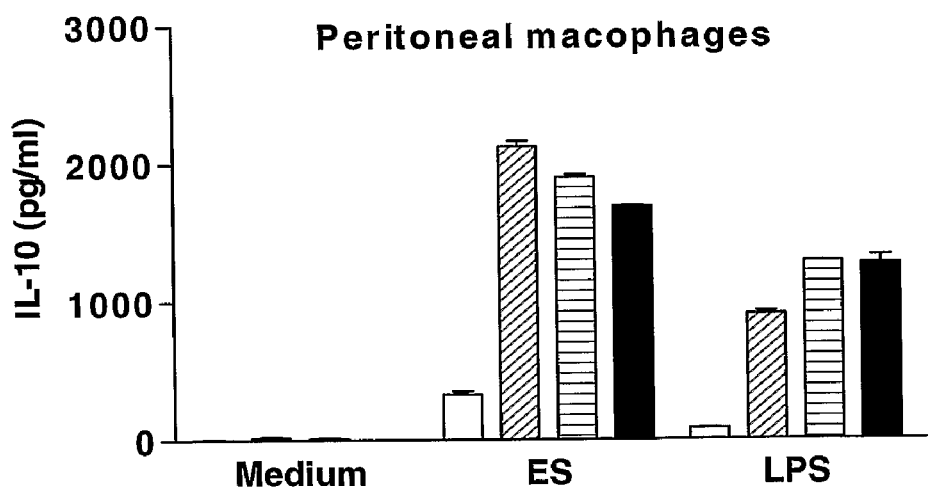

*F. hepatica* Excretory/Secretory (ES) Products Stimulate Innate IL-10 Production Having demonstrated that *F. hepatica* infection induces IL-10 production from innate cells and T cells, we examined the influence of *F. hepatica* ES on IL-10 production by cells of the innate immune system. Peritoneal exudate cells, peritoneal macrophages, J774 macrophages, bone marrow-derived DC and CD11c$^+$ DC from the peritoneum and the spleen all secreted IL-10 in responses to ES (FIGS. 10 and 11). We found that liver fluke homogenate (LFH) also stimulated IL-10 production from peritoneal macrophages. IL-12p40, but not IL-12p70 production was detected in supernatants of bone marrow derived DC and J774 cells (FIG. 11). IL-10 production was detected in macrophages 6-48 hours and in DC 24-48 hours after in vitro stimulation with ES (FIG. 12).

ES Stimulates Innate IL-10 and IL-4 Production in Vivo

Figure 13:
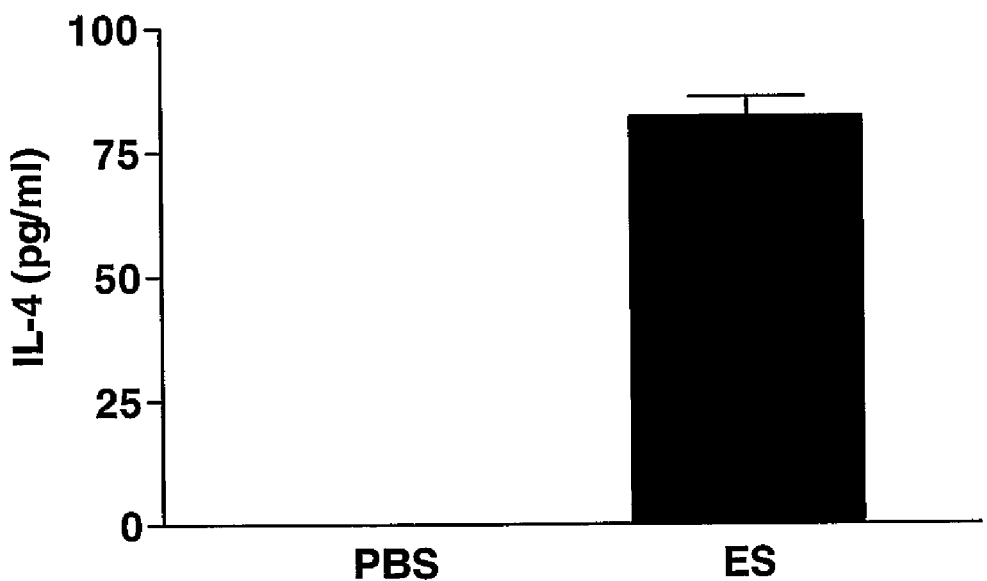
FIG. 13 shows that ES induces IL-10 and IL-4 production in draining lymph node after sub-cutaneous administration in vivo. Groups of 4 mice were injected sub-cutaneously with either 200 µl PBS or ES (50 µg). After 6 hours, inguinal nodes were removed and homogenised in 1 ml ice-cold PBS. Following centrifugation, the supernatant was removed and analysed for IL-4, IL-10 and TGF-β concentrations by ELISA.
Figure 13:
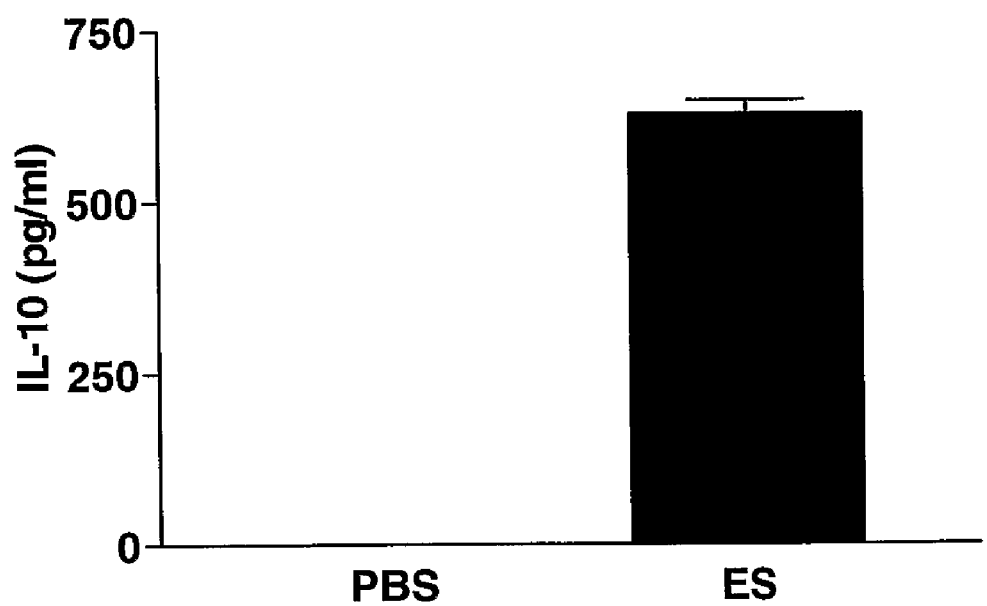
Figure 14:
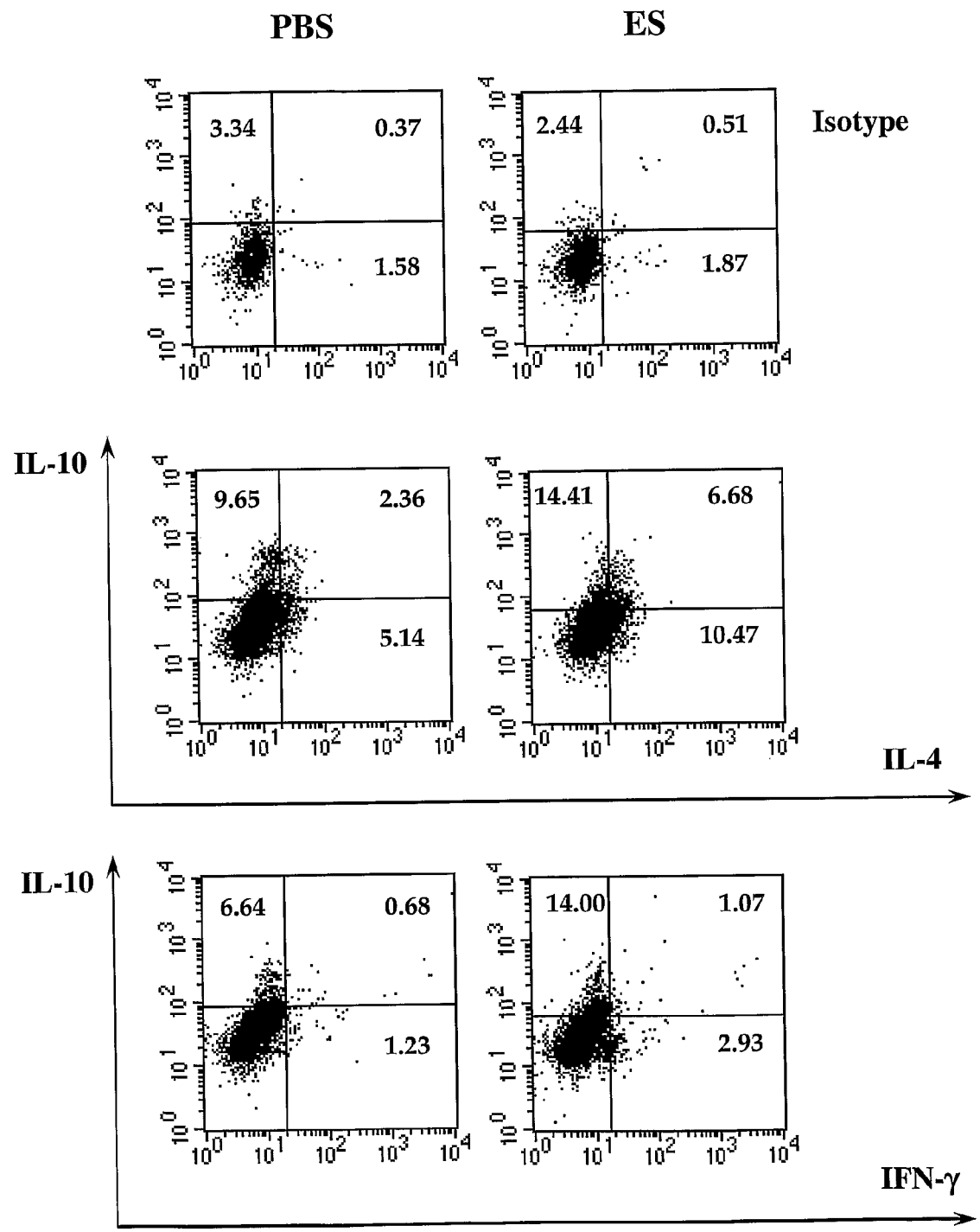
FIG. 14 shows that ES induces IL-10 and IL-4 production by dendritic cells in peritoneal cavity after i.p. administration in vivo. Groups of 4 mice were injected i.p. with PBS or ES (50 µg). After 2 hours, peritoneal exudate cells (PEC) from PBS- and ES-injected mice were harvested by peritoneal lavage. Cells were blocked and surface labelled with anti-CD11c, before fixing and permeabilising for intracellular cytokine labelling by fluorescently labelled anti-IL-10, anti-IL-4 and anti-IFN-γ antibodies. Cells were then analysed using a flow cytometer and gated for the CD11c$^+$ cell population.

Having demonstrated the induction of IL-10 by innate immune cells in vitro, we examined the ability of ES to stimulate innate cytokine production in vivo. Mice were injected s.c. in the flank and the draining lymph nodes were removed 6 hours later and homogenized and IL-4 and IL-10 concentrations determined by ELISA. Alternatively mice were injected i.p. and peritoneal DC were assessed for cytokine production after 2 hours. The results revealed that s.c injection of ES stimulated the production of significant concentrations of IL-10 and lower concentrations of IL-4 in the draining lymph node (FIG. 13). Injection of ES by the i.p. route also stimulated IL-10 and IL-4 producing DC cells in the peritoneal cavity. The frequency of IL-10-secreting DC increased from 7-12% in control mice to 15-21% in ES-injected mice and the frequency of IL-4 producing cells increased from 7.5 to 17% (FIG. 14). There was a less significant increase in the frequency of IFN-γ secreting DC from 1.9 to 4.0%.

ES Inhibits TLR Agonist-Induced IL-12p70 Production

Figure 15:
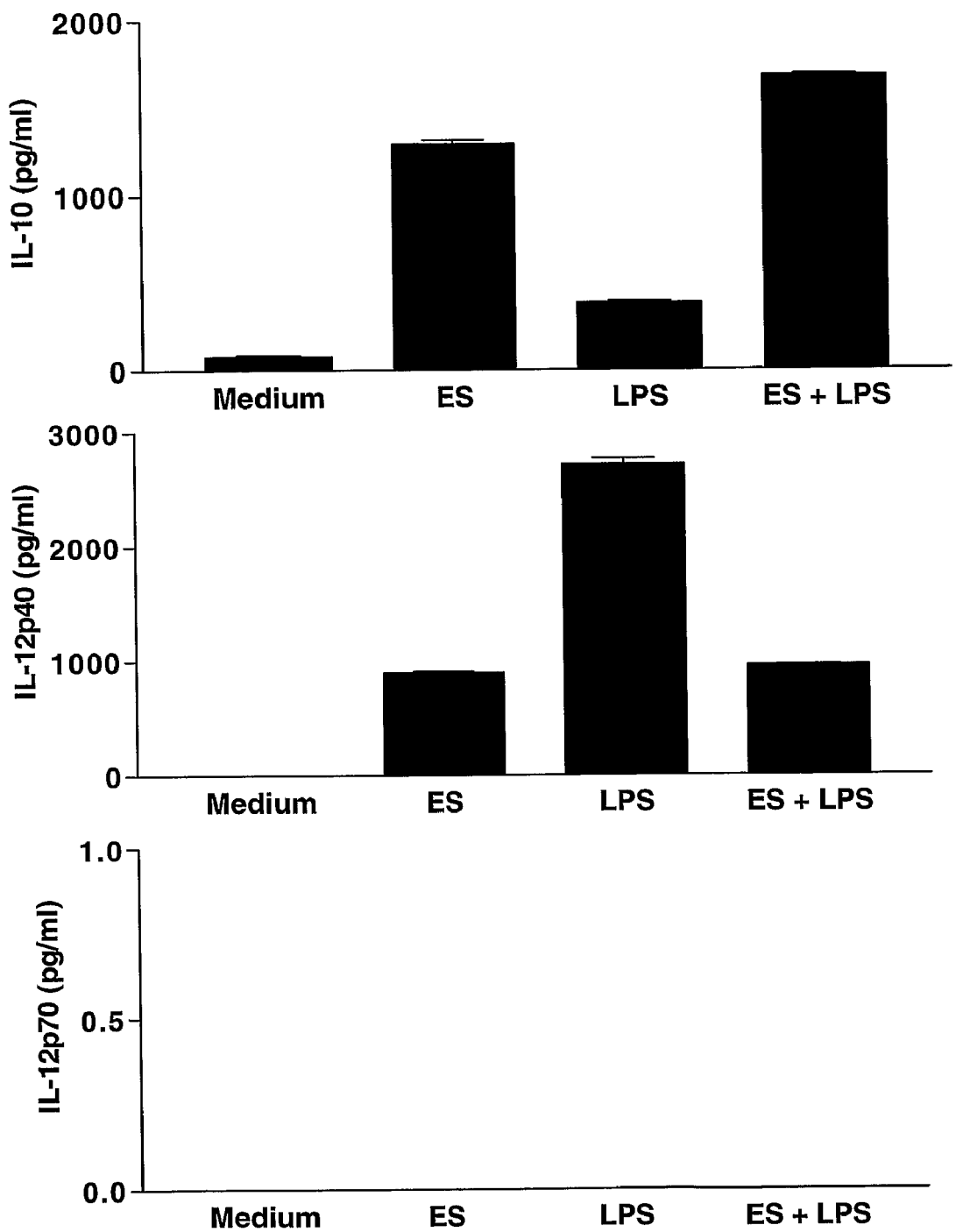
FIG. 15 shows that ES Inhibits LPS-induced IL-12p40 in J774 macrophages. J774 macrophages ($1\times10^6$/ml) were stimulated for 24 hours with medium only, LPS (10 ng/ml), ES (20 µg/ml), or LPS following a 2 hour pre-incubation with ES. Following incubation, supernatants were removed and concentrations of IL-10, IL-12p40 and IL-12p70 assessed by ELISA.
Figure 16:
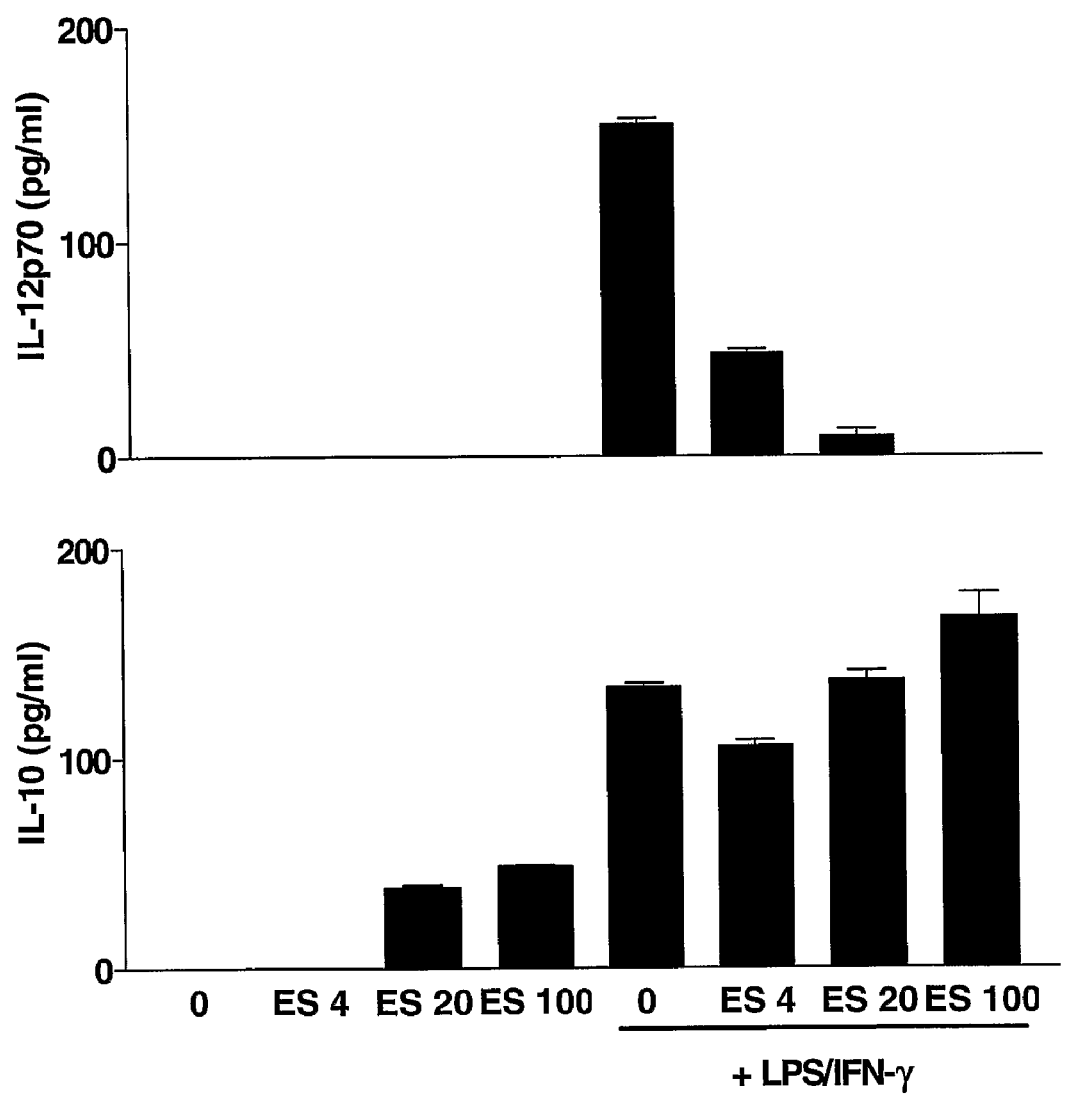
FIG. 16 shows that ES inhibits LPS-IFN-γ-induced IL-12p70 production in dendritic cells. Bone marrow-derived DC were stimulated for 24 hours with medium only, LPS (10 ng/ml) and IFN-γ (20 ng/ml), ES (4.0 or 20.0 µg/ml), or LPS and IFN-γ following a 2 hour pre-incubation with ES. Cytokine concentrations were assessed by ELISA.

IL-10 production by innate cells is associated with the induction of Treg cells, whereas IL-12 promotes the expansion of IFN-γ-secreting Th1 cells. Therefore we examined the influence of ES on IL-12p40 and IL-12p70 production by macrophages and DC. ES alone did not stimulate IL-12p70, but did stimulate IL-12p40 and IL-10 production from J774 macrophages (FIG. 15). Furthermore, LPS-induced IL-12p40 was inhibited by 2 hours pre-incubation with ES. ES did not induce IL-12p70 from DC and inhibited IL-12p70 induced by LPS and IFN-γ. The inhibitory effect of ES was observed over a wide concentration range and was very pronounced at higher concentrations (FIG. 16).

Figure 17:
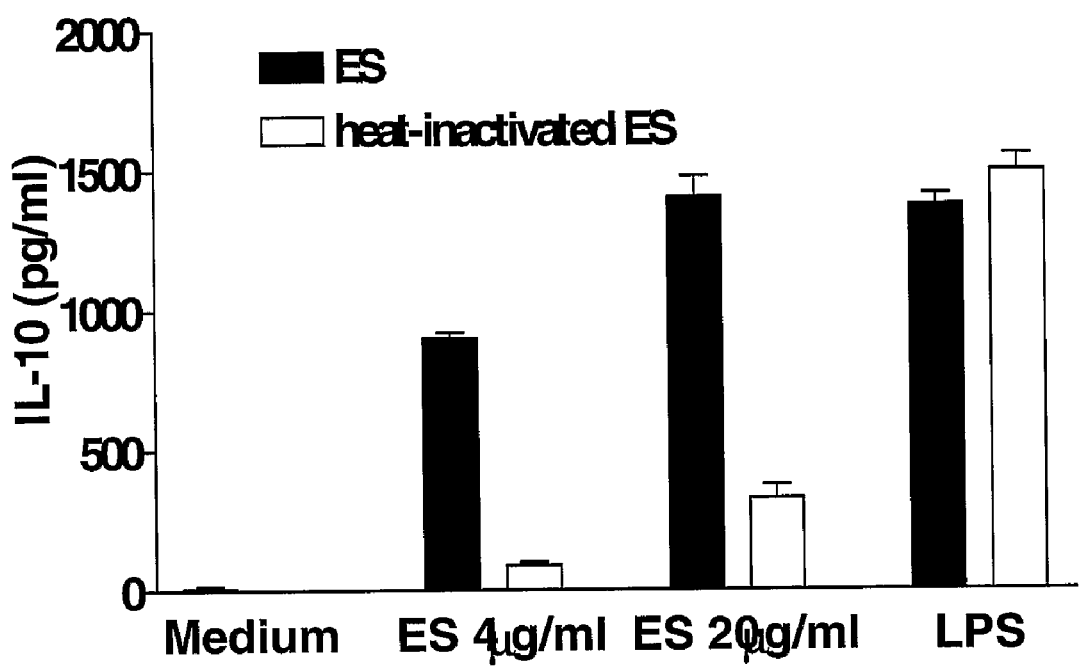
FIG. 17 shows that ES-induced IL-10 production is abrogated by heat inactivated ES. Peritoneal exudate cells (PEC) were isolated from naïve mice by peritoneal lavage in cold PBS. PEC ($1\times10^6$/ml) were then stimulated with native or heat-inactivated ES (4.0 and 20 µg/ml), medium only or LPS (10 ng/ml) as negative and positive controls respectively. Cytokine concentrations in the supernatants were assessed after 24 hours.
Figure 18:
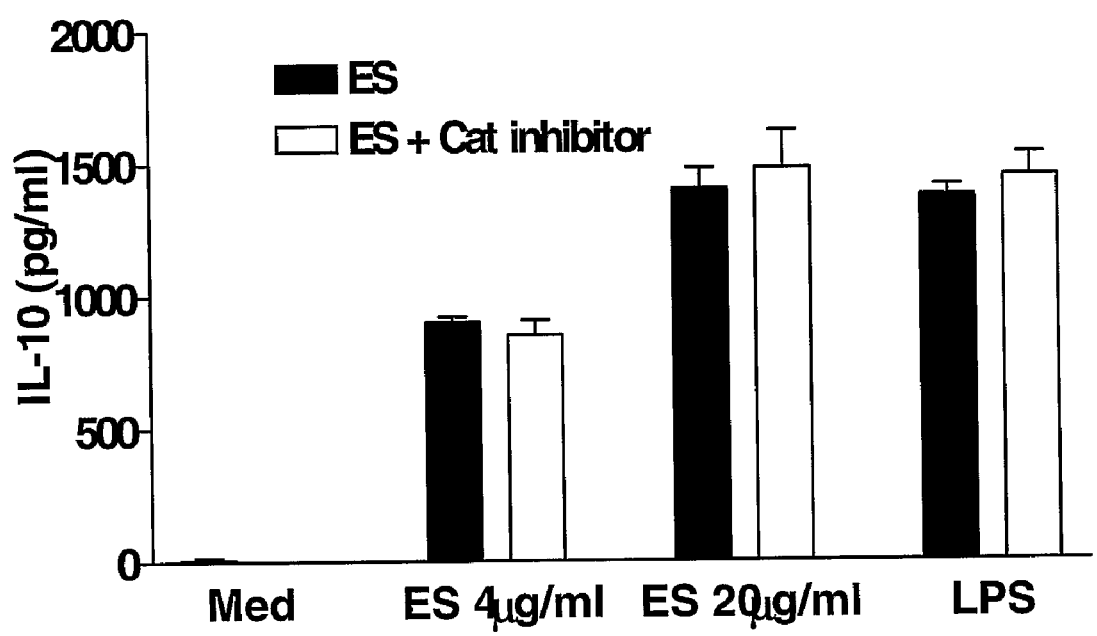
FIG. 18 shows that IL-10 induction by ES is not mediated by cathepsins. Peritoneal exudate cells (PEC) were isolated from naïve mice by peritoneal lavage in cold PBS. PEC ($1\times10^6$/ml), were then stimulated with ES (4.0 and 20 µg/ml) in the presence or absence of a cathepsin inhibitor E-64 (10 mM). Stimulation with medium or LPS (10 ng/ml) served as negative and positive controls respectively. Cytokine concentrations in the supernatants were assessed after 24 hours.
Figure 19:
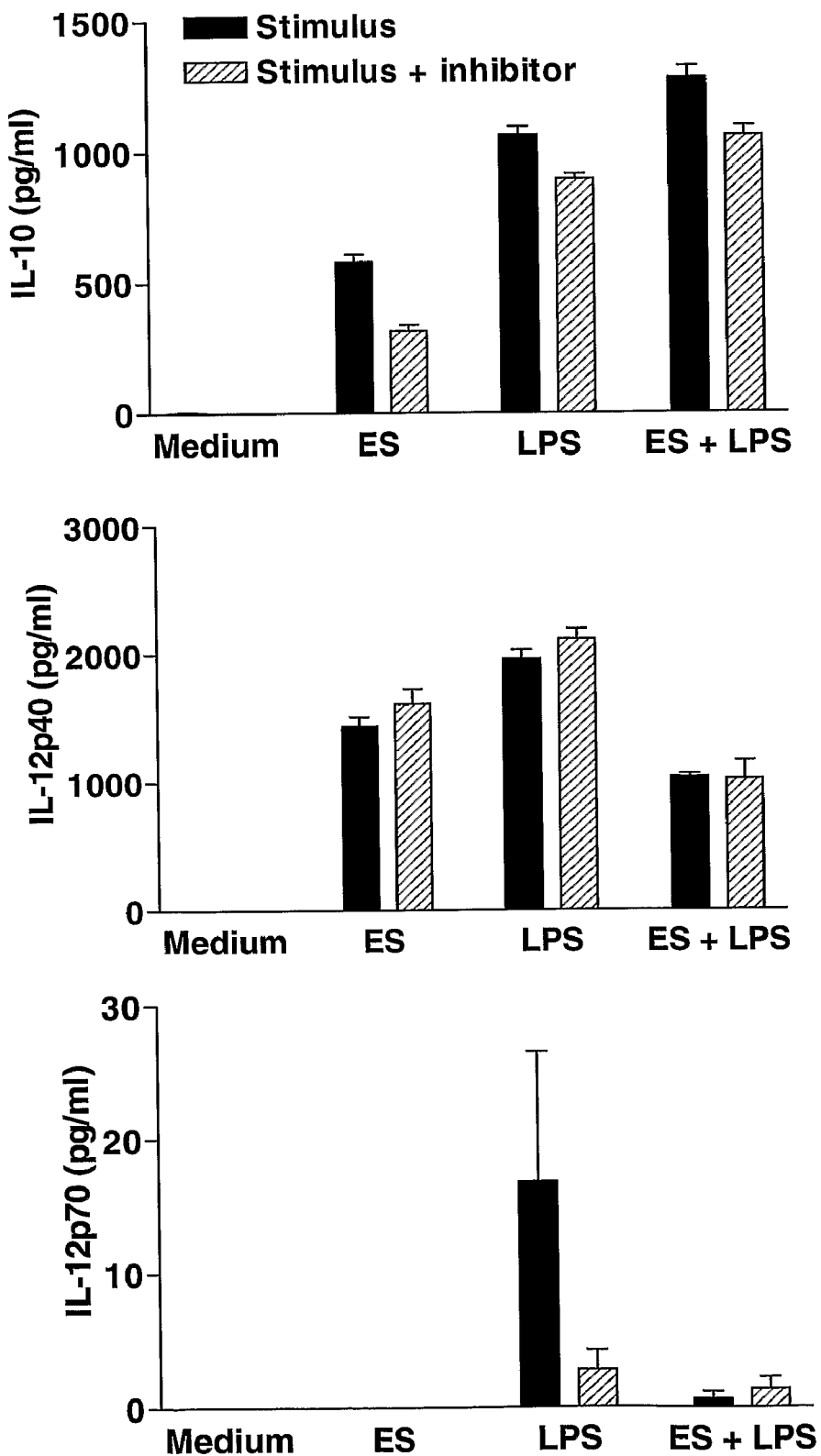
FIG. 19 shows that inhibition of LPS-induced IL-12p40 and IL-12p70 in J774 macrophages is not mediated by cathepsins. J774 macrophages ($1\times10^6$/ml) were stimulated for 24 hours with medium only, LPS (10 ng/ml), ES (20 µg/ml) or LPS following a 2 hour pre-incubation with ES, in the presence or absence of E-64 (10 mM). Following incubation, supernatants were removed and concentrations of IL-10, IL-12p40 and IL-12p70 assessed by ELISA.

The Immunomodulatory Effect of ES is Mediated by a Heat-Sensitive Molecule Other Than a Cathepsin It has previously been reported that cathepsin L proteinase from *Fasciola hepatica* has immunomodulatory properties. Here we assessed the role of cathepsins in the induction of IL-10 production. We first assessed the effect of heat treatment on the activity of ES. Heat-treatment of ES significantly reduced its ability to stimulate IL-10 production by peritoneal exudate cells (FIG. 17). In contrast, addition of a cathepsin inhibitor had no effect on the ability of ES to stimulate IL-10 or to inhibit IL-12p40 or mIL-12p70 production by DC (FIGS. 18 and 19). These findings suggest that the immunomodulatory product in the ES fraction that stimulates IL-10 production is not a cathepsin, but is heat-sensitive molecule.

ES Modulates Surface Marker Expression on DC and Macrophages

Figure 20A:
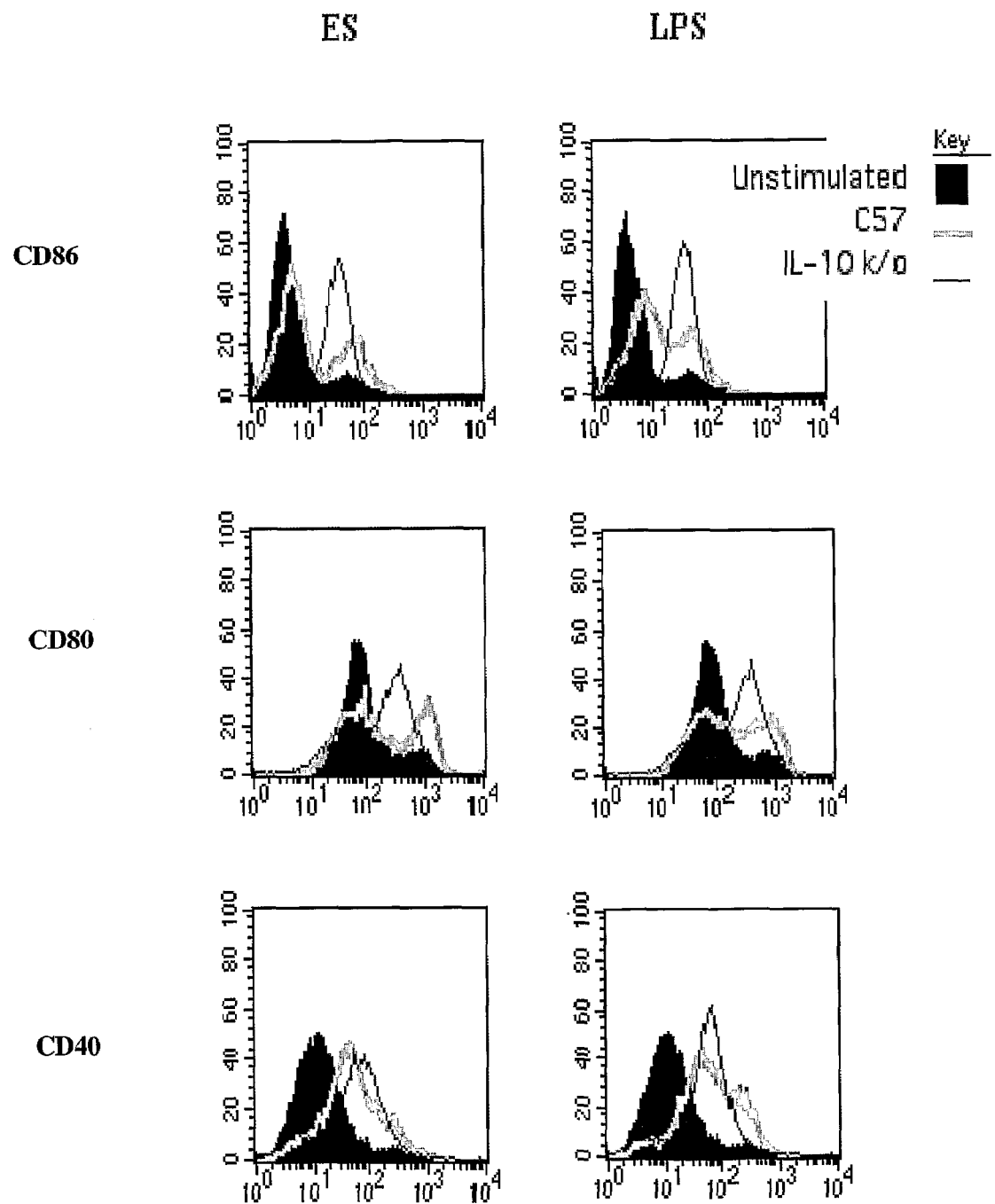
FIG. 20 shows that ES induces the maturation of DC. Bone marrow-derived DC ($1\times10^6$/ml), from C57BL/6 or IL-10 knockout (IL-10$^{-/-}$) mice were stimulated with medium only, ES (20 µg/ml), or LPS (10 ng/ml). After 24 hours incubation, the cells were stained for cytofluorometric analysis with mAbs CD11c, CD80, CD86, CD40, CCR5 and MHC Class II, or species- and isotype-matched control Abs. Cells were gated on the CD11c$^+$ (DC) population.
Figure 20B:
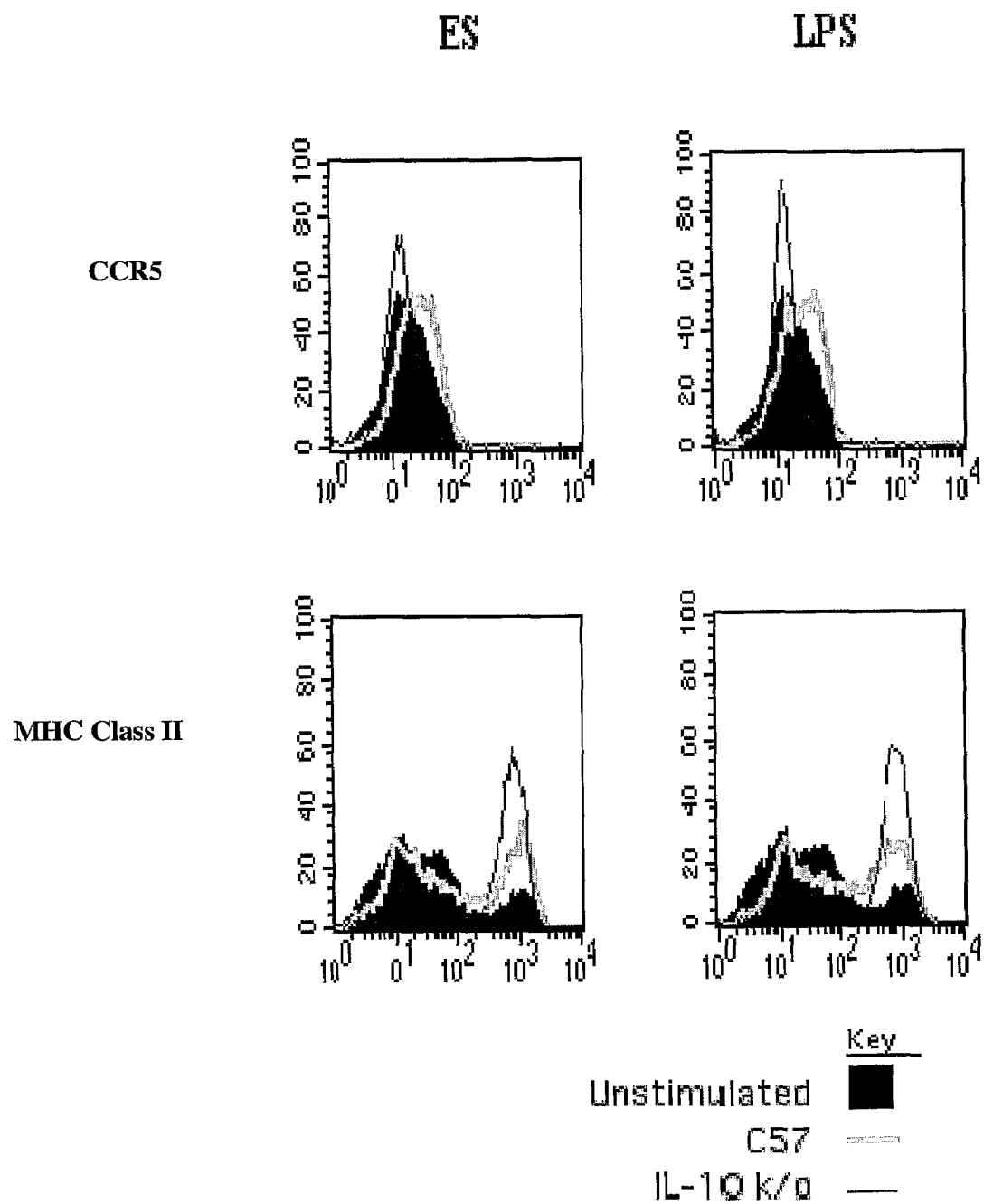

DC and macrophages are potent antigen presenting cells, but must first be activated to enhance expression of MHC class II and co-stimulatory molecules. Fully mature DC promote expansion of effector T cells, especially Th1 cells, whereas immature or partially mature DC promote expansion of anergic or regulatory T cells. Here we found that ES enhanced surface expression of CD86, CD80, CD40 and MHC class II in DC from C57BL/6 mice. The level of activation was similar to that observed with LPS. However, unlike LPS which suppressed CCR5 expression (CCR5 expression is normally reduced following DC maturation), ES enhanced CCR5 expression. In IL-10-defective mice this enhancement was not observed. Furthermore, CD80, CD86, CD40 and MHC class II was enhanced in ES-stimulated DC from IL-10-defective mice (FIG. 20). This suggests DC maturation is constrained by ES-induced IL-10 production.

Figure 21A:
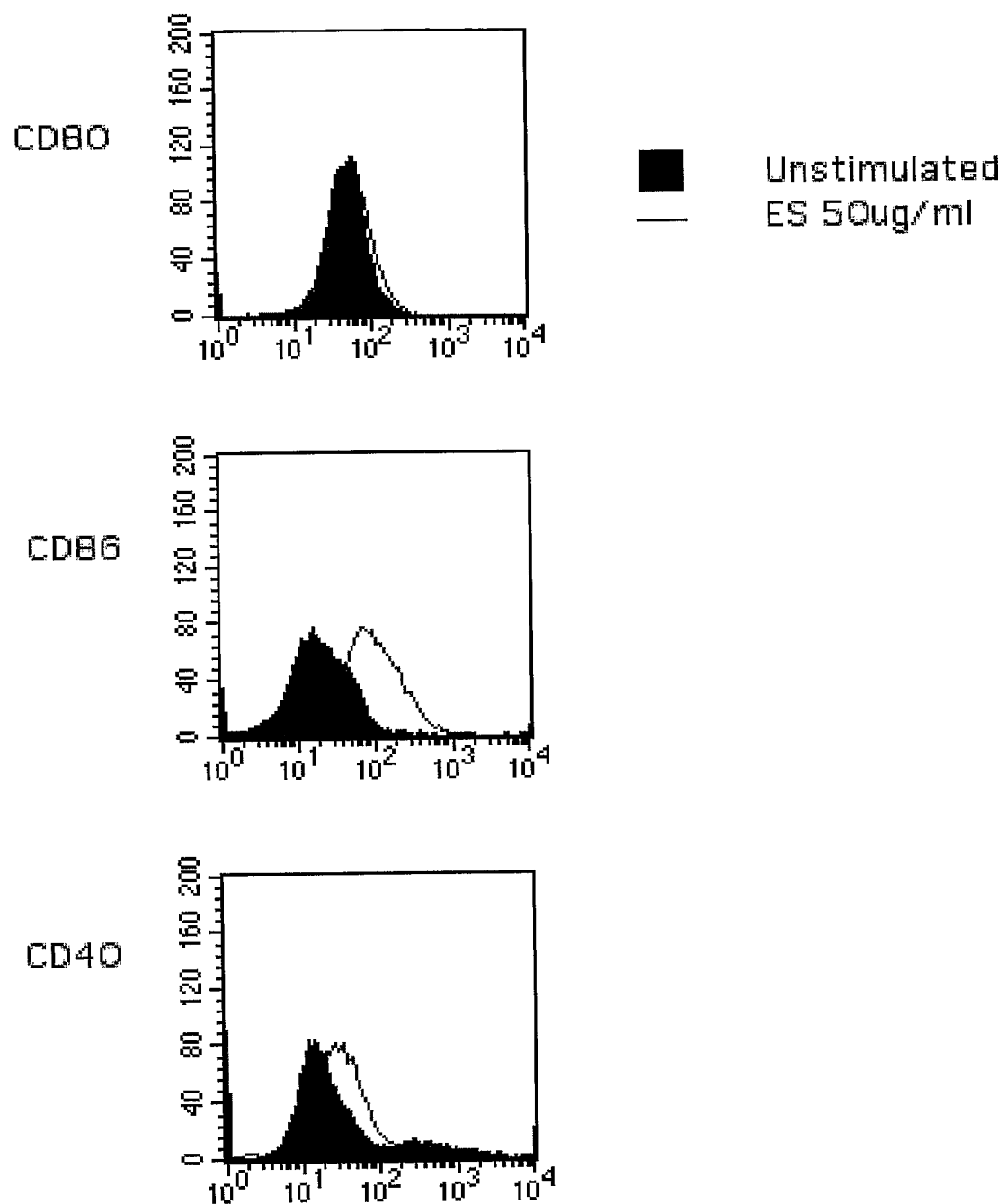
FIG. 21 shows that ES enhances MHC class II and co-stimulatory molecule expression on macrophages. J774 macrophages ($1\times10^6$/ml) were stimulated for 24 hours with medium only, ES (20.0 µg/ml), or LPS (10 ng/ml). Following incubation, cells were washed and stained with antibodies specific for CD80, CD86, CCR5, CD40, and MHC Class II, or with isotype matched controls. Cells were then analysed using a flow cytometer.
Figure 21B:
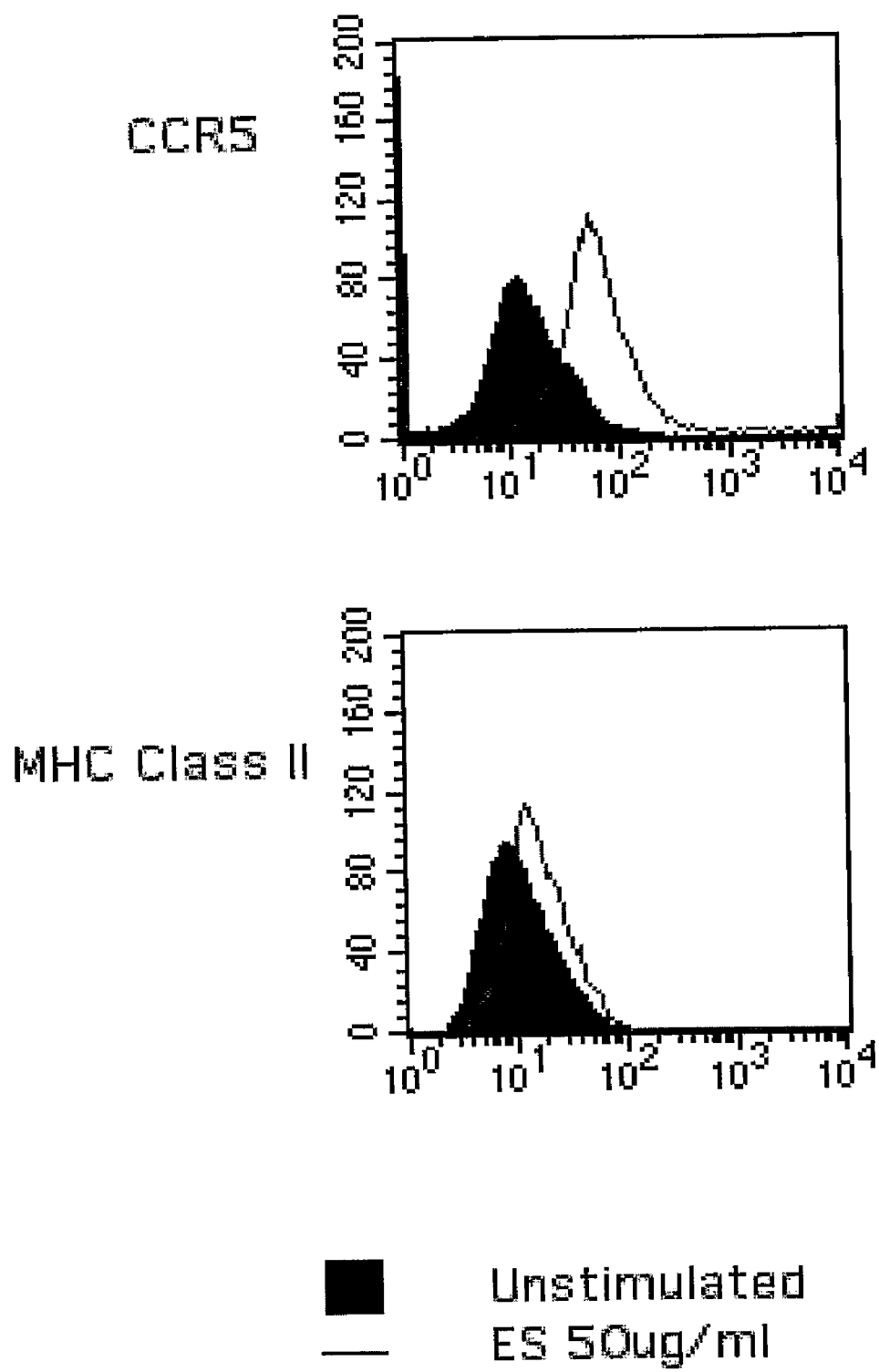
Figure 22A:
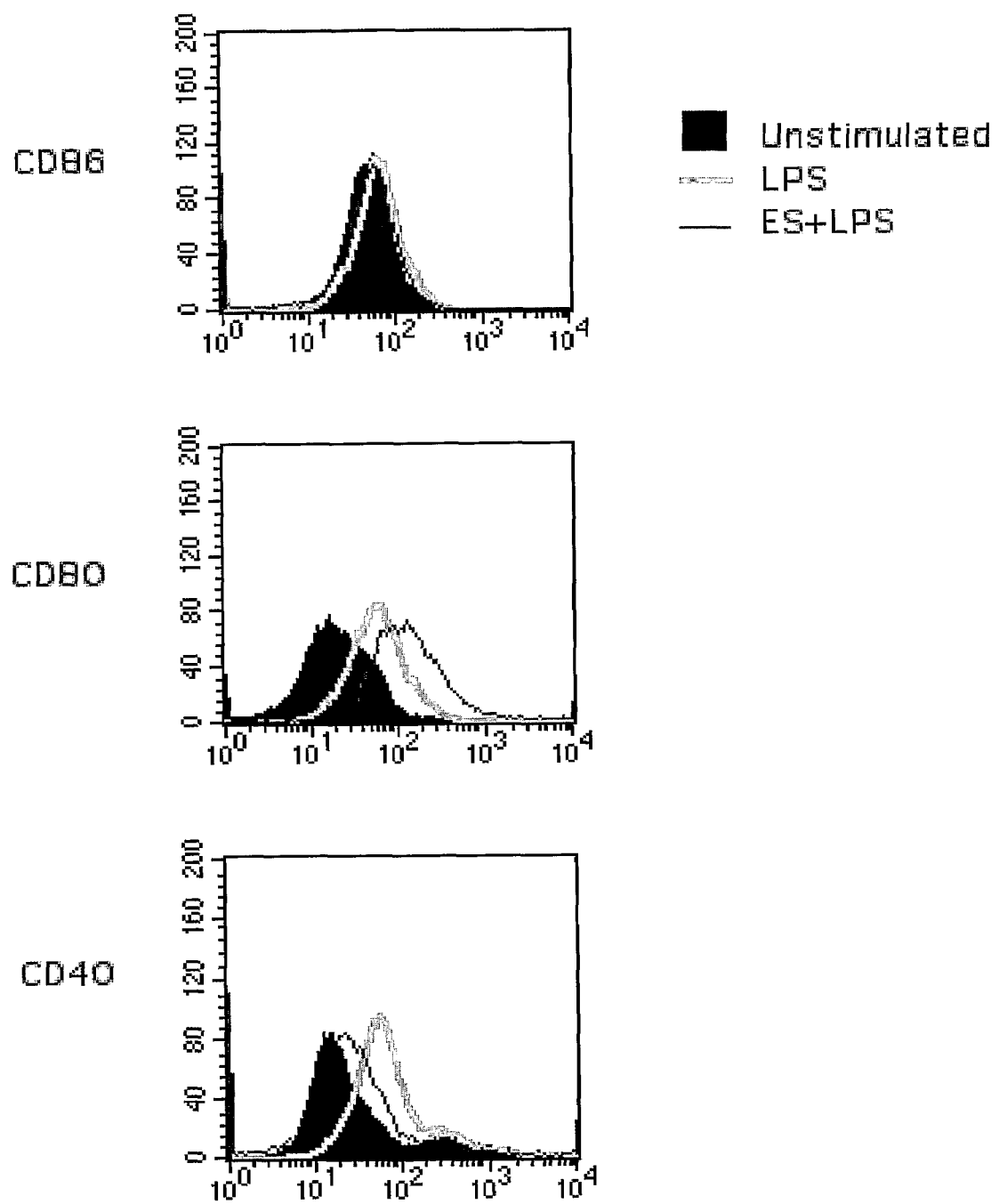
FIG. 22 shows that ES suppresses LPS-induced CD40 expression on macrophages. J774 macrophages ($1\times10^6$/ml) were stimulated for 24 hours with medium only, LPS (10 ng/ml), ES (20.0 µg/ml), or LPS following a 2 hour pre-incubation with ES. Following incubation, cells were washed and stained with antibodies specific for CD80, CD86, CCR5, CD40, and MHC Class II, or with isotype-matched controls. Cells were then analysed using a flow cytometer.
Figure 22B:
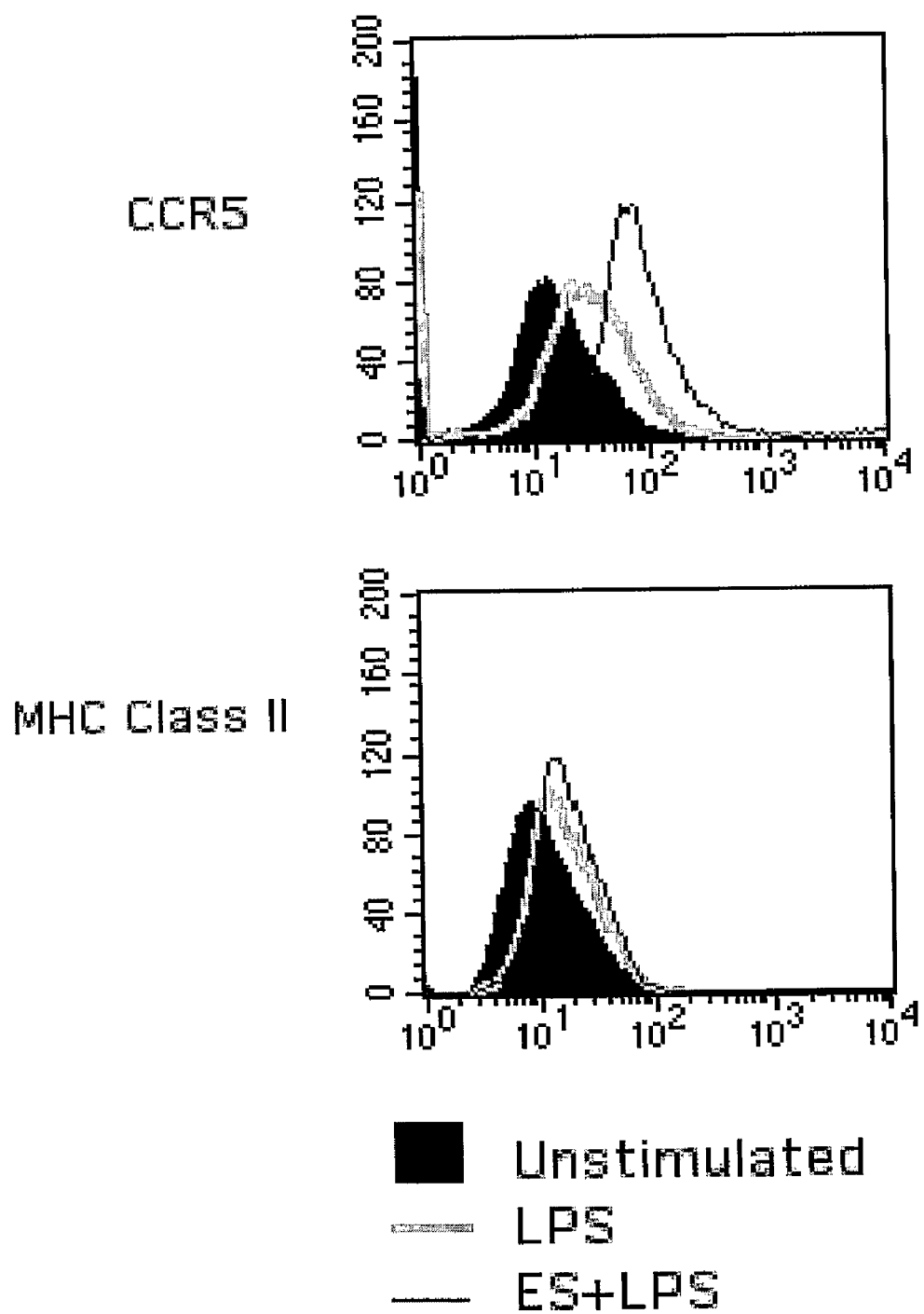

ES also enhanced surface expression of CD80, CD86, CD40, CCR5 and MHC class II on J774 macrophages (FIG. 21) and enhanced LPS-induced expression of these markers, except for CD40 which was inhibited by ES (FIG. 22). Suppressed CD40 expression has been associated with induction of Treg cells. These finding therefore suggest that ES induces maturation of DC and macrophages into an intermediate phenotype, consistent with their ability to prime Treg cells.

ES Induced IL-10 Producing Treg Cells and Suppresses Proliferation and IFN-γ Production by Effector T Cells.

Figure 23A:
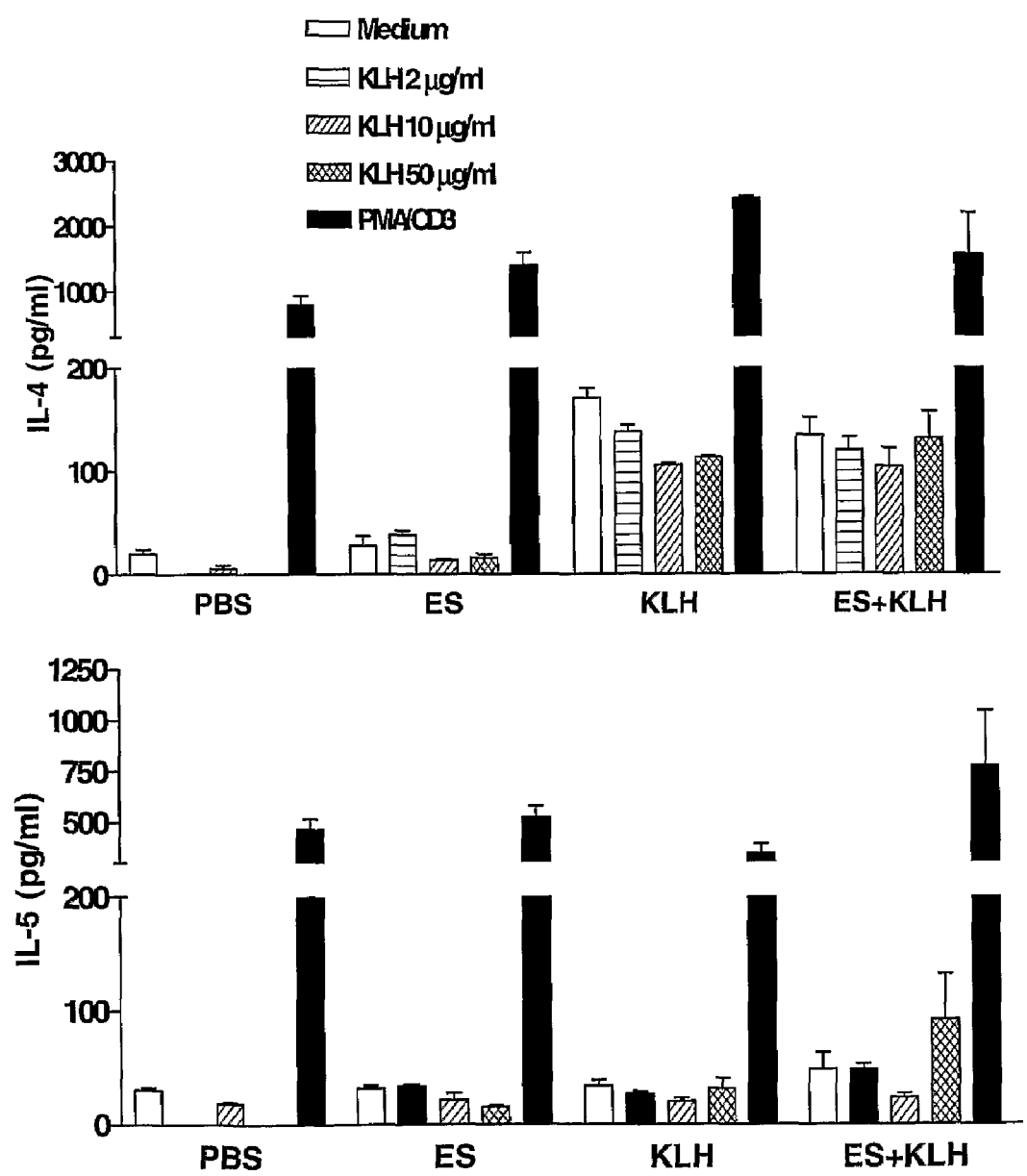
FIG. 23 shows that ES enhances antigen-specific IL-10 production to co-administered antigen. BALB/c mice were immunized subcutaneously in the flank with PBS, (20 µg), KLH (5 µg), or KLH (5 µg) and ES (20 µg). After 7 days, inguinal lymph nodes were isolated and stimulated with KLH (2-50 µg/ml), medium alone and PMA and anti-CD3 and negative and positive controls respectively. Supernatants were removed after 3 days and tested for IL-4, IL-5, IFN-γ, and IL-10 production by immunoassay.
Figure 23B:
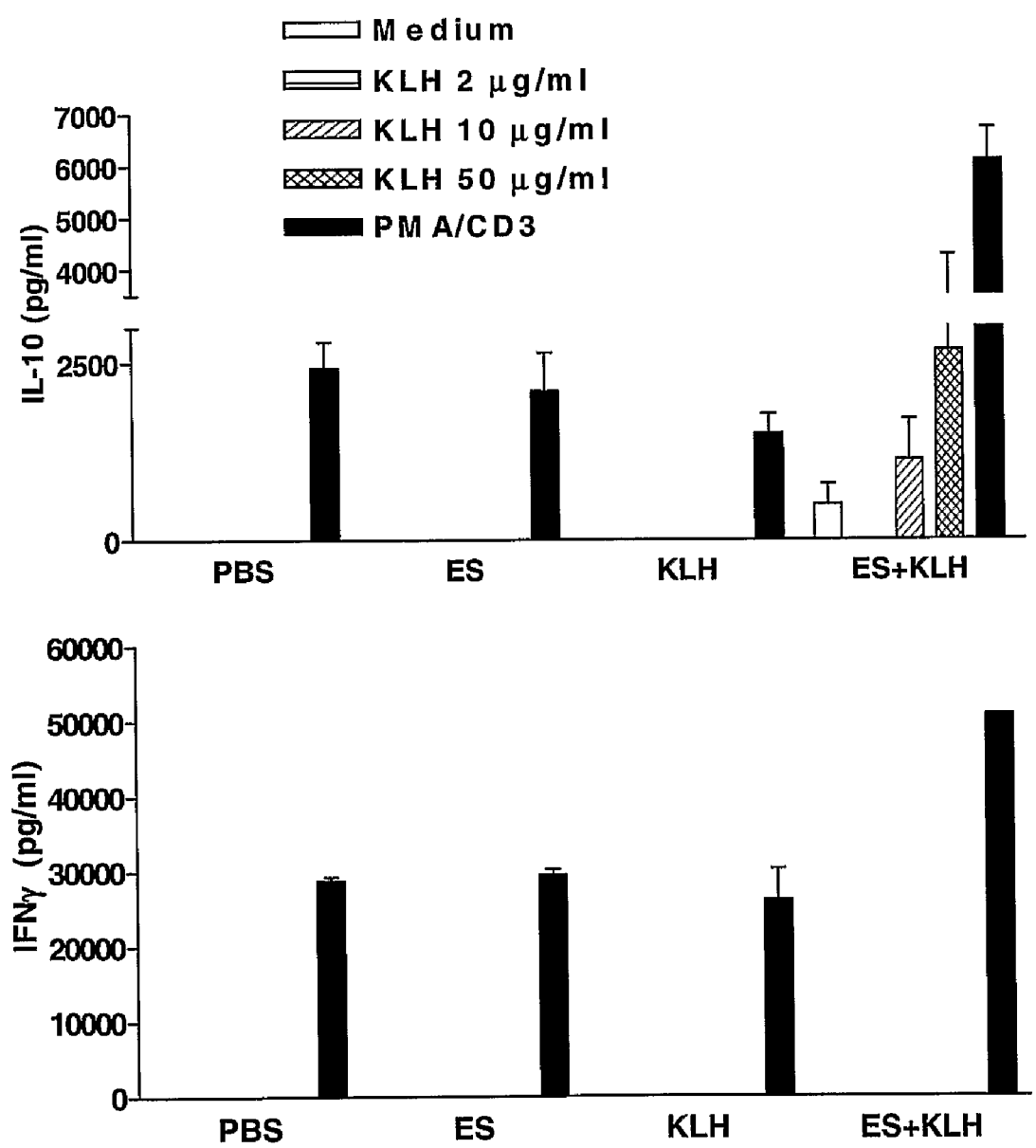
Figure 24A:
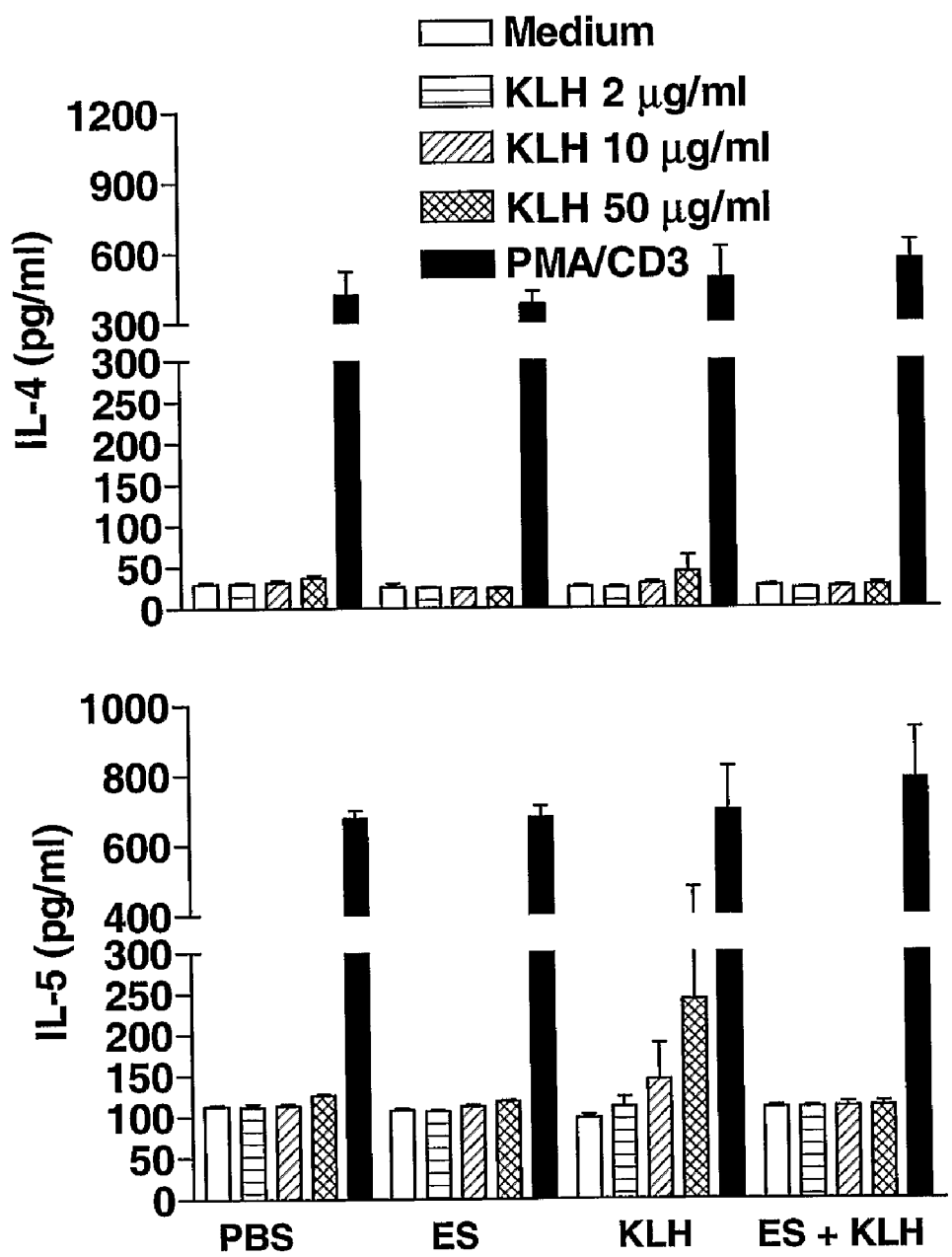
FIG. 24 shows that ES suppresses antigen-specific T cell responses to co-administered antigen. BALB/c mice were immunised subcutaneously in the flank with PBS, ES (50 µg). KLH (5 µg), or KLH (5 µg) and ES (50 µg). After 7 days, inguinal lymph nodes were isolated and stimulated with KLH (2-50 µg/ml), medium alone and PMA and anti-CD3 and negative and positive controls respectively. Supernatants were removed after 3 days and tested for IL-4, IL-5, IFN-γ, and IL-10 by immunoassay.
Figure 24B:
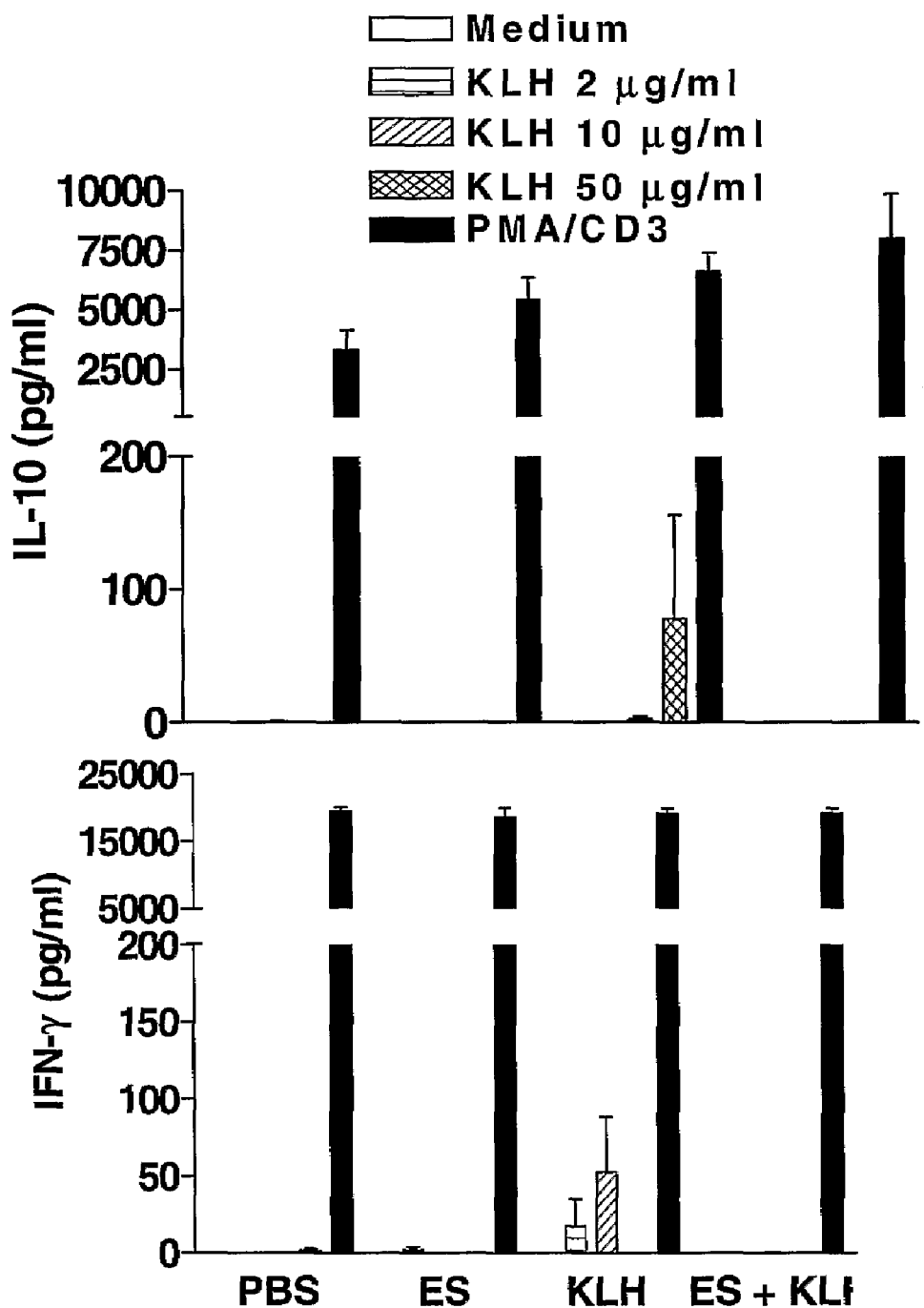

We examined the influence of ES on the induction of T cell responses to a model antigen, KLH. Mice were injected with ES only, KLH only or KLH and ES and draining lymph nodes were removed after 7 days and cells re-stimulated with antigen (KLH) in vitro. In this experiment, KLH alone did not induce and antigen-specific immune responses, although responses were detected against the positive control stimulus, anti-CD3 and PMA. In contrast, co-injection with ES (50 μg) generated T cells that secreted high concentrations of antigen-specific IL-10 and lower concentrations of IL-5, but no IL-4 or IFN-γ (FIG. 23). This cytokine patterns is consistent with the induction of Treg cells. In another experiment, where we did detect IL-5 and IFN-γ in response to immunization with KLH alone, we observed suppression of this KLH-specific cytokine production following co-administration of ES (20 μg) (FIG. 24).

Figure 25:
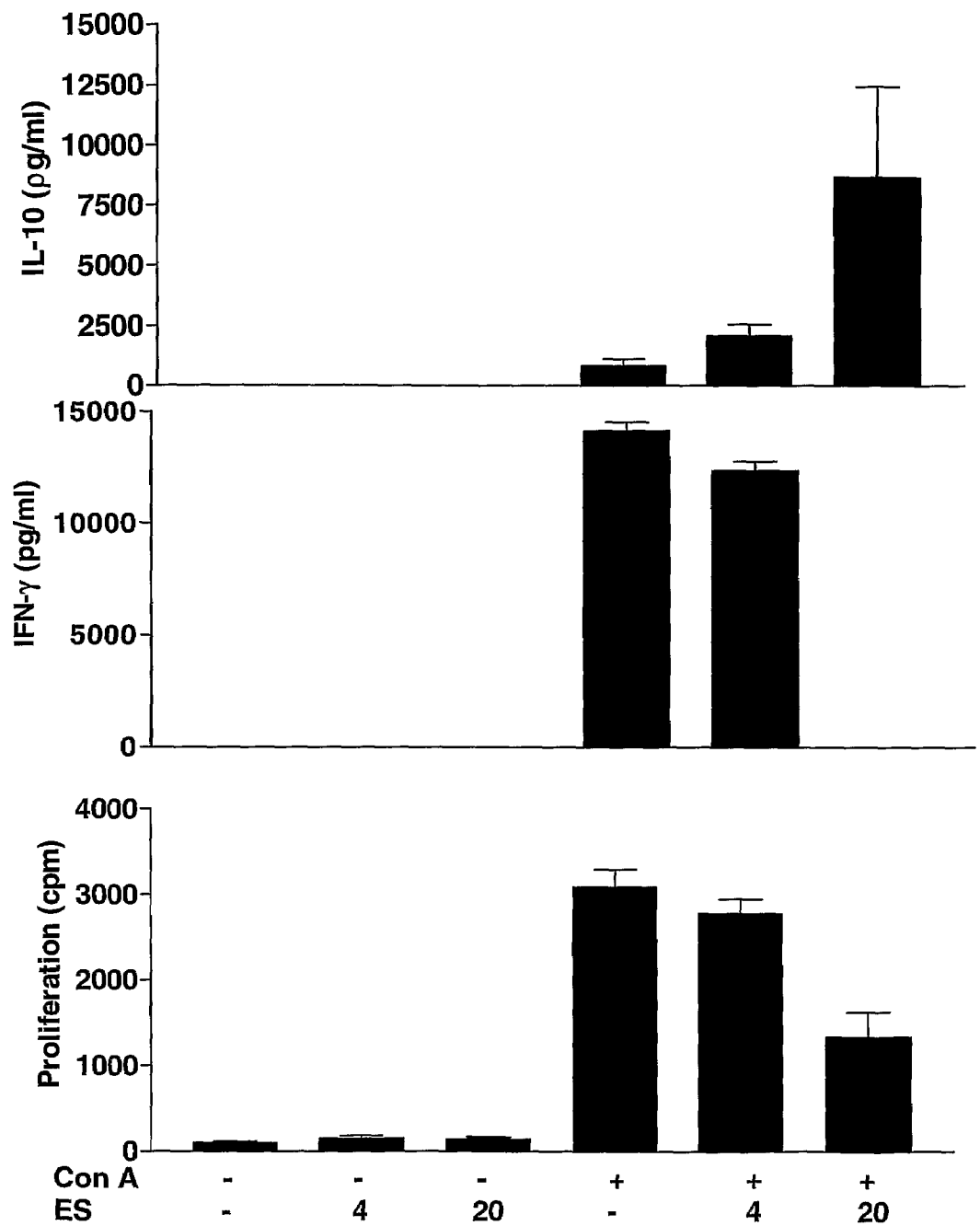
FIG. 25 shows that ES inhibits Con A-induced proliferation and IFN-γ production. Spleen cells ($2\times10^6$/ml) were stimulated for 24 hours with medium or ES (4.0 and 20 µg/ml) only, or in the presence of Con A (5 µg/ml). Supernatants were removed after 72 hours incubation and assessed for IL-10 and IFN-γ production by ELISA. Proliferation was determined after 48 hrs days by [$^3$H] thymidine incorporation.

We also examined the influence of ES on T cell response to the mitogen, Concanavlin A (Con A) in vitro. Spleen cells stimulated with Con A proliferated and secreted IFN-γ and low concentrations of IL-10 (FIG. 25). Co-incubation with ES, especially at the higher concentration used (20 μg/ml), which did not induce proliferation or cytokine production alone, markedly inhibited Con A-induced proliferation and IFN-γ production, but enhanced IL-10. These findings confirm that ES preferentially induces IL-10 secreting T cells and suppresses the induction of Th1 cells.

*F. hepatica* Infection or Parenteral Administration of ES Protects Against Experimental Autoimmune Encephalomyelitis (EAE).

Figure 26:
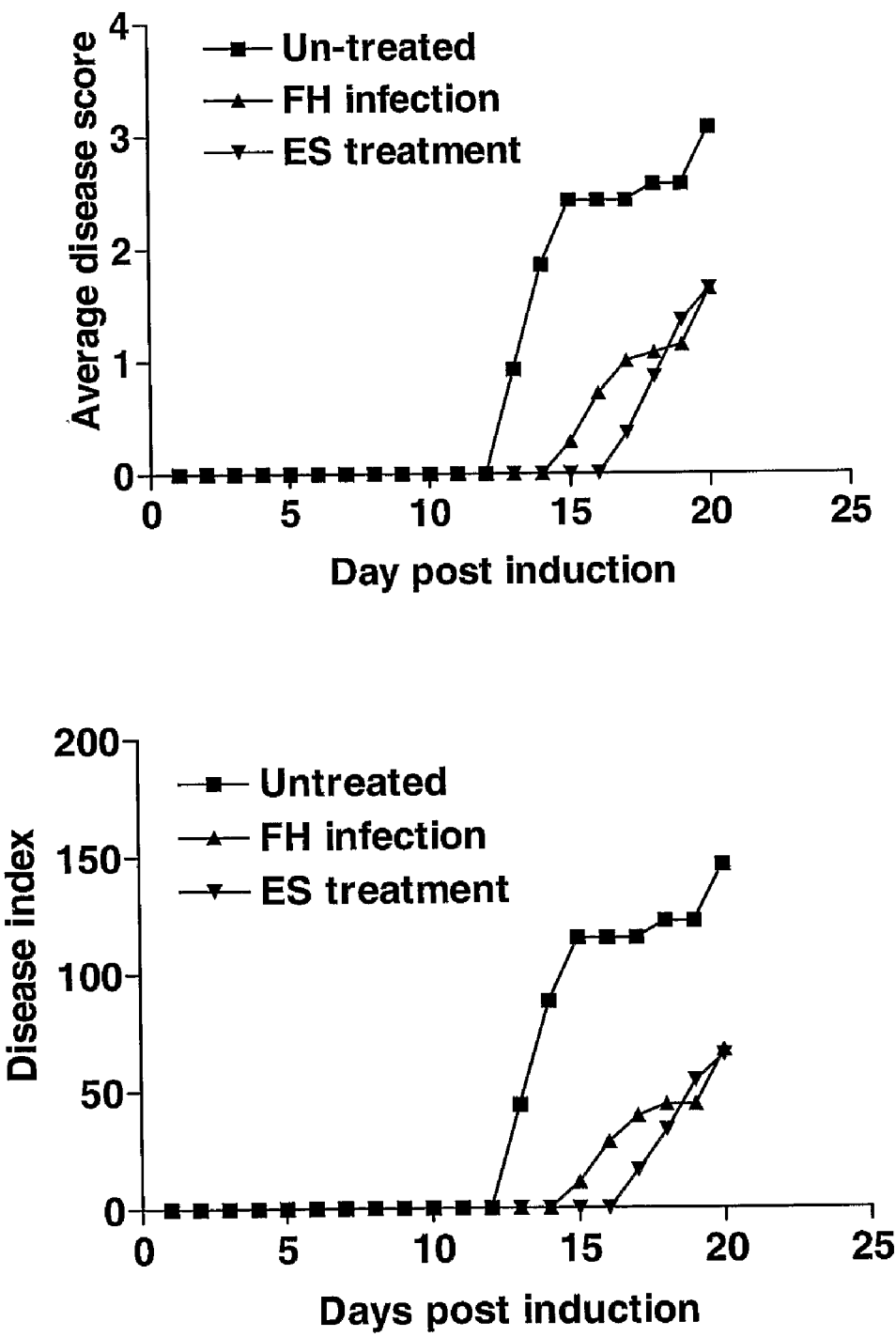
FIG. 26 shows that infection with *F. hepatica* and treatment with *F. hepatica* ES ameliorates clinical symptoms of EAE. EAE was induced in C57BLU6 mice by immunization with MOG35-55 peptide in complete Freund's adjuvant (CFA) on day 0 and injection of pertussis toxin days 0 and 2. One group of mice was left untreated. A second group was infected with 10 metacercariae of *F. hepatica* one day before induction of EAE. A third was injected i.p. with 50 µg ES, one day before induction of EAE and every second day thereafter.

Self-antigen-specific T cells that secrete IFN-γ and IL-17 mediated pathology in a number of autoimmune diseases, including experimental autoimmune encephalomyelitis (EAE), a murine model of multiple sclerosis. T cell mediated autoimmune diseases are controlled in normal individuals by natural and inducible Treg cells that suppress pathogenic T cells. Having shown that *F. hepatica* infection and ES induces IL-10-secreting Treg cells, we examined the influence of the infection or parenteral administration of EAE on the development of EAE in chronic disease model, involving administration of myelin oligodendrocyte glycoprotein (MOG) peptide in complete Freund's adjuvant (CFA) with pertussis toxin (PT). Untreated mice developed clinical symptoms of EAE after 12 days and reached a clinical score of grade 3 or above after 20 days and had to be sacrificed at this stage. In contrast, *F. hepatica* infected mice did not develop symptoms until day 14 and ES treated until day 16 (FIG. 26). Furthermore the severity of disease in these mice was considerably reduced. These findings demonstrate that parenteral delivery of ES has a protective effect against autoimmune disease in mice.

*F. hepatica* Infection or Parenteral Administration of ES Suppresses Induction of Pathogenic T Cells During Development of EAE.

Figure 27A:
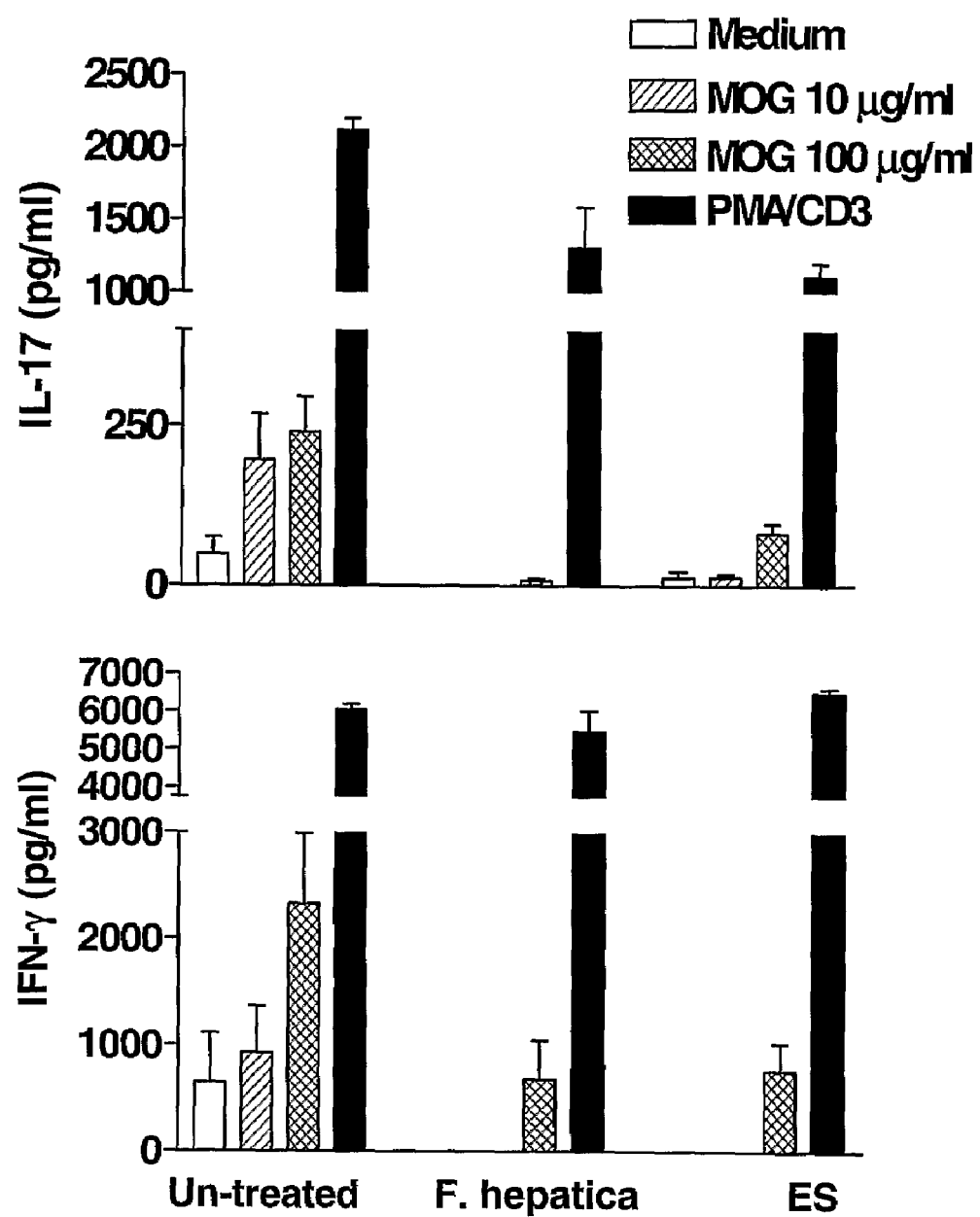
FIG. 27 shows that infection with *F. hepatica* and treatment with *F. hepatica* ES suppresses induction of pathogenic IL-17 and IFN-γ-secreting T cells. EAE was induced in C57BU6 mice by immunization with MOG35-55 peptide in CFA on day 0 and injection of pertussis toxin days 0 and 2. One group of mice was left untreated. A second group was infected with 10 metacercariae of *F. hepatica* one day before induction of EAE. A third was injected i.p. with 50 µg ES, one day before induction of EAE and every second day thereafter. 20 days after induction of EAE, mice were sacrificed and spleen removed. Spleen cells ($2\times10^6$/ml) were stimulated with medium only, MOG35-55 peptide (10 and 100 µg/ml), or anti-CD3 and PMA. Supernatants were removed after 3 days and IL-17, IFN-γ, IL-4 and IL-10 concentrations determined by ELISA.
Figure 27B:
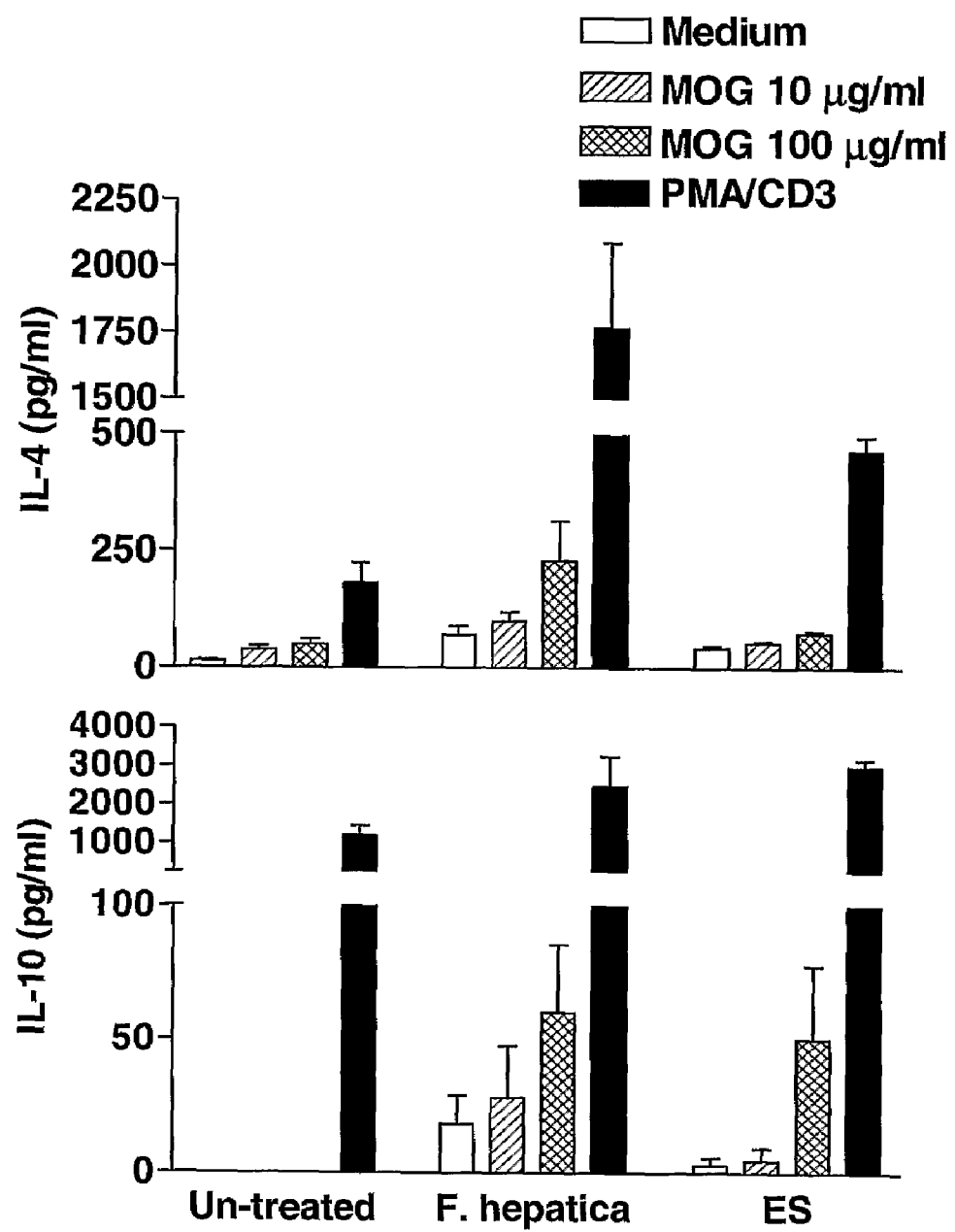

T cells mediate many autoimmune diseases and it has traditionally been considered that IFN-γ-secreting Th1 cells are responsible for the inflammatory pathology. However recent evidence suggests that IL-17-secreting T cells mediate much of the damage in many chronic inflammatory and autoimmune diseases, including rheumatoid arthritis, colitis, multiple sclerosis and EAE, the murine model for multiple sclerosis. Here that development of EAE was associated with the induction of MOG-specific IL-17 and IFN-γ-secreting T cells in untreated mice (FIG. 27). Infection with *F. hepatica* or parenteral administration of ES (which reduced clinical symptoms of EAE) suppressed the induction of MOG-specific IL-17 and IFN-γ producing T cells. Furthermore IL-17 production in response to the polyclonal stimuli, anti-CD3 and PMA, was also suppressed in infected or ES-treated mice. In contrast, MOG-specific IL-10 was undetectable in untreated mice, but was detectable at significant concentrations in mice infected with *F. hepatica* or treated with ES. Furthermore, MOG-specific IL-4 was enhanced in *F. hepatica* infected mice. In addition anti-CD3 and PMA induced IL-4 and IL-10 was enhanced in infected and ES-treated mice. These finding demonstrate that infection with *F. hepatica* or therapy with ES prevents induction of EAE by enhancing the anti-inflammatory cytokine, IL-10 and suppressing autoantigen-specific pathogenic IL-17 and IFN-γ secreting T cells.

*Fasciola hepatica* Infection Slows the Onset and Attenuates the Clinical Signs of EAE in C57BU6 Wildtype and IL-10-Defective Mice.

Figure 28:
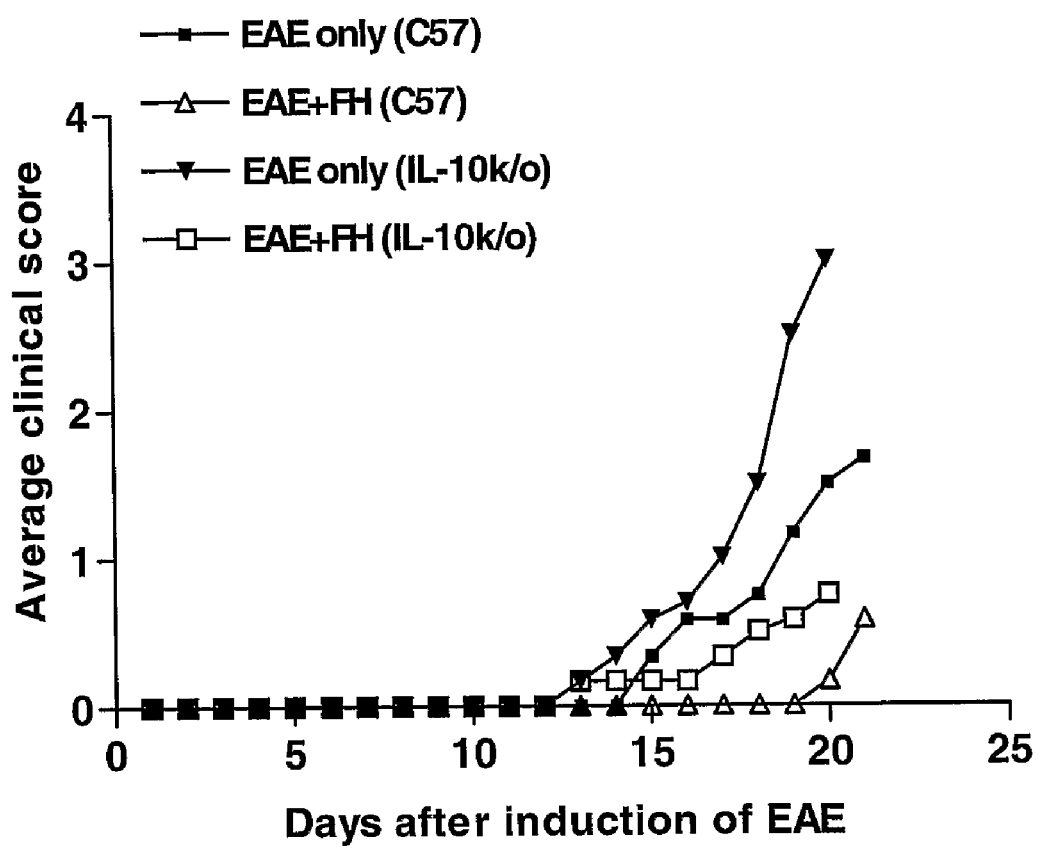
FIG. 28 shows that *Fasciola hepatica* infection slows the onset and attenuates the clinical signs of EAE in C57BL/6 wildtype and IL-10-defective mice. EAE was induced in C57BU6 or IL-10 knockout mice by immunization with $MOG_{35-55}$ peptide in complete Freund's adjuvant (CFA) on day 0 and injection of pertussis toxin days 0 and 2. In each strain of mice, one group were left untreated, and a second group were administered 10 metacercariae of *F. hepatica* 1 day before EAE induction.

FIG. 28 shows that *F. hepatica* infection slows the onset and attenuates the clinical signs of EAE in C57BL/6 wildtype and IL-10-defective mice, suggesting that the attenuation of EAE by *F. hepatica* is not mediated by IL-10 induction.

*F. hepatica* Infection Inhibits Pathogenic IFN-γ and IL-17 Secreting Cells During EAE by an IL-10-Independent Mechanism.

Figure 29A:
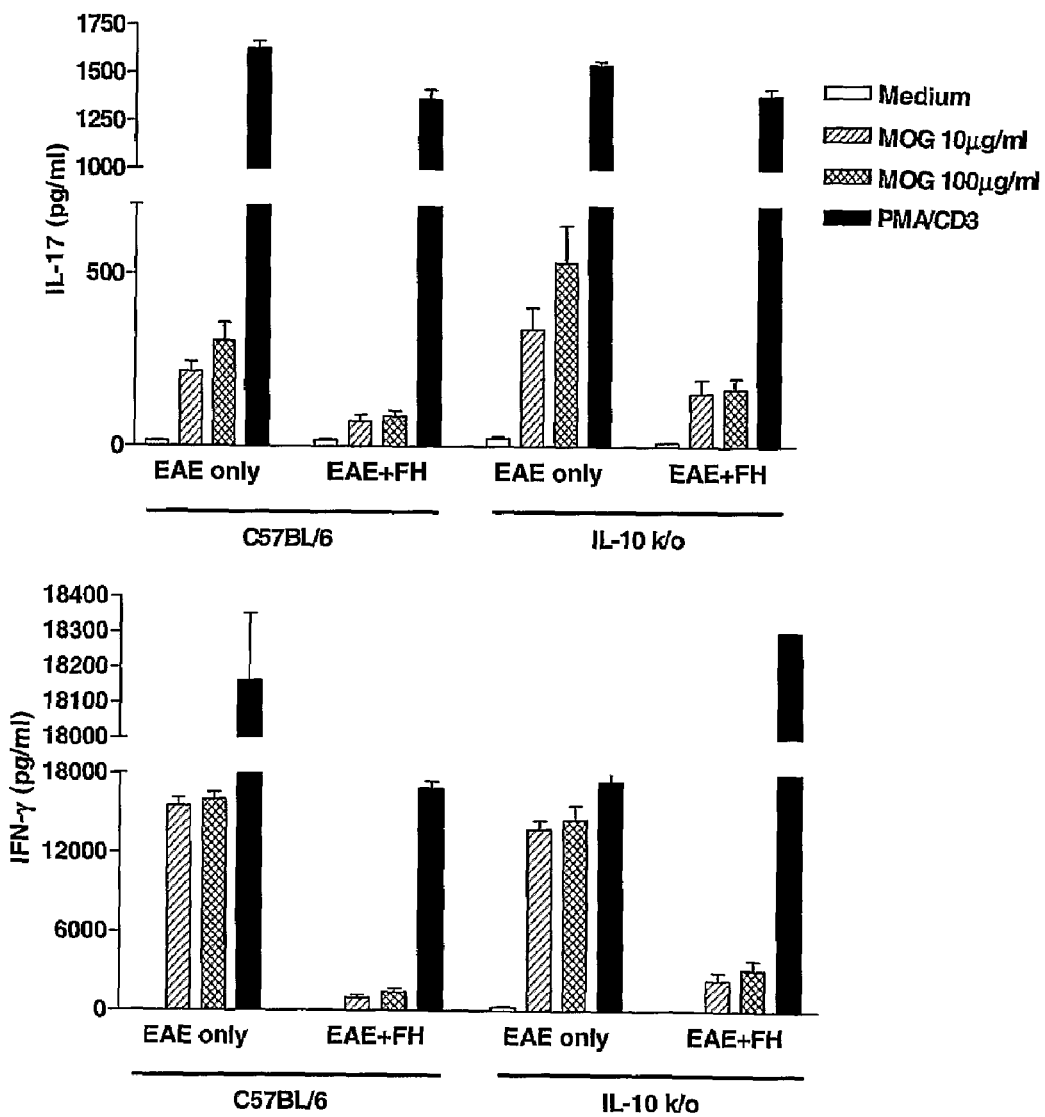
FIG. 29 shows that *F. hepatica* infection inhibits pathogenic IFN-γ and IL-17 secreting cells during EAE by an IL-10-independent mechanism. EAE was induced in C57BU6 or IL-10 knockout (k/o) mice by immunization with $MOG_{35-55}$ peptide in complete Freund's adjuvant (CFA) on day 0 and injection of pertussis toxin days 0 and 2. In each strain of mice, one group were left untreated, and a second group were administered 10 metacercariae of *F. hepatica* 1 day before EAE induction. 20 days (for IL-10k/o) or 23 days (for WT mice) after induction of EAE, mice were sacrificed and spleens removed. Spleen cells ($2\times10^6$/ml) were stimulated with medium only, $MOG_{35-55}$ peptide (10 and 100 µg/ml), or anti-CD3 and PMA. Supernatants were removed after 3 days and IL-17, IFN-µ, IL-4 and IL-10 concentrations determined by ELISA.
Figure 29B:
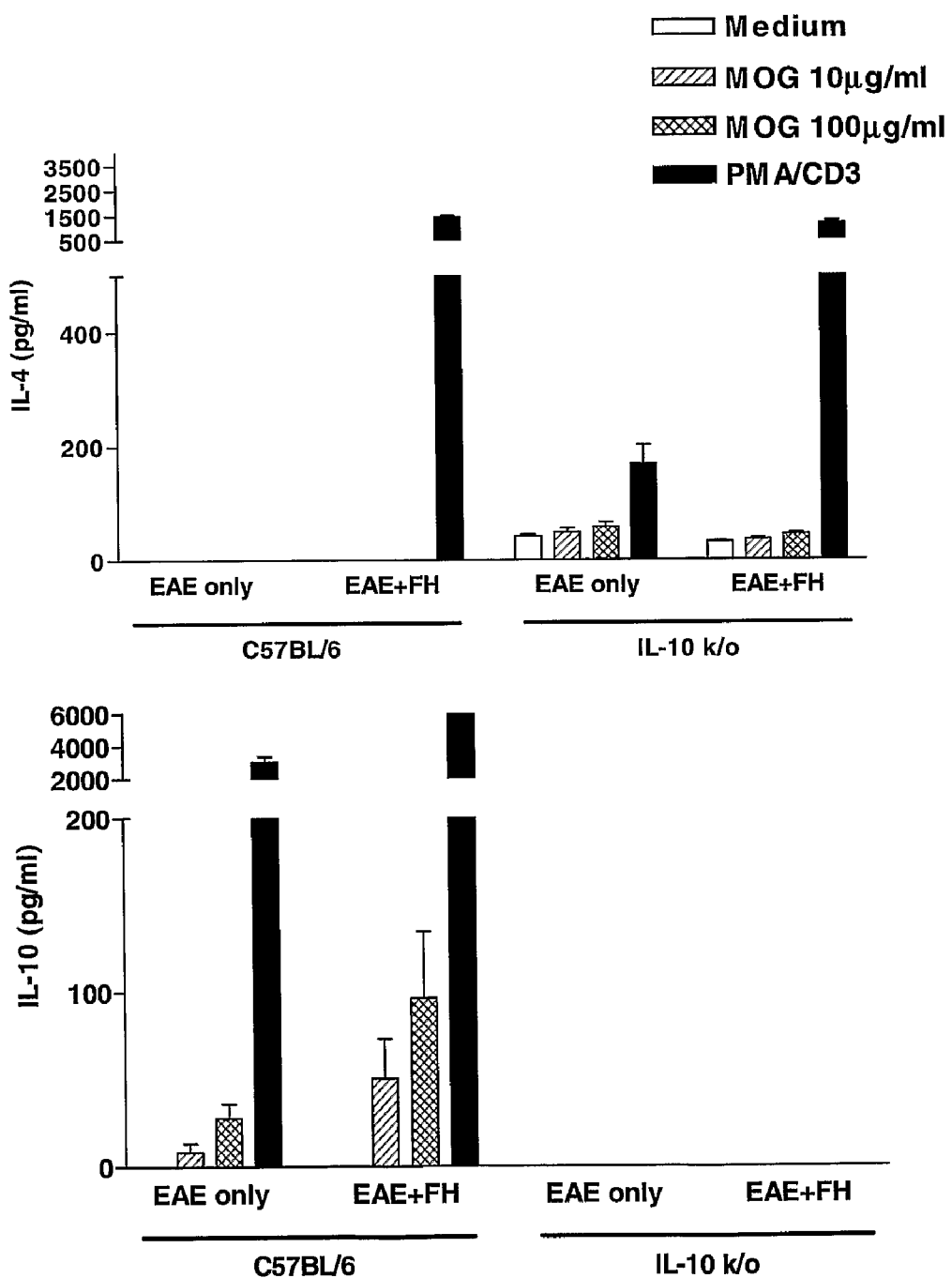

FIG. 29 shows that *F. hepatica* infection inhibits MOG-specific IL-17 and IFN-γ production in C57BU6 wildtype and IL-10-defective mice and enhances IL-10 production in wildtype mice. The data suggest that the inhibition of pathogenic T cells by *F. hepatica* infection is not mediated by IL-10.

*Fasciola hepatica* Infection Attenuates Clinical Signs of DSS-Induced Colitis in BALB/c Mice.

Figure 30:
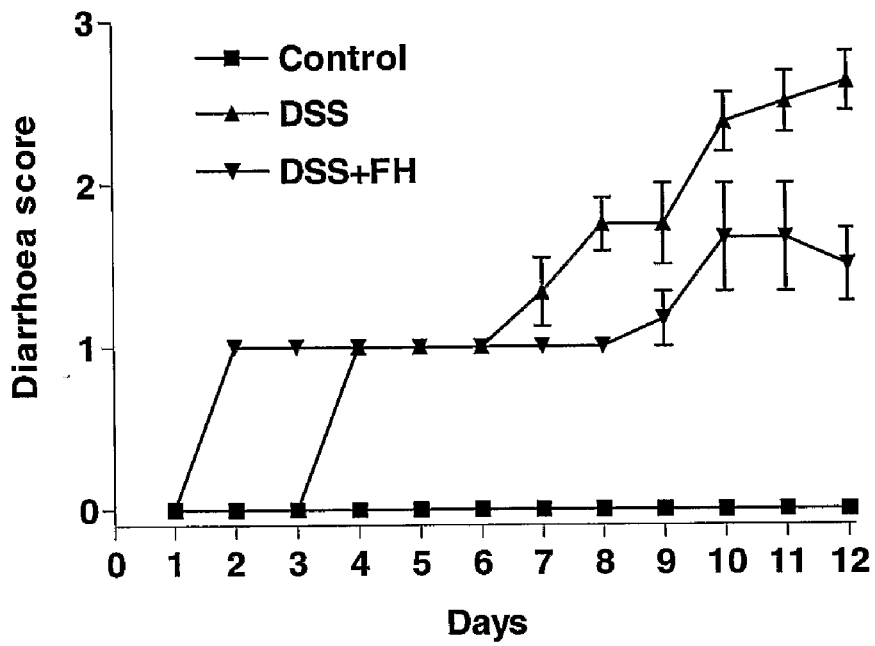
FIG. 30 shows that *Fasciola hepatica* infection attenuates clinical signs of DSS-induced colitis in BALB/c mice. Colitis was induced in BALB/c mice by administering 5% Dextran sulphate (DSS) in the drinking water from day 0, for the duration of the experiment. One group of mice were left untreated, and a second group were administered 10 metacercariae of *F. hepatica* 5 days before administration of DSS. An additional group of mice that did not receive DSS or *F. hepatica* infection severed as controls. The clinical symptoms of colitis were monitored by daily observation of A) diarrhea (scores 1-3 as follows: 0, normal pellets; 1, slightly loose pellets; 2, loose pellets; 3, watery diarrhea) and B) fecal blood (Scored as follows: 0, normal; 1, slightly bloody; 2, bloody; 3, blood in whole colon).
Figure 30:
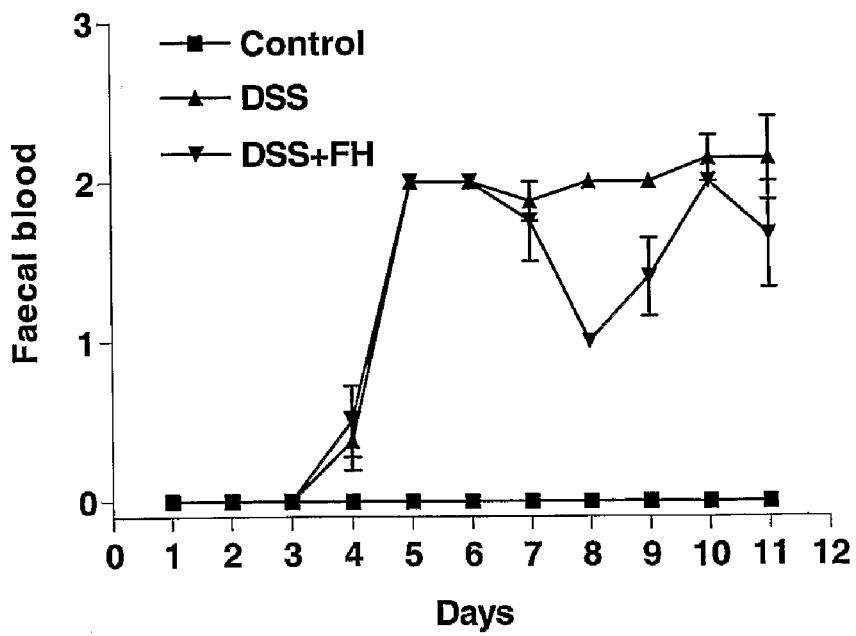

FIG. 30 shows that *Fasciola hepatica* infection attenuates clinical signs of colitis (diarrhoea and bloody stools) induced by DSS in BALB/c mice.

Figure 31:
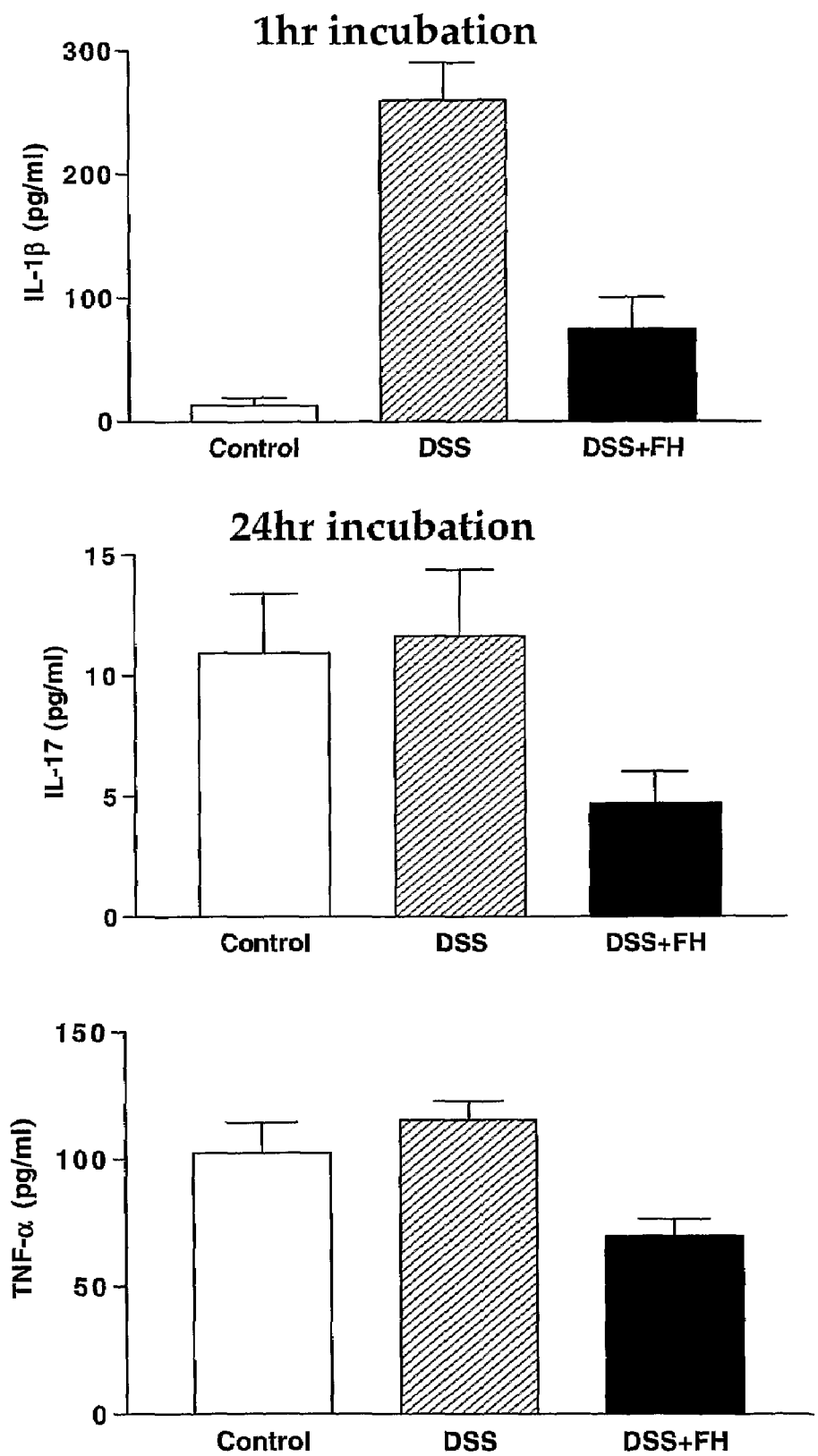
FIG. 31 shows that *Fasciola hepatica* infection suppresses pro-inflammatory cytokines production in the colon during DSS-induced colitis. Colitis was induced in BALB/c mice by administering 5% Dextran sulphate (DSS) in the drinking water from day 0, for the duration of the experiment. One group of mice were left untreated, and a second group were administered 10 metacercariae of *F. hepatica* 5 day before administration of DSS. An additional group of mice that did not receive DSS or *F. hepatica* infection severed as controls. Mice were sacrificed on day 12, colons removed, treated for 1 hour with proteolytic enzymes and then incubated for 1 or 24 hours. The concentration of IL-1β, IL-17 and TNF-α in the tissue supernatants was determined by ELISA.

*Fasciola hepatica* Infection Suppresses Pro-Inflammatory Cytokines Production in the Colon During DSS-Induced Colitis FIG. 31 shows that the induction of IL-1β, IL-17 and TNF-α in the colon during DSS-induced colitis is reduced following infection with *Fasciola hepatica*. These cytokines have been shown to mediate pathology in colitis and the data suggest that *F. hepatica* confers a level of protection by inhibiting production of pro-inflammatory cytokines.

Figure 32A:
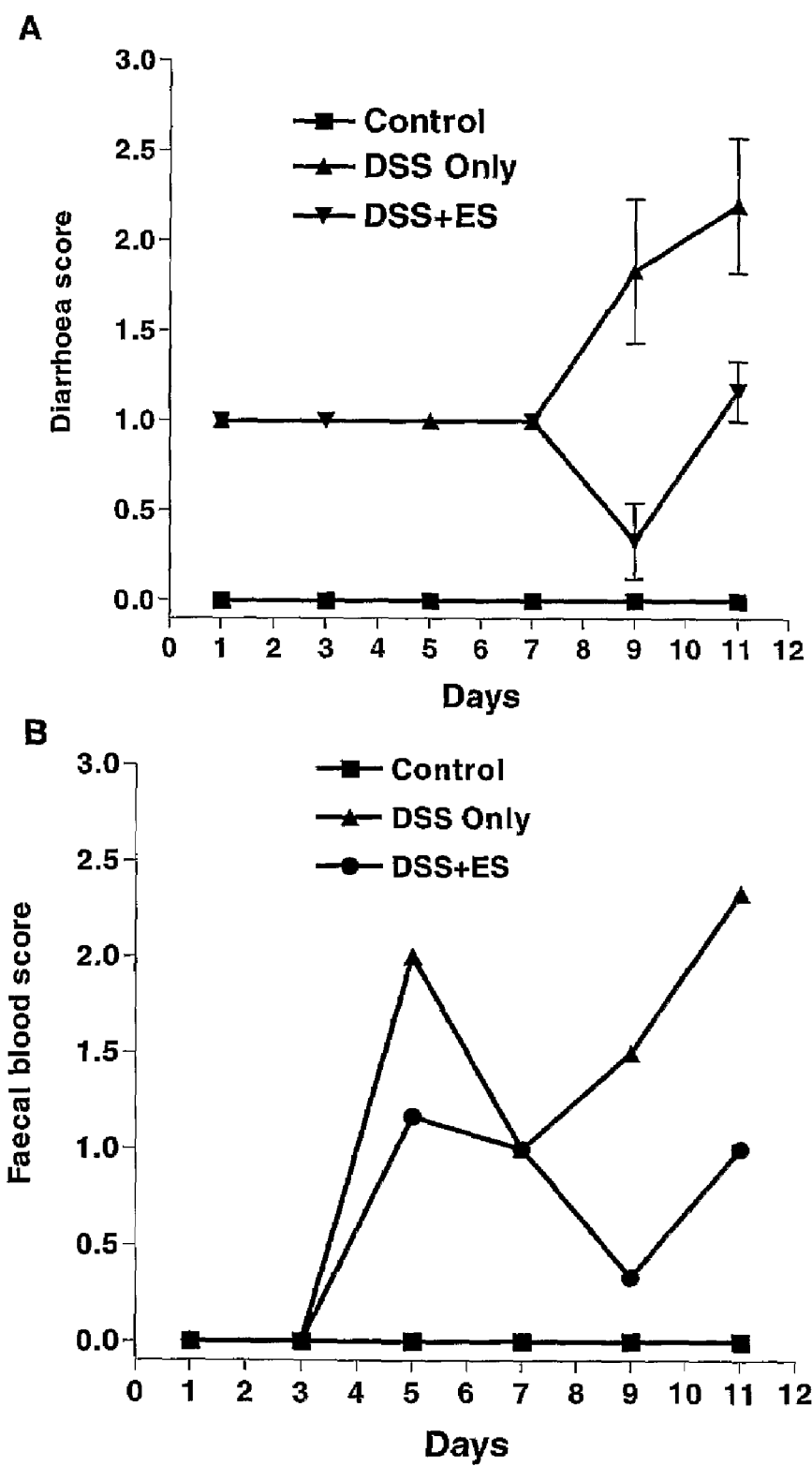
FIG. 32 shows that therapy with *Fasciola hepatica* ES products attenuates clinical signs of DSS-induced colitis in BALB/c mice. Colitis was induced in BALB/c mice by administering 5% Dextran sulphate (DSS) in the drinking water from day 0, for the duration of the experiment. One group of mice were left untreated, and a second group received 50 µg *F. hepatica* ES on days -1, +1, 3, 5, 7 and 9. An additional group of mice that did not receive DSS or *F. hepatica* infection severed as controls. The clinical symptoms of colitis were monitored by daily observation of A) diarrhea (scores 1-3 as follows: 0, normal pellets; 1, slightly loose pellets; 2, loose pellets; 3, watery diarrhoea), B) fecal blood (Scored as follows: 0, normal; 1, slightly bloody; 2, bloody; 3, blood in whole colon) and C) Body weight (expressed as a percentage of weights on day 0).
Figure 32B:
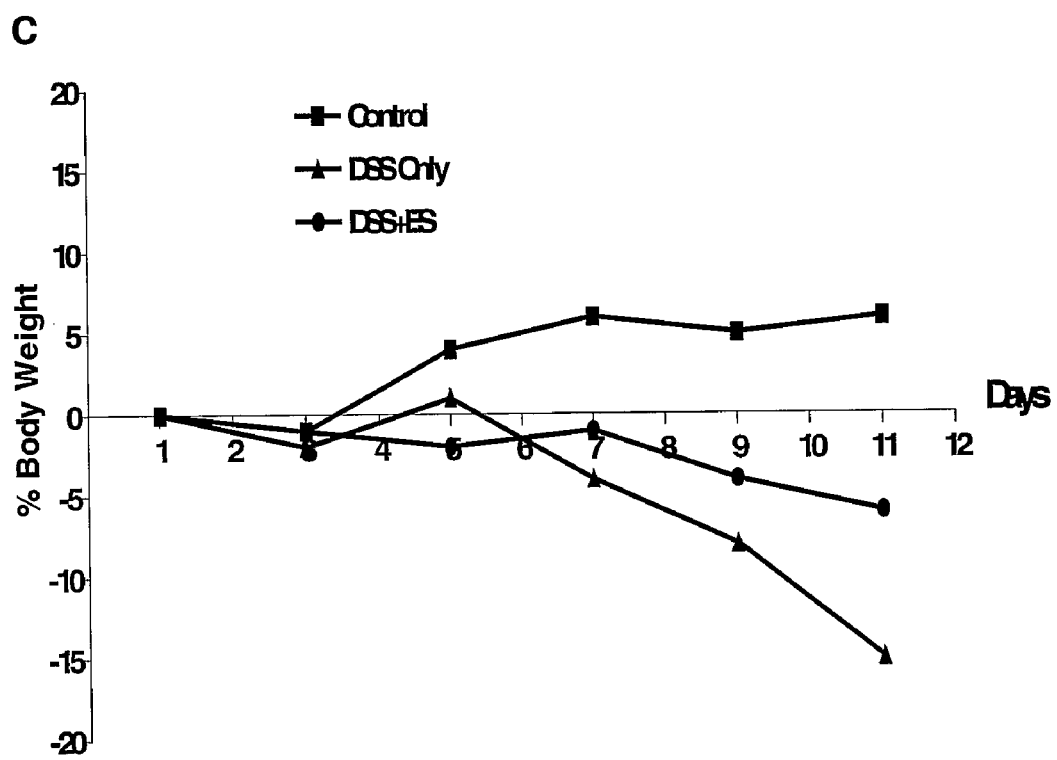

Therapy with *Fasciola hepatica* ES Products Attenuates Clinical Signs of DSS-Induced Colitis in BALB/c Mice FIG. 32 shows that parenteral administration of *Fasciola hepatica* ES products attenuates clinical signs of colitis (diarrhoea, bloody stools and weight loss) induced by DSS in BALB/c mice.

Figure 33:
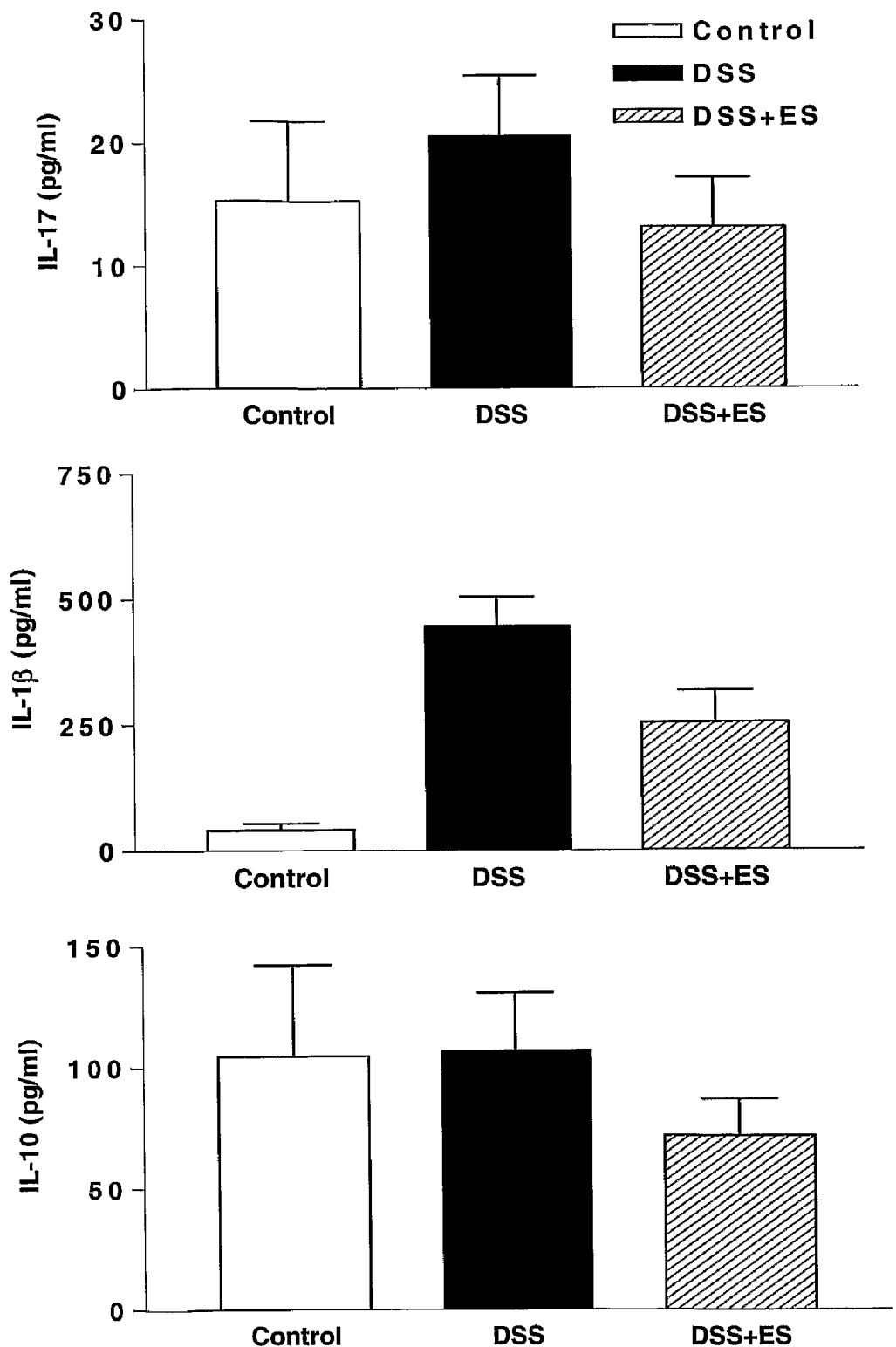
FIG. 33 shows that therapy with *Fasciola hepatica* ES products suppresses pro-inflammatory cytokine production during DSS-induced colitis in BALB/c mice. Colitis was induced in BALB/c mice by administering 5% Dextran sulphate (DSS) in the drinking water from day 0, for the duration of the experiment. One group of mice were left untreated, and a second group received 50 μg *F. hepatica* ES on days −1, +1, 3, 5, 7 and 9. An additional group of mice that did not receive DSS or *F. hepatica* ES severed as controls. Mice were sacrificed on day 12, colons removed, treated for 1 hour with proteolytic enzymes and then incubated for 1 or 24 hours. The concentration of IL-17, IL-1β and IL-10 were determined by ELISA.

Therapy with *Fasciola hepatica* ES Products Suppresses Pro-Inflammatory Cytokine Production During DSS-Induced Colitis in BALB/c Mice FIG. 33 shows that the induction of IL-1β, IL-17 and IL-10 in the colon during DSS-induced colitis is reduced by administration of *Fasciola hepatica* ES products. IL-1 and IL-17 have been shown to mediate pathology in colitis and the data suggest that *F. hepatica* ES products confer a level of protection by inhibiting production of these pro-inflammatory cytokines.

ES Inhibits Antigen-Specific IL-17 and IFN-γ Production to Co-administered Antigen.

Figure 34A:
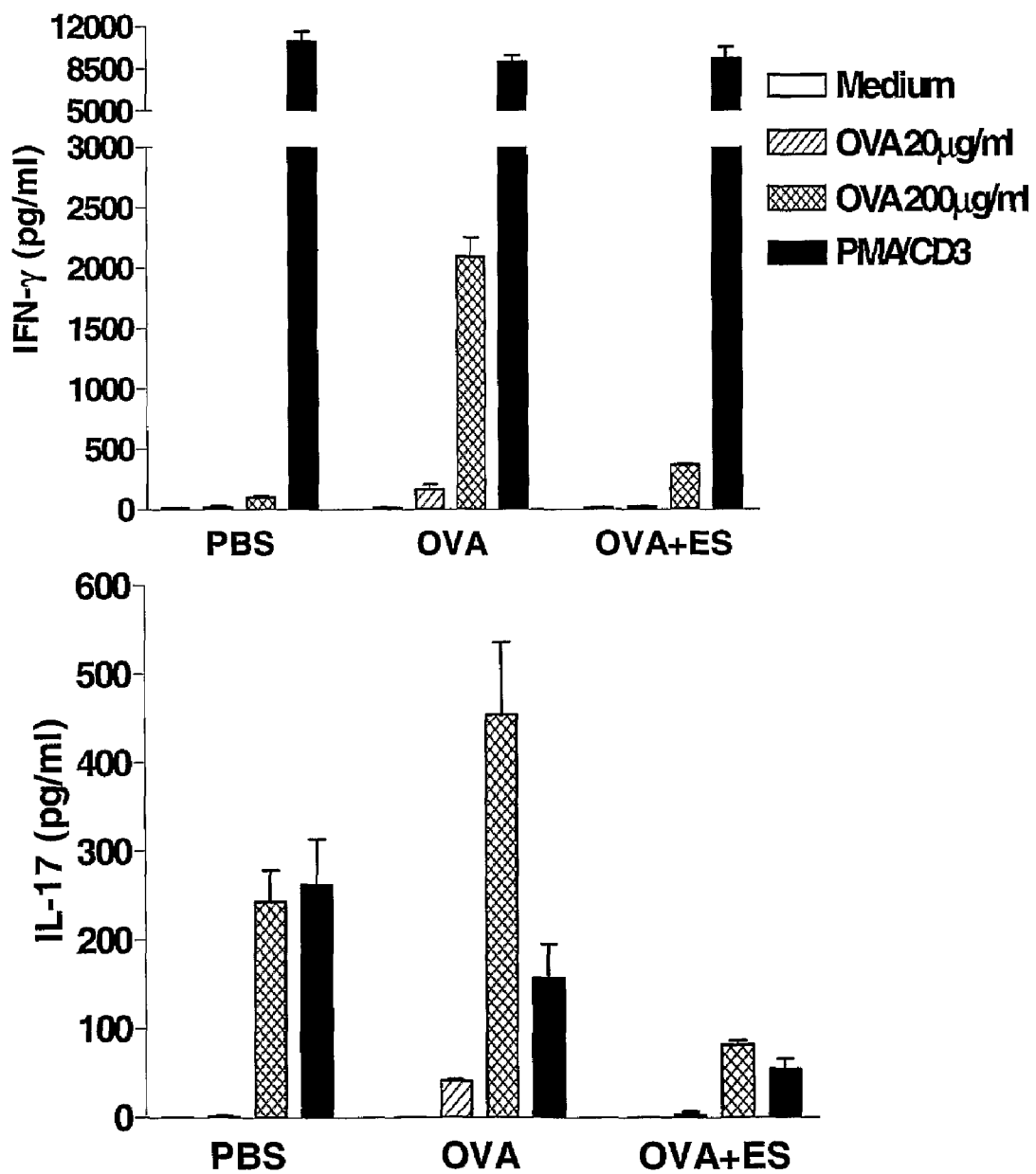
FIG. 34 shows that ES inhibits antigen-specific IL-17 and IFN-γ production to co-administered antigen. OVA-Tg mice were immunized subcutaneously in the flank with PBS, OVA (200 μg) or OVA (5 μg) and ES (50 μg). After 14 days, mice received a secondary immunization with either OVA, or OVA with ES. 7 days after the secondary immunization, inguinal lymph nodes were isolated and stimulated with OVA (20 and 200 μg/ml), medium alone and PMA and anti-CD3 and negative and positive controls respectively. Supernatants were removed after 3 days and tested for IFN-γ, IL-10, IL-17 and IL-5 production by immunoassay.
Figure 34B:
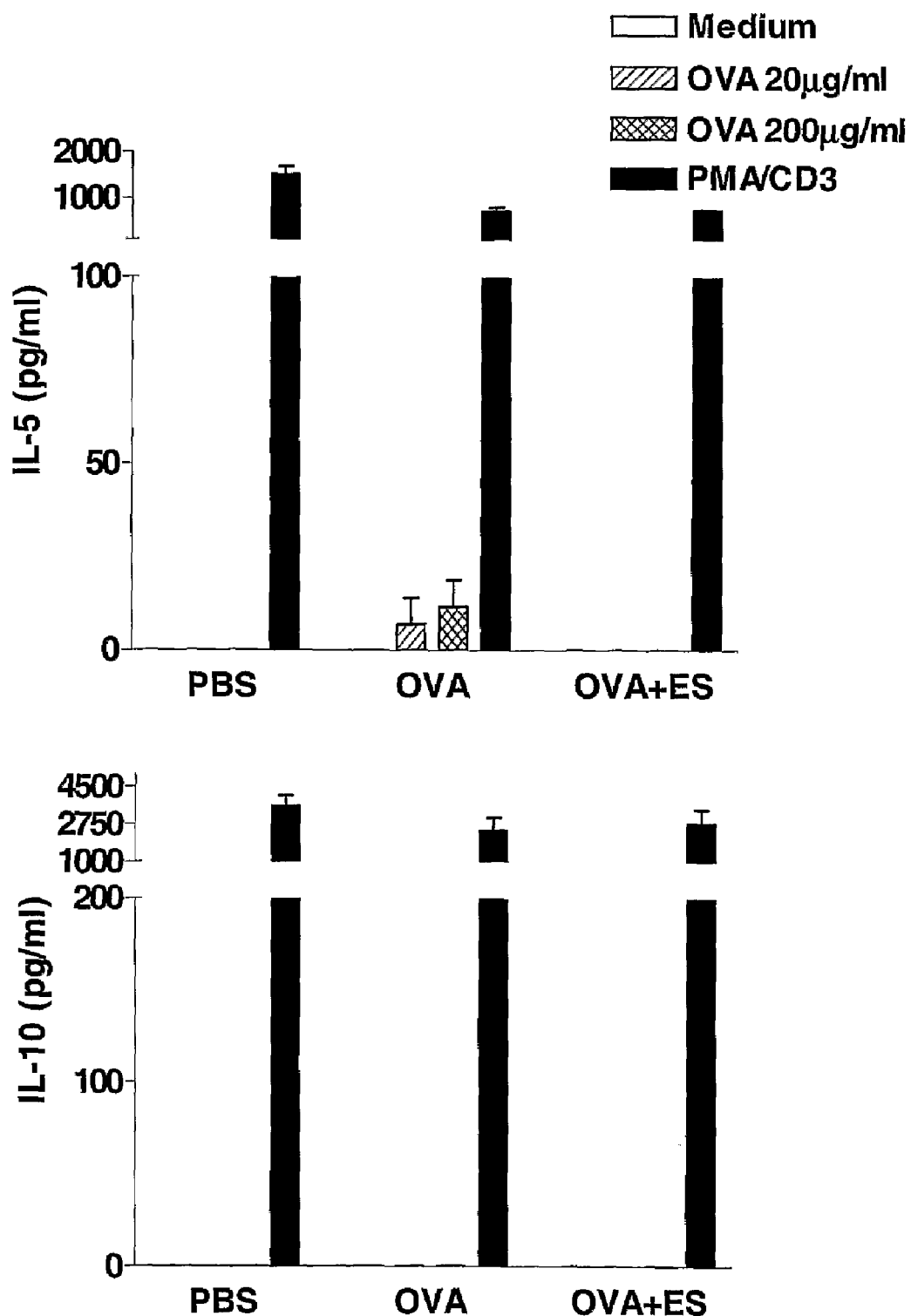

FIG. 34 shows that co-administration of ES with a foreign antigen in vivo suppresses the induction of antigen-specific T cells, in particular T cells that secrete IFN-γ (Th1 cells) or IL-17 (Th17 cells).

SUMMARY

The present inventors have discovered that infection with *F. hepatica* or administration of *F. hepatica* ES to mice induces a high frequency of IL-10 secreting regulatory T (Treg) cells and that ES products have the capacity to inhibit autoimmune diseases. We demonstrated that *F. hepatica* infected mice have a very high frequency of $CD4^+$ T-cells in the peritoneal cavity that secreted very high concentrations of IL-10, in the absence of IL-4. These Treg cells induced by infection inhibited proliferation and IFN-production by OVA-specific T-cells in a co-culture system or when separated by a semi-permeable membrane, indicating soluble factor mediated suppression. Furthermore, dendritic cells (DC) from the peritoneal cavity of *F. hepatica* infected mice secreted high concentrations of IL-10 and had significantly lower cell surface expression of CD80, CD86, CD40 and MHC class II, but higher CCR5, than DC from naïve mice, indicating an immature status. When used as antigen presenting cells for OVA-specific T-cells, DC from *F-hepatica* infected mice induced significantly lower cytokine production, when compared with DC from naïve mice. These findings demonstrate that *F. hepatica* suppresses T cell responses by modulating DC activation and Treg cell induction.

It has been also unexpectedly shown that *F. hepatica* ES modulated DC maturation and enhanced IL-10 production in vitro. Addition of a cathepsin L proteinase inhibitor did not reverse the modulatory effect of ES. Furthermore, injection of mice with ES prevented the development of experimental autoimmune encephalitis (EAE), a murine model for multiple sclerosis. T cells that secrete IL-17, termed ThIL17 cells, are pathogenic in EAE and our data suggests that ES suppresses the induction of ThIL-17 cells, either by inhibiting IL-23, which promotes the expansion of ThIL-17 cells or by inhibiting the activation or function of ThIL-17 cells. The findings suggest that the ES fraction from *F. hepatica* includes components, other than cathepsin L proteinase, which interact with cells of the innate immune system, stimulates the induction of anti-inflammatory cytokines, and activates dendritic cells into a phenotype that promotes the induction of Treg cells, while inhibiting ThIL-17 cells and thereby prevents the development of autoimmune diseases.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. Reference to any prior art in this specification is not, and should not be taken as, an acknowledgment or any form of suggestion that this prior art forms part of the common general knowledge in any country.

The invention claimed is:

1. A method for modulating a T cell mediated immune response, the method comprising the step of: administering to a subject in need of such treatment an effective amount of an agent comprising an excretory secretory (ES) component from *Fasciola hepatica* or a fraction thereof, wherein the excretory secretory (ES) component of *Fasciola hepatica* does not comprise cathepsin L proteinase.

2. A method as claimed in claim 1 wherein in modulating the immune response, the agent serves to mediate at least one of:
(a) an increase in IL-10 cytokine levels in the subject;
(b) an increase in TGF-beta cytokine levels in the subject;
(c) an increase in regulatory T cells;

(d) a decrease in at least one pro-inflammatory cytokine such as IL-12, IL-2 and/or IFN-gamma;
(e) a decrease in cytotoxic T lymphocytes;
(f) a decrease in Th1 cells; or
(g) a decrease in a mixed lymphocyte response.

3. A method as claimed in claim 1 wherein the agent is administered along with a TLR agonist selected from the group comprising Pam3CSK4, Zymosan, PolyIC, LPS, Flagellin and CpG-ODN.

4. A method for treating a subject having a condition that would benefit from the down-regulation of a Th1 immune response, the method comprising the step of: administering to the subject an effective amount of an agent comprising the excretory/secretory (ES) component from *Fasciola hepatica* or a fraction thereof, wherein the excretory secretory ES component of *Fasciola hepatica* does not comprise cathepsin L proteinase.

5. A method for suppressing an immune response suitable for the treatment of an immune-mediated disease in a subject in need of such treatment, the method comprising the steps of:
(a) exposing isolated dendritic cells to an agent comprising an excretory/secretory (ES) component from *Fasciola hepatica* or a fraction thereof ex-vivo in order to modulate dendritic cell function, and
(b) administering the dendritic cells to the subject;
whereby the immune response subsequently induced by the dendritic cells in the subject is sufficient to treat the immune-mediated disease.

6. A method as claimed in claim 5 wherein the disease is an autoimmune disease.

7. A method as claimed in claim 6 wherein the autoimmune disease in Rheumatoid arthritis, colitis or Multiple Sclerosis.

8. A method for eliciting an immune response in a subject suitable for the treatment of an immune-mediated disease, the method comprising the steps of:
(a) exposing isolated dendritic cells to an agent comprising an excretory/secretory (ES) component from *Fasciola hepatica* or a fraction thereof ex-vivo in order to modulate dendritic cell function, and
(b) administering the dendritic cells to the subject;
whereby the immune response generated in the subject is sufficient to treat the immune mediated disease.

9. A method of treatment of an immune-mediated condition, the method comprising the step of: administering an agent comprising an excretory/secretory (ES) component from *Fasciola hepatica* or a fraction thereof wherein the excretory/secretory (ES) component of *Fasciola hepatica* does not comprise cathepsin L proteinase,
wherein the administration of the agent serves to inhibit the production of T cells which secrete IL-17.

10. A method of treatment of an immune-mediated condition, the method comprising the step of: administering an agent comprising the excretory/secretory (ES) component from *Fasciola hepatica* or a fraction thereof wherein be excretory; secretory (ES) component of *Fasciola hepatica* does not comprise cathepsin L proteinase,
wherein the administration of the agent serves to inhibit the production IL-23.

* * * * *

UNITED STATES PATENT AND TRADEMARK OFFICE
CERTIFICATE OF CORRECTION

| | | |
|---|---|---|
| PATENT NO. | : 8,105,601 B2 | Page 1 of 1 |
| APPLICATION NO. | : 12/096239 | |
| DATED | : January 31, 2012 | |
| INVENTOR(S) | : Kingston Mills et al. | |

It is certified that error appears in the above-identified patent and that said Letters Patent is hereby corrected as shown below:

In the Claims

In Column 32, Line 58, in Claim 1, delete "excretory secretory" and insert
-- excretory/secretory --

In Column 32, Line 60, in Claim 1, delete "excretory secretory" and insert
-- excretory/secretory --

In Column 33, Line 15, in Claim 4, delete "excretory secretory" and insert
-- excretory/secretory --

In Column 34, Line 2, in Claim 7, delete "disease in" and insert
-- disease is --

In Column 34, Line 12, in Claim 8, delete "immune mediated" and insert
-- immune-mediated --

In Column 34, Line 25, in Claim 10, delete "excretory; secretory" and insert
-- excretory/secretory --

Signed and Sealed this
Twenty-first Day of October, 2014

Michelle K. Lee
*Deputy Director of the United States Patent and Trademark Office*